US010369211B2

(12) United States Patent
Realpe-Quintero et al.

(10) Patent No.: US 10,369,211 B2
(45) Date of Patent: Aug. 6, 2019

(54) INFLUENZA H5 VACCINES

(71) Applicants: Boehringer Ingelheim Vetmedica GmbH, Ingelheim am Rhein (DE); Boehringer Ingelheim Vetmedica S.A. de C.V., Guadalajara (MX)

(72) Inventors: Mauricio Realpe-Quintero, Jalisco (MX); Paulino Carlos Gonzalez-Hernandez, Hamburg (DE); Eric Vaughn, Ames, IA (US)

(*) Notice: Subject to any disclaimer, the term of this patent is extended or adjusted under 35 U.S.C. 154(b) by 0 days.

(21) Appl. No.: 15/662,358

(22) Filed: Jul. 28, 2017

(65) Prior Publication Data
US 2017/0348413 A1    Dec. 7, 2017

Related U.S. Application Data

(63) Continuation of application No. 14/238,796, filed as application No. PCT/EP2012/065940 on Aug. 15, 2012, now abandoned.

(60) Provisional application No. 61/523,772, filed on Aug. 15, 2011.

(51) Int. Cl.
*A61K 39/145* (2006.01)
*A61K 39/17* (2006.01)
*C07K 14/005* (2006.01)
*A61K 39/12* (2006.01)
*A61K 39/00* (2006.01)

(52) U.S. Cl.
CPC ............ *A61K 39/145* (2013.01); *A61K 39/12* (2013.01); *A61K 39/17* (2013.01); *C07K 14/005* (2013.01); *A61K 2039/5256* (2013.01); *A61K 2039/55555* (2013.01); *A61K 2039/55566* (2013.01); *A61K 2039/70* (2013.01); *C12N 2710/14043* (2013.01); *C12N 2760/16134* (2013.01); *C12N 2760/18134* (2013.01)

(58) Field of Classification Search
None
See application file for complete search history.

(56) References Cited

U.S. PATENT DOCUMENTS

| | | | |
|---|---|---|---|
| 4,552,758 A | 11/1985 | Murphy et al. | |
| 6,204,281 B1 | 3/2001 | Webb et al. | |
| 7,504,109 B2 | 3/2009 | Yang et al. | |
| 7,981,428 B2 | 7/2011 | Wong et al. | |
| 8,202,967 B2 | 6/2012 | Vaughn et al. | |
| 8,592,558 B2 | 11/2013 | Vaughn et al. | |
| 8,883,123 B2 | 11/2014 | Daemmgen et al. | |
| 2004/0071733 A1 | 4/2004 | Takaku et al. | |
| 2004/0146533 A1 | 7/2004 | Miller et al. | |
| 2004/0219208 A1 | 11/2004 | Kawamura et al. | |
| 2005/0042229 A1 | 2/2005 | Yang et al. | |
| 2007/0184526 A1 | 8/2007 | Smith et al. | |
| 2007/0207168 A1 | 9/2007 | Daemmgen et al. | |
| 2010/0150941 A1 | 6/2010 | Hanson et al. | |
| 2012/0231027 A1 | 9/2012 | Vaughn et al. | |
| 2014/0050755 A1 | 2/2014 | Vaughn et al. | |
| 2014/0199337 A1 | 7/2014 | Realpe-Quintero et al. | |
| 2014/0234357 A1 | 8/2014 | Mundt | |
| 2016/0361409 A1 | 12/2016 | Mundt | |
| 2017/0348413 A1 | 12/2017 | Realpe-Quintero et al. | |

FOREIGN PATENT DOCUMENTS

| | | |
|---|---|---|
| CN | 1748795 A | 3/2006 |
| WO | 2005107797 A1 | 11/2005 |
| WO | 2006113214 A2 | 10/2006 |
| WO | 2007019094 A2 | 2/2007 |
| WO | 2007047831 A2 | 4/2007 |
| WO | 2007053446 A2 | 5/2007 |
| WO | 2008052173 A2 | 5/2008 |
| WO | 2011136738 A1 | 11/2011 |
| WO | 2013024113 A1 | 2/2013 |

OTHER PUBLICATIONS

Keitel et al. High doses of purified influenza A virus hemagglutinin significantly augment serum and nasal secretion antibody responses in healthy young adults. J Clin Microbiol. Oct. 1994;32(10):2468-73. (Year: 1994).*
Cinatl et al., "The threat of avian influenza A (H5N1). Part IV: development of vaccines". 2007, Medical Microbiology and Immunology, vol. 196, pp. 213-225.
Claas, et al., "Human influenza A H5N1 virus related to a highly pathogenic avian influenza virus". Feb. 1998, The Lancet, vol. 351, No. 9101, pp. 471-477.
Crawford et al., "Baculovirus-derived hemagglutinin vaccines protect against lethal influenza infections by avian H5 and H7 subtypes". 1999, Vaccine, vol. 17, pp. 2265-2274.
Database UniProtKB/Swiss-Prot Accession No. Q4H2E2, "Hemagglutinin". Oct. 31, 2005, 2 pages.
Dinapoli et al., "Newcastle Disease Virus-Vectored Vaccines Expressing the Hemagglutinin or Neuraminidase Protein of H5N1 Highly Pathogenic Avian Influenza Virus Protect against Virus Challenge in Monkeys". Journal of Virology, vol. 84, No. 3, Feb. 2010, pp. 1489-1503.
Genbank: AAT39065, Version AAT39065.1 GI:47834860, Jun. 6, 2004.
Genbank: AAT39066, Version AAT39066.1 GI:47834862, Jun. 6, 2004.
Genbank: ABA55715, Version ABA55715.1 GI:76800616, Oct. 8, 2005.
Genbank: AY575870, Version AY575870.1 GI:47834861, Jun. 6, 2004.

(Continued)

*Primary Examiner* — Michelle S Horning
(74) *Attorney, Agent, or Firm* — Judy Jarecki-Black

(57) ABSTRACT

The present invention is based on the surprising finding that H5 protein of clade 1 H5N1 induces, in particular by a single-shot vaccination, a cross-clade protective immune response to influenza viruses with H5N1 HA.
In one aspect, the invention is thus directed to H5 protein of clade 1 H5N1 virus for use in a method of treating or preventing infections with H5N1 virus of a different clade, namely of a clade different from clade 1 or from any clade with the exception of clade 1, respectively.

29 Claims, No Drawings
Specification includes a Sequence Listing.

(56) References Cited

OTHER PUBLICATIONS

Genbank: AY845400, Version AY845400.2 GI:61621428, Jan. 1, 2005.
Genbank: BAE07201, Version BAE07201.1 GI:71013498, Jan. 9, 2009.
Guan et al., "H5N1 influenza: A protean pandemic threat". Proceedings of the National Acadmey of Sciences, vol. 101, No. 21, May 2004, pp. 8156-8161.
Hessel et al., "Vectors Based on Modified Vaccinia Ankara Expressing Influenza H5N1 Hemagglutinin Induce Substantial Cross-Glade Protective Immunity". PLoS One, vol. 6, No. 1, Jan. 2011, pp. 1-13.
Hien et al., "Avian Influenza—A Challenge to Global Health Care Structures". 2004, New England Journal of Medicine, vol. 351, No. 23, pp. 2363-2365.
Hoffmann et al., "Role of specific hemagglutinin amino acids in the immunogenicity and protection of H5N1 influenza virus vaccines". Sep. 2005, Proceedings of the National Academy of Sciences, vol. 102, No. 36, pp. 12915-12920.
Hwang et al. "Single dose of oil-adjuvanted inactivated vaccine protects chickens from lethal infections of highly pathogenic H5N1 influenza virus". Vaccine, vol. 29, 2011, pp. 2178-2186.
Iino et al., "Renoprotective Effect of Losartan in Comparison to Amlodipine in Patients with Chronic Kidney Disease and Hypertension—a Report of the Japanese Losartan Therapy Intended for the Global Renal Protection in Hypertensive Patients (JLIGHT) Study." 2004, Hypertension Research, vol. 27, No. 1, pp. 21-30.
International Search Report and Written Opinion for PCT/EP2012/065940 dated Dec. 3, 2012.
Ioannou, et al., "The Immunogenicity and Protective Efficacy of Bovine Herpesvirus 1 Glycoprotein D plus Emulsiger Are Increased by Formulation with CpG Oligodeoxynucleotides". Sep. 2002, Journal of Virology, vol. 76, No. 18, pp. 9002-9010.
Jeon et al., "Protective efficacy of commercial inactivated Newcastle disease virus vaccines in chickens against a revent Korean epizootic strain". Journal of Veterinary Science, vol. 9, No. 3, 2008, pp. 295-300.
Karasin et al., "Isolation and Characterization of H4N6 Avian Influenza Viruses from Pigs with Pneumonia in Canada". Oct. 2000, Journal of Virology, vol. 74, No. 119, pp. 9322-9327.
Knossow et al., "Variation and infectivity neutralization in influenza". 2006, Immunology, vol. 119, pp. 1-7.
Kreijtz et al., "MVA-Based H5N1 Vaccine Affords Cross-Clade Protection in Mice against Influenza A/H5N1 Viruses at Low Doses and after Single Immunization". PLOS One, vol. 4, No. 11, Jan. 2009, pp. 1-8.
Lardinois et al., "Potency of a Recombinant NDV-H5 Vaccine Against Various HPAI H5N1 Virus Challenges in SPF Chickens". Avian Diseases, vol. 56, 2012, pp. 928-936.
Lefebvre et al., "Angiotensin-converting enzyme inhibitors in the therapy of renal diseases". 2004, Journal of Veterinary Pharmacology and Therapeutics, vol. 27, No. 5, pp. 265-281.
Lim et al.,"Mucosal vaccination against influenza: Protection of pigs immunized with inactivated virus of ether-split vaccine". 2001, Journal of Veterinary Research, vol. 48, No. 4, pp. 197-203.
Lipatov et al., "Influenza: Emergence and Control". Sep. 2004, Journal of Virology, vol. 78, No. 17, pp. 8951-8959.
Liu, et al. "Sequence comparison between the extracellular domain of M2 protein human and avian influenza A virus provides new information for bivalent influenza vaccine design". 2005, Microbes and Infection, vol. 7, pp. 171-177.
Lozano-Dubernard et al., "Protection and Differentiation of Infected from Vaccinated Animals by an Inactivated Recombinant Newcastle Disease Virus/Avian Influenza H5 Vaccine". Avian Diseases, vol. 54, Supp. 1, Mar. 2010, pp. 242-245.
Lüschow, et al. "Protection of chickens from lethal avian influenza A virus infection by live-virus vaccination with infectious laryngotracheitis virus recombinants expressing the hemagglutinin (H5) gene". 2001, Vaccine, vol. 19, pp. 4249-4259.
Nwe et al., "Expression of hemagglutinin protein from the avian influenza virus H5N1 in a baculovirus/insect cell system significantly enhanced by suspension culture". BMC Microbiology, vol. 6, No. 16, 2006, (http://www.biomedcentral.com/1471-2180/6/16).
Palese, Peter. "Influenza: old and new threats". Dec. 2004, Nature Medicine Supplement, vol. 10, No. 12, pp. 582-587.
Philippa et al. "Highly pathogenic avian influenza (H7N7): Vaccination of zoo birds and transmission to non-poultry species". 2005, Vaccine, vol. 23, pp. 5743-5750.
Philpott, et al., "Hemagglutinin Mutations Related to Attenuation and Altered Cell Tropism of a Virulent Avian Influenza A Virus". Jun. 1990, Journal of Virology, vol. 64, No. 6, pp. 2941-2947.
Pushko, et al. "Influenza virus-like particles comprised of the HA, NA and M1 proteins of H9N2 influenza virus induce protective immune responses in BALB/c mice". 2005, Vaccine, vol. 23, pp. 5751-5759.
Senne, et al., "Survey of the Hemagglutinin (HA) Cleavage Site Sequence of H5 and H7 Avian Influenza Viruses: Amino Acid Sequence at the HA Cleavage Site as a Marker of Pathogenicity Potential". 1996, Avian Diseases, vol. 40, No. 2, pp. 425-437.
Shinya et al., "Characterization of a Human H5N1 Influenza A Virus Isolated in 2003". Journal of Virology, vol. 79, No. 15, Aug. 2005, pp. 9926-9932.
Snively et al., "Chronic Kidney Disease: Prevention and Treatment of Common Complications". Nov. 2004, American Family Physician, vol. 70, No. 10, pp. 1921-1928.
Stephenson et al. "Confronting the avian influenza threat: vaccine development for a potential pandemic". Aug. 2004, The Lancet Infectious Diseases, vol. 4, pp. 499-509.
Stephenson et al. "Cross-Reactivity to Highly Pathogenic Avian Influenza H5N1 Viruses after Vaccination with Nonadjuvanted and MF59-Adjuvanted Influenza A/Duck/Singapore/97 (H5N3) Vaccine: A Potential Priming Strategy". Apr. 2005, Journal of Infectious Diseases, vol. 191(8), pp. 1210-1215.
Stevens, et al., "Structure and Receptor Specificity of the Hemagglutinin from an H5N1 Influenza Virus". Apr. 2006, Science, vol. 312, pp. 404-410.
Subbarao et al., "Avian influenza viruses infecting humans". 2000, Cellular and Molecular Life Sciences, vol. 57, pp. 1770-1784.
Suga et al., "Angiotensin II type 1 receptor blockade ameliorates tubulointerstitial injury induced by chronic potassium deficiency". 2002, Kidney International, vol. 61, pp. 951-958.
Thomson, "Vaccine Leader: Swine influenza virus . . . combination of pathogen avian influenza and human influenza". 2006, XP002437726, Database accession No. 2007-182327.
Viseshakul et al., "The genome sequence analysis of H5N1 avian influenza A virus isolated from the outbreak among poultry populations in Thailand". Virology, vol. 328, 2003, pp. 169-176.
White et al., "Effects of the Angiotensin II Receptor Blockers Telmisartan Versus Valsartan on the Circadian Variation of Blood Pressure. Impact on the Early Morning Period". 2004, American Journal of Hypertension, vol. 17, pp. 347-353.
Who Global Influenza Program Surveillance Network, "Evolution of H5N1 Avian Influenza Viruses in Asia," Emerging Infectious Diseases, vol. 11, No. 20, 2005 pp. 1515-1521.
Ducatez et al., "Extend of Antigenic Cross-Reactivity among Highly Pathogenic H5N1 Influenza Viruses." Journal of Clinical Microbiology, vol. 49, No. 10, Oct. 2011, pp. 3531-3536.
Terregino, Calogero, et al. "Evaluation of the protection induced by avian influenza vaccines containing a 1994 Mexican H5N2 LPAI seed strain against a 2008 Egyptian H5N1 HPAI virus belonging to clade 2.2. 1 by means of serological and in vivo tests." Avian Pathology 39, No. 3 (2010): 215-222.
Nayak et al.,"Contributions of the avian influenza virus HA, NA, and M2 surface proteins to the induction of neutralizing antibodies and protective immunity." Journal of virology 84, No. 5 (2010): 2408-2420.
Fazekas et al., "Cross-reactive immunity to clade 2 strains of influenza virus A subtype H5N1 induced in adults and elderly patients by Fluval, a prototype pandemic influenza virus vaccine derived by reverse genetics, formulated with a phosphate adjuvant, and directed to clade 1 strains." Clinical and Vaccine Immunology 16, No. 4 (2009): 437-443.

* cited by examiner

INFLUENZA H5 VACCINES

SEQUENCE LISTING

This application contains a sequence listing in accordance with 37 C.F.R. 1.821-1.825. The sequence listing accompanying this application is hereby incorporated by reference in its entirety.

FIELD OF THE INVENTION

The present invention relates to the field of medicine, preferably to the field of infectious diseases. In particular the present invention relates to influenza proteins and vaccines. Most particularly, the present invention relates to the use of any of such proteins or vaccines for the treatment and prevention of influenza infections, furthermore for the prevention of intra- and inter-species transmission of influenza virus.

BACKGROUND OF THE INVENTION

Influenza infection remains an important infection in animals and humans. Influenza is caused by viruses that undergo continuous antigenic changes/modifications and that possess an animal reservoir. Thus new epidemics and pandemics may occur in the future, and eradication of the disease will be difficult to achieve. Influenza viruses are well known in the art and described more in detail for example by P. Palese, *Nature Medicine*, vol. 10, no. 12, pp. S 82 to S 86 of December 2004, with further references. Briefly, the genome of the influenza A virus consists of eight single-stranded segments, and the viral particles has two major glycoproteins on its surface: hemagglutinin (H) and neuraminidase (N). With at least 16 different hemagglutinin (H1 to H16) and 9 different neuraminidase (N1 to N9) subtypes, there is a considerable antigenic variation among influenza viruses.

Influenza virus of type H5N1 Fowl Plague virus has been demonstrated to infect poultry, pigs and man. The viruses can also be transmitted directly from avian species to humans (Claas et al., *Lancet* 1998, 351: 472; Suarez et al., *J. Virol.* 1998, 72: 6678; Subbarao et al., *Science* 1998, 279: 393; Shortridge, *Vaccine* 1999, 17 (Suppl. 1): S26-S29). Mortality in known human clinical cases approaches about 50%.

Over the last century pigs have been an important vector for influenza pandemics. Pigs, camels, and seals, preferably pigs, can serve as a 'mixing chamber' for avian influenza viruses, and therefore represent a potential risk factor for overcoming the species hurdles from poultry, the naturally reservoir of influenza viruses, to mammals. This normally occurs by double infections of the susceptible animals, e.g. pig, with both, an established mammalian (porcine), as well as an avian influenza virus. This double infection may create new recombinant viruses that may be the cause of human or porcine pandemics. Recent evidence would, however, indicate that a recombination of current avian H5 strains with mammalian influenza viruses will not result in highly virulent recombinants. On the other hand, avian influenza virus can infect pigs and by spontaneous mutations can become adapted to pigs. The critical hurdle will be overcome as soon as the virus can cause horizontal infections within a pig (or other mammalian) population.

Yet, a major part of Southeast Asian pigs have been infected with avian (H5) influenza virus strains originating from neighbouring poultry husbandry. As those infections have so far been sub-clinical, they can only be diagnosed by laboratory methods and thus are frequently overlooked. There is a high risk that those sub-clinically-infected pigs will serve as an opportunity for the virus to adapt to the mammalian system, spread within the porcine population, and also infect human beings.

Current influenza vaccines include a subunit vaccine (Babai et al., Vaccine 1999, 17 (9-10):1223-1238; Crawford et al., Vaccine 1999, 17 (18):2265-2274; Johansson et al., Vaccine 1999, 17 (15-16):2073-2080) attenuated vaccine (Horimoto et al., Vaccine 2004, 22 (17-18):2244-2247), DNA vaccine (Watabe et al., Vaccine 2001, 19 (31):4434-4444) and inactivated influenza vaccine (Cao et al., Vaccine 1992, 10 (4):238-242), with the latter being the most widely used on a commercial scale (Lipatov et al., J Virol 2004, 78 (17):8951-8959).

Subunit vaccines, recombinant hemagglutinin and neuraminidase (Babai et al., Vaccine 1999, 17 (9-10):1223-1238; Crawford et al., Vaccine 1999, 17 (18):2265-2274; Johansson et al., Vaccine 1999, 17 (15-16):2073-2080) may be an attractive alternative to the inactivated vaccine, although none are currently in use as commercial vaccines. The preparation of such vaccines is obviously safer than for an inactivated vaccine. Moreover, subunit vaccines do not generate antibody responses to internal influenza viral proteins and thus allow distinction between vaccinated and infected animals (Crawford et al., Vaccine 1999, 17 (18): 2265-2274).

Hemagglutinin protein is the receptor-binding and membrane fusion glycoprotein of influenza virus and the target for infectivity-neutralizing antibodies. The entire hemagglutinin protein (HA) from the H5N1 is composed of 568 amino acids, with a molecular weight of 56 kDa. The HA molecule consists of HA1 and HA2 subunits, with the HA1 subunit mediating initial contact with the cell membrane and HA2 being responsible for membrane fusion (Chizmadzhev, *Bioelectrochemistry* 2004, 63 (1-2):129-136).

Baculovirus/insect cell systems have been used to express hemagglutinin genes isolated from avian influenza subtypes (Babai et al., Vaccine 1999, 17 (9-10):1223-1238; Crawford et al., Vaccine 1999, 17 (18):2265-2274; Johansson et al., Vaccine 1999, 17 (15-16):2073-2080); Nwe et al., BMC Mircobiology 2006, 6 (16):doi:10.1186/1471-2180-6-16). However, those recombinant proteins seem not to be protective in any case, or only less effective at least for some species (Treanor et al., Vaccine 2001, 19: 1732-1737).

The document Lin et al. (J Vet Med Sci. 2008 70 (11): 1147-52) discloses the use of a baculovirus/insect cell system for the production of H5 protein of clade 2 H5N1 virus A/duck/China/E319-2/03, which is usable for a prime-booster vaccination for preventing an infection with the clade 2 virus A/duck/China/E319-2/03.

Bright et al. (PLoS One. 2008 30; 3 (1):e1501) describes the use of a baculovirus/insect cell system for generating virus-like particles (VLPs) which include neuraminidase, hemagglutinin and matrix 1 protein from clade 2 H5N1 virus for inducing a cross-clade protective immune response against a challenge with clade 1 H5N1 virus A/VN/1203/2004 in mice. However, the production of VLPs is not without problems, since in order to generate a functional VLP that effectively mimic a real virus, multiple virus structural proteins are needed which must then be correctly assembled into a particle that reproduces the confirmation of the outer shell (capsid) of the infectious virus. Further, study also reals that in vitro assembly of VLPs competes with aggregation (Ding et al. Biotechnology and Bioengineering 107 (3): 550-560).

Thus, there is a need to increase availability of improved vaccines and new vaccination approaches to provide better approaches to control influenza infections and to have a positive impact on disease load. In particular, there is a strong need for a simple, effective and easy-to-handle system inducing, preferably by a single-shot vaccination, a cross-clade protective immune response to influenza viruses with H5N1 HA.

DESCRIPTION OF THE INVENTION

Before the embodiments of the present invention it shall be noted that as used herein and in the appended claims, the singular forms "a", "an", and "the" include plural reference unless the context clearly dictates otherwise. Thus, for example, reference to "a preparation" includes a plurality of such preparations; reference to the "carrier" is a reference to one or more carriers and equivalents thereof known to those skilled in the art, and so forth. Unless defined otherwise, all technical and scientific terms used herein have the same meanings as commonly understood by one of ordinary skill in the art to which this invention belongs. All given ranges and values may vary by 1 to 5% unless indicated otherwise or known otherwise by the person skilled in the art, therefore, the term "about" was omitted from the description. Although any methods and materials similar or equivalent to those described herein can be used in the practice or testing of the present invention, the preferred methods, devices, and materials are now described. All publications mentioned herein are incorporated herein by reference for the purpose of describing and disclosing the substances, excipients, carriers, and methodologies as reported in the publications which might be used in connection with the invention. Nothing herein is to be construed as an admission that the invention is not entitled to antedate such disclosure by virtue of prior invention.

The solution to the above technical problem is achieved by the description and the embodiments characterized in the claims.

Influenza Proteins and Nucleic Acid Molecules Coding for Those

The present invention is based on the surprising finding that H5 protein of clade 1 H5N1 induces, in particular by a single-shot vaccination, a cross-clade protective immune response to influenza viruses with H5N1 HA. As one feature, the H5 protein of clade 1 H5N1 virus, which is for reasons of clarity also termed "H5 protein (1)" herein, comprises or consists of a polypeptide sequence having at least 98% sequence identity with the polypeptide sequence set forth in SEQ ID NO:1.

A "single-shot vaccination" refers to an immunogenic composition that is effective at reducing the incidence of or severity of infection after a single dose thereof, without the need for a booster.

In one aspect, the invention is thus directed to H5 protein (1) of clade 1 H5N1 virus for use in a method of treating or preventing infections with H5N1 virus of a different clade, namely of a clade different from clade 1 or from any clade with the exception of clade 1, respectively, wherein said H5 protein (1) comprises or consists of a polypeptide sequence having at least 98% sequence identity with the polypeptide sequence of SEQ ID NO:1.

The term "clade" or "clades" as used herein relates to the clade(s) of the WHO Nomenclature System for the highly Pathogenic Avian Influenza Virus (H5N1), which is summarized at the WHO website www.who.int (Dec. 8, 2011), which is incorporated herein by reference.

10 distinct initial clades of viruses (numbered 0-9) are defined (WHO/OIE/FAO H5N1 Evolution Working Group, 2008), which are called first order clades. Clades are strictly defined on the nucleotide level as meeting the following three specific clade definition criteria developed by the WHO/OIE/FAO H5N1 Evolution Working Group:
sharing of a common (clade-defining) node;
monophyletic grouping with a bootstrap value of ≥60 at the clade-defining node (after 1000 neighbor-joining bootstrap replicates); and
average percentage pairwise nucleotide distances between and within clades of >1.5% and <1.5%, respectively.

As the viruses within these 10 clades continue to evolve, new sublineages (potential H5N1 clades) periodically emerge. Once these sublineages meet the same three specific clade definition criteria as the initial 10 clades (numbered 0-9), they are designated as separate clades (WHO/OIE/FAO H5N1 Evolution Working Group Emerg. Inf. Dis. 14, 7 (2008). These new clades are defined as second (or third, etc) order clades and assigned a numerical 'address' which links them to their original clade using a hierarchical decimal numbering system. For example, within the antigenically distinct clade 2.3, third order clades meeting the clade definition are designated as clades 2.3.1 and 2.3.2 and so on. This logical hierarchal numbering system is objectively related to HA phylogeny.

The criteria used for the clade designation according to the WHO Nomenclature System for H5N1 are:
1 Maintain previously designated clade numbers where possible (i.e., clade 2.2 remains 2.2 and clade 1 remains 1)
2 New clade designations based on phylogenetic tree topology derived from all available sequences (the large tree)
  H5N1 progenitors (closest to Gs/Guangdong/1/96) redesignated as clade 0
  Subsequent clades numbered starting from clade 3 (i.e., clades 3-9)
  Clades designated by presence of a distinct common node shared by at least 4 isolates (in a monophyletic group)
  Additional branches designated as a single clade evolves into more than one distinct lineage (i.e., clade 2.2 or clade 2.3.1; based on sharing of a common node and monophyletic grouping)
3 Average percentage pairwise distances between and within clades (using Kimura 2-parameter)
  Distinct clades should have >1.5% average distances between other clades
  Distinct clades should have <1.5% average distances within the clade (may be slightly higher in clades with highly evolved outliers; i.e., Ck/Shanxi/2/2006 in clade 7)
4 Bootstrap (based on 1,000 neighbor-joining bootstrap replicates) ≥60% bootstrap value at clade-defining node
(taken from Table 1 of: WHO/OIE/FAO H5N1 Evolution Working Group Emerg. Inf. Dis. 14, 7 (2008)).

The prototype strain for each clade is listed in the following Table:

| Clade | Prototype strain |
|---|---|
| 0 | Gs/Guangdong/1/96 |
| 3 | Ck/Hong Kong/YU562/2001 |
| 4 | Gs/Guiyang/337/2006 |
| 5 | Gs/Guangxi/914/2004 |

| Clade | Prototype strain |
|---|---|
| 6 | Ck/Hunan/01/2004 |
| 7 | Ck/Shanxi/2/2006 |
| 8 | Ck/Hong Kong/YU777/2002 |
| 9 | Dk/Guangxi/2775/2005 |
| 1 | Vietnam/1203/2004 |
| 2.1.1 | Ck/Indonesia/BL/2003 |
| 2.1.2 | Indonesia/538H/2006 |
| 2.1.3 | Indonesia/5/2005 |
| 2.2 | BHGs/Qinghai/1A/2005 |
| 2.3.1 | Dk/Hunan/303/2004 |
| 2.3.2 | Ck/Guangxi/2461/2004 |
| 2.3.3 | Ck/Guiyang/3055/2005 |
| 2.3.4 | Dk/Fujian/1734/2005 |
| 2.4 | Ck/Yunnan/115/2004 |
| 2.5 | Ck/Korea/ES/2003 |
| 2.5 | Ck/Korea/ES/2003 |

(taken from Table 2 of: WHO/OIE/FAO H5N1 Evolution Working Group Emerg. Inf. Dis. 14, 7 (2008)).

The publication WHO/OIE/FAO H5N1 Evolution Working Group Emerg. Inf. Dis. 14, 7 (2008), which is incorporated herein by reference, is found at the CDC website www.cdc.gov (Aug. 12, 2011).

An overview of the clade classification of known H5N1 viruses is provided by the phylogenetic tree at the WHO website www.who.int (Aug. 15, 2011), which is hereby incorporated by reference.

For determining the clade of a H5 protein of H5N1, for example, the web based tool "Highly Pathogenic Avian Influenza (HPAI) H5N1 HA clade prediction" can be used, which is described by Lu, Davis, Rowley, and Donis: "A Web-based tool for the clade designation of highly pathogenic avian influenza H5N1 viruses" in Options for the Control of Influenza VI. J. M. Katz, N. Cox & A. W. Hampson (Eds.) London: Blackwell, 2007, herein incorporated by reference, and which is found at the website www.flugenome.org (Aug. 12, 2011).

For example, a H5 protein of clade 1 H5N1 virus (H5 protein (1)) is thus a HA with an amino acid sequence encoded by a nucleotide sequence of a clade 1 according to the above-mentioned WHO Nomenclature System for H5N1.

A clade 2.3.1 H5N1 virus, for instance, is hence a H5N1 falling under the criteria of a clade 2.3.1 according to the above-mentioned WHO Nomenclature System for H5N1.

In a preferred embodiment, the H5 protein (1) according to the invention, namely the H5 protein of clade 1 H5N1 virus as described herein, comprises or consists of a polypeptide sequence having at least 98.1%, preferably at least 98.2%, more preferably at least 98.3%, and most preferably at least 98.4% sequence identity with the polypeptide sequence of SEQ ID NO:1.

Sequence identity in the context of the invention is understood as being based on determined pairwise similarity between protein sequences. The determination of percent similarity between two sequences is preferably accomplished using a computational algorithm, in particular the well-known Basic Local Alignment Search Tool (Altschul S F, Gish W, Miller W, Myers E W, Lipman D J: Basic local alignment search tool. J Mol Biol 1990, 215 (3):403-410). For purposes of the present invention, percent sequence identity of an amino acid sequence is determined using the BLAST blastp homology search algorithm using the following parameters: an expected threshold of 10, word size 3, BLOSUM62 matrix, gap opening penalty of 11, a gap extension penalty of 1, and conditional compositional score matrix adjustment. The database to search against is the set of non-redundant protein sequences (nr). The BLAST homology search algorithm is described in Altschul S F (1990), J Mol Biol 1990, 215 (3):403-410, which is herein incorporated by reference.

A variant may, for example, differ from the reference accession number BAE07201 molecule without signal peptide (N-terminal 16 amino acid residues are not shown in SEQ ID NO:1) by as few as 1 to 15 amino acid residues, as few as 1 to 10 amino acid residues, such as 6-10, as few as 5, as few as 4, 3, 2, or even 1 amino acid residue.

In one exemplary embodiment, the H5 protein (1) according to the invention, i.e. the H5 protein (1) of clade 1 H5N1 virus for use in a method of treating or preventing infections with H5N1 virus of a different clade, is preferably a H5 protein of influenza virus, wherein the H5 protein having the amino acid 223N and the modification 328K+, wherein numbering of the amino acid positions of the H5 protein refers to the amino acid position as exemplarily given in SEQ ID NO:2 and wherein the modification 328K+ means that at amino acid position 328 of H5 protein a second Lysine (K+) is inserted. Said preferred H5 protein (1) is also termed Mut k+ or mutK+ in the following. Preferably, such H5 protein and any further H5 protein according to the invention is an isolated H5 protein.

The term "H5 protein (1) of clade 1 H5N1", as used herein, preferably means "H5 protein (1) as single antigen of clade 1 H5N1 virus" or in particular "H5 protein (1) as single antigen".

The terms "hemagglutinin 5 (H5)" or "H5 of avian influenza virus" or "H5 protein" as used herein are equivalent and mean, but are not limited to any naturally occurring H5 protein and any modified forms of H5 protein, including any deletion, substitution and/or insertion mutant of H5 protein.

The numbering of the amino acid positions of the H5 protein (1) Mut k+ as used herein refers to the amino acid position as exemplarily given in SEQ ID NO:2. SEQ ID NO:2 represents the amino sequence of the hemagglutinin of strain duck/China/E319-2/03 but lacking the amino terminal signal peptide. In other words, if reference is made to the amino acid at position 223 (amino acid 223), the amino acid residue is meant which corresponds to amino acid 223 of SEQ ID NO:2. However, this does not mean that the H5 protein Mut k+ according to the invention has the identical amino acid sequence with SEQ ID NO:2. It only says, that the corresponding amino acids of the H5 proteins according to the inventions code for the amino acid residue, as explicitly mentioned. In the current case, amino acid 223 would be Serine (S). The terms "223N", or "155N" exemplarily mean, that the amino acid at positions 223 and 155, respectively—numbering according to the amino acid positions of SEQ ID NO:2—, that shall code for the amino acid Asparagine (N). In other words, if reference is made to "H5 protein (1) having the amino acid 223N", a H5 amino acid molecule that normally codes for Serine at amino acid position 223—numbering according to the amino acid positions of SEQ ID NO:2—that amino acid shall be substituted by an Asparagine (N). The term "328K+" or "modification 328K+" means, that at amino acid position 328 of H5 protein—numbering according to the amino acid positions of SEQ ID NO:2—, a second Lysine (K+) is inserted. In cases were amino acids sequences at positions 328 and 329 naturally codes for Lysine-Lysine, no further Lysine (K) shall be inserted. However, most of the known H5 sequences code at amino acid positions 328 and 329 for Lysine-Arginine. In any such cases, the term 328K+ modification means, that a second Lysine (K) shall be inserted between Lysine at position 328 and Arginine at position 329. The modified sequence would read then Lysine-Lysine-Arginine (KKR).

Regarding the present example, the hemagglutinin of strain duck/China/E319-2/03 is shifted to a H5 protein (1) of clade 1 H5N1, since it resembles the H5 sequence of the clade 1 H5N1 virus A/HongKong/213/2003, the year/location/host of this HK isolate, and shows reactivity with clade-1-specific antibodies. Hence the Mut K+ sequence is classified as a H5 sequence of a clade 1 H5N1. Within the context of the invention, the designed Mut K+ sequence is thus understood and defined to be a H5 protein of clade 1 H5N1 virus.

Thus, in particular also any designed H5 protein is understood and defined as a H5 protein of clade 1 H5N1 virus according to the invention, if it is encoded by a nucleotide sequence which fulfils the criteria of a nucleotide sequence of a clade 1 according to the above-mentioned WHO Nomenclature System for H5N1.

Thus, in one embodiment, the present invention is implemented with a H5 protein and any modified forms of H5 protein, including any deletion, substitution and/or insertion mutant of H5 protein, wherein those H5 proteins having the amino acid 223N and the modification 328K+, wherein numbering of the amino acid positions of the H5 protein refers to the amino acid position as exemplarily given in SEQ ID NO:2 and wherein the modification 328K+ means that at amino acid position 328 of H5 protein a second Lysine (K+) is inserted. It is self-explanatory, that any of the H5 proteins as provided herewith are antigenic, which mean they show antigenic properties in an standard hemagglutinin inhibition assay for influenza viruses.

According to a further embodiment, the present invention also relates to any part of the H5 protein (1), which means any peptide-fragment which shows antigenic properties in an standard hemagglutinin inhibition assay, having in one embodiment at least the amino acid 223N and the modification 328K+, wherein numbering of the amino acid positions of the H5 protein refers to the amino acid position as exemplarily given in SEQ ID NO:2 and wherein the modification 328K+ means that at amino acid position 328 of H5 protein a second Lysine (K+) is inserted.

A H5 protein (1) shows antigenic properties if it inhibits hemagglutination in a standard hemagglutinin inhibition assay, for example, as described in Example 2. Normally said antigenic part of H5 protein (1) comprises 200, 180, 160, 150, 140, 130, 120, 110 or most preferably 105 contiguous amino acids of the amino acid sequence that codes for the H5 protein as mentioned above, modified or non-modified, which shows antigenic properties in an standard hemagglutinin inhibition assay as described in Example 2. A standard hemagglutinin inhibition assay for example is also described in Stephenson et al., Virus Research vol. 103, pp. 91-95 (2004) with further references. However, the HI assay as described in Example 2 shall be understood to be the relevant reference assay in connection with all aspects of the invention as described herein:

Briefly, HI assay was performed to detect the presence of HA-specific antibodies. A heterologous H5N2 virus, A/chicken/Mexico/232/94, was used at a concentration of four hemagglutinating units [4 HA units] in the HI assay. In U-bottomed microtiter plates serial two-fold serum dilutions in PBS were subsequently mixed with equal volumes (25 µL) containing 4 HA units of virus, and incubated at room temperature (about 25° C.) for 30 min. Chicken red blood cells, at a concentration of 0.5% in PBS, were added to the serum-virus containing wells and incubated for 40 min at room temperature. The HI titers were determined as reciprocals of the highest serum dilutions in which inhibition of hemagglutination was observed.

Of note, Haesebrouck and Pensaert (1986) found "that there may exist a correlation between the HI titers against the challenge virus and protection from challenge". Haesebrouck and Pensaert (1986) also determined that pigs with HI titers of ≥40 were "completely resistant to challenge and no replication of the virus occurred in the respiratory tract at challenge". Thus, the development of HI titers ≥40 in the vaccinated swine would correlate to protection. (F. Haesebrouck and M. B. Pensaert, 1986). Effect of intratracheal challenge of fattening pigs previously immunized with an inactivated influenza H1N1 vaccine (*Veterinary Microbiology*, 11 (1986) 239-249. It has to assume that equivalent or at least nearly equivalent H5 HI titers will also result in a complete immune protection of swine against avian influenza virus. Lower titers, at least result in a seroconversion of the vaccinated animals and result in partial immune protection of those animals, which also can dramatically reduce the risk of a pandemics.

Moreover, an antigenic part of the H5 protein (1) according to the invention includes, but is not limited to deletion mutants of H5 protein, which comprises:
(i) at least 35, 30, 25, 20, 18, 15, 13, 10, 9, or most preferably 8 contiguous amino acids of the amino acid sequence that surrounds and includes the amino acid 223N; and
(ii) at least 35, 30, 25, 20, 18, 15, 13, 10, 9, or most preferably 8 contiguous amino acids of the amino acid sequence that surrounds and includes the amino acid modification 328K+, and
(iii) wherein any of such antigenic part of H5 protein shows hemagglutinin inhibition in a standard hemagglutinin inhibition assay as described in Example 2.

Preferably, those surrounding amino acids of amino acid 223N and/or 328K+ are encoded by SEQ ID NO:2 or SEQ ID NO:5.

Furthermore preferred H5 proteins (1) according to the invention are:
(i) any of those mentioned above having the amino acid 223N and the modification 328K+;
(ii) any of those mentioned above having the amino acid 94N/223N and the modification 328K+;
(iii) any H5 protein of avian origin having the amino acid 223N, and the modification 328K+, wherein avian origin means that the H5 sequence derived form a virus isolate that was originally isolated from a poultry infected with avian influenza virus type 5; or
(iv) any H5 protein of avian origin having the amino acids 94N/223N and the modification 328K+, wherein avian origin means that the H5 sequence derived from a virus isolate that was originally isolated from poultry infected with avian influenza virus type 5; or
(v) any H5 protein of avian origin having the amino acids 155N/223N and the modification 328K+, wherein avian origin means that the H5 sequence derived from a virus isolate that was originally isolated from poultry infected with avian influenza virus type 5; or
(vi) any H5 protein of avian origin having the amino acid 120N/155N/223N and the modification 328K+, wherein avian origin means that the H5 sequence derived from a virus isolate that was originally isolated from poultry infected with avian influenza virus type 5; or
(vii) any H5 protein having the modifications 94N/223N and the modification 328K+; or (viii) any H5 protein having the modifications 94N/155N/223N and the modification 328K+; or;
(ix) any H5 protein having the modifications 94N/120N/155N/223N and the modification 328K+; or
(x) any H5 protein having the modifications 223N, the modification 328K+, and one or more of the following amino acid clusters selected from the group consisting of:
  a. aa 93-95: GNF
  b. aa 123-125: SDH
  c. aa 128-130: SSG
  d. aa 138-140: GSS
  e. aa 226-228: MDF
  f. aa 270-272: EVE
  g. aa 309-311: NKL; or
(xi) any H5 protein having the amino acid 223N, and the modification 328K+, and one or more of the following amino acid clusters selected from the group consisting of:
  a. aa 93-95: GNF
  b. aa 128-130: SSG
  c. aa 138-140: GSS; or
(xii) any H5 protein having the amino acid sequence of SEQ ID NO:5.

Furthermore preferred H5 proteins (1) as provided herewith include the H5 proteins as described by Hoffmann et al, *PNAS*, vol. 106, no. 36, pp. 12915-12920 of Sep. 6, 2005, wherein that H5 proteins includes one or more of the modifications as described above, at least the amino acid 223N and the modification 328K+, wherein numbering of the amino acid positions of the H5 protein refers to the amino acid position as exemplarily given in SEQ ID NO:2 and wherein the modification 328K+ means that at amino acid position 328 of H5 protein a second Lysine (K+) is inserted. The disclosure of this reference shall be entirely included herein by reference.

Furthermore preferred H5 proteins (1) as provided herewith include H5 proteins which comprise a peptide that comprises the amino acid 223N and the modification 328K+, wherein numbering of the amino acid positions of the H5 protein refers to the amino acid position as exemplarily given in SEQ ID NO:2 and wherein the modification 328K+ means that at amino acid position 328 of H5 protein a second Lysine (K+) is inserted, and:
(i) the amino acid sequences of SEQ ID NO:2, SEQ ID NO:3, SEQ ID NO:4; SEQ ID NO:5; SEQ ID NO:6 or SEQ ID NO:7 or;
(ii) any peptide that has at least 85% sequence homology, more preferably at least about 90% sequence homology, still more preferably at least about 95% sequence homology, even more preferably at least about 97% sequence homology, still even more preferably at least about 98% sequence homology, and even more preferably at least about 99% sequence homology to the polypeptide of i) that comprises hemagglutinin inhibition in a standard hemagglutinin inhibition as described above; or
(iii) any antigenic part of the polypeptides of i) or ii) comprising at least 35, 30, 25, 20, 18, 15, 13, 10, 9, or most preferably 8 contiguous amino acids of any of peptides of i) or ii).
(iv) any peptides of i), ii) or iii) having the amino acids 36T, 36K, 83A, 83T, 83D, 86A, 86V, 120N, 120S, 155N, 155S, 156A, 156T, 189R, 189K, 212K, 212R, 212E, 223N, 223N, or 120N/155N.
(v) any peptide of i), ii), iii) or iv) having one or more of the following amino acid clusters selected from the group consisting of:
  a. aa 93-95: GNF
  b. aa 123-125: SDH
  c. aa 128-130: SSG
  d. aa 138-140: GSS
  e. aa 226-228: MDF
  f. aa 270-272: EVE
  g. aa 309-311: NKL; or
(vi) any peptide of i), ii) iii) or iv) having one or more of the following amino acid clusters selected from the group consisting of:
  a. aa 93-95: GNF
  b. aa 128-130: SSG
  c. aa 138-140: GSS.

"Sequence homology", as used herein, refers to a method of determining the relatedness of two sequences. To determine sequence homology, two or more sequences are optimally aligned, and gaps are introduced if necessary. In contrast to sequence identity, conservative amino acid substitutions are counted as a match when determining sequence homology. In other words, to obtain a polypeptide or polynucleotide having 95% sequence homology with a reference sequence, 85%, preferably 90%, even more preferably 95% of the amino acid residues or nucleotides in the reference sequence must match or comprise a conservative substitution with another amino acid or nucleotide, or a number of amino acids or nucleotides up to 15%, preferably up to 10%, even more preferably up to 5% of the total amino acid residues or nucleotides, not including conservative substitutions, in the reference sequence may be inserted into the reference sequence. Preferably the homolog sequence comprises at least a stretch of 50, even more preferred of 100, even more preferred of 250, even more preferred of 500 nucleotides. Upon such alignment, sequence homology is ascertained on a position-by-position basis, e.g., the sequences are "homolog" at a particular position if at that position, the nucleotides or amino acid residues are identical. The total number of such position identities is then divided by the total number of nucleotides or amino acid residues in the reference sequence to give % sequence homology. Sequence homology can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence homology are designed to give the largest match between the sequences tested. Methods to determine sequence homology are codified in publicly available computer programs which determine sequence identity between given sequences. Examples of such programs include, but are not limited to, the GCG program package (Devereux, J., et al., Nucleic Acids Research, 12 (1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence homology between the given and reference sequences.

Furthermore preferred H5 proteins (1) include H5 proteins which comprise the 328K+ modification as mentioned above, and the amino acid sequence provided in TABLE 1, or any immunogenic part thereof:

TABLE 1

H5 antigens

| Sequence name | Basic-sequence | Amino acid positions[#] | | | | | | | | | |
|---|---|---|---|---|---|---|---|---|---|---|---|
| | | 36 | 83 | 86 | 120 | 155 | 156 | 189 | 212 | 223 | 263 |
| 223N/328K+ | any HA H5 | — | — | — | — | — | — | — | — | N | — |
| 36T/223N/328K+ | any HA H5 | T | — | — | — | — | — | — | — | N | — |
| 36K/223N/328K+ | any HA H5 | K | — | — | — | — | — | — | — | N | — |
| 83A/223N/328k+ | any HA H5 | — | A | — | — | — | — | — | — | N | — |
| 83T/223N/328k+ | any HA H5 | — | T | — | — | — | — | — | — | N | — |
| 83D/223N/328k+ | any HA H5 | — | D | — | — | — | — | — | — | N | — |
| 86A/223N/328k+ | any HA H5 | — | — | A | — | — | — | — | — | N | — |
| 86V/223N/328k+ | any HA H5 | — | — | V | — | — | — | — | — | N | — |
| 120N/223N/328k+ | any HA H5 | — | — | — | N | — | — | — | — | N | — |
| 120S/223N/328k+ | any HA H5 | — | — | — | S | — | — | — | — | N | — |
| 155N/223N/328k+ | any HA H5 | — | — | — | — | N | — | — | — | N | — |
| 155S/223N/328k+ | any HA H5 | — | — | — | — | S | — | — | — | N | — |
| 156A/223N/328k+ | any HA H5 | — | — | — | — | — | A | — | — | N | — |
| 156T/223N/328k+ | any HA H5 | — | — | — | — | — | T | — | — | N | — |
| 189R/223N/328k+ | any HA H5 | — | — | — | — | — | — | R | — | N | — |
| 189K/223N/328k+ | any HA H5 | — | — | — | — | — | — | K | — | N | — |
| 212K/223N/328k+ | any HA H5 | — | — | — | — | — | — | — | K | N | — |
| 212R/223N/328k+ | any HA H5 | — | — | — | — | — | — | — | R | N | — |
| 212E/223N/328k+ | any HA H5 | — | — | — | — | — | — | — | E | N | A |
| 223N/263A/328k+ | any HA H5 | — | — | — | — | — | — | — | — | N | A |
| 223N/263T/328k+ | any HA H5 | — | — | — | — | — | — | — | — | N | T |
| 120N/155N/223N/328k+ | any HA H5 | — | — | — | N | N | — | — | — | N | — |
| A/duck/China/E319-2/03/328k+ | AAR99628 | T | A | A | S | D | A | R | K | N | A |
| A/duck/China/E319-2/03_223N/328k+ | AAR99628 | T | A | A | S | D | A | R | K | N | A |
| A/duck/China/E319-2/03_120N/223N/328k+ | AAR99628 | T | A | A | N | D | A | R | K | N | A |
| A/duck/China/E319-2/03_155N/223N/328k+ | AAR99628 | T | A | A | S | N | A | R | K | N | A |
| A/duck/China/E319-2/03_120N/155N/223N/328k+ | AAR99628 | T | A | A | S | N | N | R | K | N | A |
| HA/HK/213/03/328k+ | AY518362 | T | A | A | N | N | A | R | K | N | A |
| HA/Vietnam/1203/04 | | K | T | V | S | S | T | K | R | N | T |
| HA/Vietnam/1203/04_223N/328k+ | | K | T | V | S | S | T | K | R | N | T |
| HA//Vietnam/3046/04_223N/328k+ | | T | A | V | S | S | T | K | R | N | T |
| HA/Vietnam/3062/04_223N/328k+ | | T | A | V | S | S | T | K | R | N | T |
| HA/chicken/Vietnam/39/04_223N/328k+ | | T | A | V | S | S | T | K | R | N | T |
| HA/falcon/HK-D0028/04_223N/328k+ | | T | A | A | S | S | A | K | E | N | A |
| HA/duck/Singapore/3/97_223N/328k+ | | T | D | V | S | N | A | K | E | N | A |
| HA/HK/156/97/328k+ | | T | A | A | S | S | A | K | E | N | T |

[#]the amino acid positions given in TABLE 1 refers to the positions as exemplarily defined in SEQ ID NO: 2. In other words amino acid 223 of TABLE 1 refers to the amino acid 223 of the sequence of SEQ ID NO: 2.
— means that the amino acids at this positions are variable as compared to the reference sequence.

Furthermore, the present invention also relates to H5 proteins (1) having at least the amino acid 223N and the modification 328K+, wherein numbering of the amino acid positions of the H5 protein refers to the amino acid position as exemplarily given in SEQ ID NO:2 and wherein the modification 328K+ means that at amino acid position 328 of H5 protein a second Lysine (K+) is inserted, and comprises:
i. a peptide having the sequences of NCBI Accession No. AAT65209, CAJ32556, ABC47656, CAF21874, CAF21870, AAC58998, AAC58997, AAC58996, AAC58994, AAC58993, AAC58992, AAC58991, AAC58990, AAC58995, AAS45134, AAN17270, AAN17269, AAN17268, AAN17267, AAN17266, AAN17265, AAN17264, AAN17263, AAN17262, AAN17261, AAN17260, AAN17259, AAN17257, AAN17256, AAN17255, AAN17254, AAA43083, AAA43082, AAB19079, BAE48696, BAE48693, BAE48696, BAE48695, BAE48694, BAE48692, BAE48691, BAE48690, BAE48689, BAE48688, BAE48687, BAE48686, BAE48685, BAE48684, BAE48683, AAC58999, ABC72082, AAV91149, AAP71993, AAP71992, AAP71991, AAP71990, AAP71989, AAP72011, AAP72010, AAP72009, AAP72008, AAP72007, AAP72006, AAP72005, AAP72004, AAP72003, AAP72002, AAP72001, AAP72000, AAP71999, AAP71998, AAP71997, AAP71996, AAP71995, AAP71994, AAF99718, ABF58847, AAG38534, AAC32102, AAC32099, AAL75847, AAC32101, AAC32098, AAC32088, AAC32078, AAR99628, AAC32100, AAM49555, AAL75843, AAL75839, AAD13573, AAD13568, AAF04720, AAF04719, AAC34263, AAR16155, AAD13574, AAD13570, AAD13575, AAD13572, AAD13569, AAD13567, AAD13566, AAK57506, AAG01225, AAG01215, AAG01205, AAG01195, or ABD83813 modified in a manner described above, which means that those sequences include the above-mentioned modifications 223N and 328 K+ which are not part of the wild-type sequences; or ii. any peptide that has at least 85% sequence homology, more preferably at least about 90% sequence homology, still more preferably at least about 95% sequence homology, even more preferably at least about 97% sequence homology, still even more preferably at least about 98% sequence homology, and even more preferably at least about 99% sequence homology to the polypeptide of i) and that show hemagglutinin inhibition in a standard hemagglutinin inhibition as described above;

iii. any of the peptides of i) or ii) having the amino acids 36T, 36K, 83A, 83T, 83D, 86A, 86V, 120N, 120S, 155N, 155S, 156A, 156T, 189R, 189K, 212K, 212R, 212E, 263A, 263T, or 120N/155N; or iv. any of such peptides of i), ii), or iii) having one or more of the following amino acid clusters selected from the group consisting of:
   a. aa 93-95: GNF
   b. aa 123-125 SDH
   c. aa 128-130: SSG
   d. aa 138-140: GSS
   e. aa 226-228: MDF
   f. aa 270-272: EVE
   g. aa 309-311: NKL; or v. any peptide of i), ii) iii) or iv) having one or more of the following amino acid clusters selected from the group consisting of:
   a. aa 93-95: GNF
   b. aa 128-130: SSG
   c. aa 138-140: GSS Preferably, the H5 protein (1) for use in a method of treating or preventing infections with H5N1 virus of a different clade is recombinantly expressed and/or produced by a baculovirus expression system, preferably in cultured insect cells.

The term "H5 protein (1)" as mentioned herein is thus, in particular, equivalent to the term "recombinant H5 protein" used herein.

Regarding the H5N1 virus of a different clade, as mentioned herein, said H5N1 virus of a different clade is preferably selected from the group consisting of clade 0 H5N1 virus, clade 2 H5N1 virus, clade 3 H5N1 virus, clade 4 H5N1 virus, clade 5 H5N1 virus, clade 6 H5N1 virus, clade 7 H5N1 virus, clade 8 H5N1 virus and clade 9 H5N1 virus.

In a further preferred embodiment of the invention, the H5N1 virus of a different clade is clade 2.2 H5N1 virus or a clade 2.3 H5N1 virus.

In a particular preferred embodiment of the invention, the H5N1 virus of a different clade is a clade 2.2.1 H5N1 virus or a clade 2.3.2 H5N1 virus.

For reasons of clarity, H5 protein of the H5N1 virus of a different clade is termed "H5 protein (2)" hereinafter. Hence, H5 protein (2) as mentioned herein is in particular a H5 protein coded by the genome of a H5N1 of any clade with the exception of clade 1.

In still a further preferred embodiment, the H5N1 virus of a different clade is a H5N1 virus of North African or of Vietnamese origin, wherein said H5N1 virus of North African origin is preferably a H5N1 virus comprising a H5 protein (2) of influenza virus, wherein said H5 protein (2) has
a. the amino acids 113D, 126H, 145(-), 156R, 160F, 167T, and 181N, wherein the modification 145(-) means that amino acid position 145 of H5 is deleted, or
b. the amino acids 87P, 145L, 172T, 201E, 206I, 208K, 254T, 341G and 421K, or
c. the amino acids 145L, 172T, and 254V,
and wherein the numbering of the amino acid positions of the H5 protein (2) refers to the amino acid position as exemplarily given in SEQ ID NO:8;
or wherein said H5 protein (2) consists of or comprises an amino acid sequence which is at least 95%, preferably at least 96%, more preferably at least 97%, still more preferably at least 98%, yet more preferably at least 99%, or in particular preferred 100% homolog with any one of the sequences as set forth in SEQ ID NOs: 9 to 46.

In the context of the invention, said H5 protein (2) according to (a) is a Subclade A protein, and said H5 protein according to (b) or (c) is a Subclade B protein.

Within the context of the invention, it is understood that the term "amino acid" in particular refers to an amino acid residue or, respectively, to an amino acid which has been covalently linked via peptide bonds to two further amino acids or, if the amino acid is N- or C-terminally located in the peptide sequence, to one further amino acid.

In a still more preferred embodiment of the invention, the H5N1 virus of a different clade comprises H5 protein (2) having
a. the amino acids 87L, 113D, 126H, 145(-), 156R, 160F, 167T, and 181N, or
b. the amino acids 87P, 113N, 126R, 145L, 160Y, 172T, 181H, 201E, 206I, 208K, 254T, 341G and 421K, or
c. the amino acids 87L, 113N, 126R, 145L, 156G, 160Y, 172T, 181H, and 254V,
and/or wherein such H5 protein (2) comprises a peptide that comprises:
i. any one of the amino acid sequences of SEQ ID NOs: 9 to 46;
ii. any peptide that has at least 85%, preferably at least 95%, even more preferably at least 96%, even more preferably at least 97%, even more preferably at least 98%, even more preferably at least 99%, most preferably 100% sequence homology to the polypeptide of i) and that comprises hemagglutinin inhibition in a standard hemagglutinin inhibition assay; or
iii. any part of the polypeptides of i) or ii) comprising at least 334 contiguous amino acids of any of such peptides of i) or ii) and wherein any of such peptide comprises hemagglutinin inhibition in a standard hemagglutinin inhibition assay,
and/or wherein such H5 protein (2) consists of or comprises a contiguous amino acid sequence which has at least 95% even more preferably at least 96%, even more preferably at least 97%, even more preferably at least 98%, even more preferably at least 99%, most preferably 100% sequence identity with any one of the sequences as set forth in SEQ ID NOs: 9 to 46.

More particular, the H5N1 virus of a different clade preferably comprises H5 protein (2) which consists of or comprises an amino acid sequence which is at least 95%, preferably at least 96%, more preferably at least 97%, still more preferably at least 98%, yet more preferably at least 99%, or in particular preferred 100% homolog with any one of the sequences as set forth in SEQ ID NOs: 15 or 20, and wherein such H5 protein (2) comprising or consisting of the amino acid sequence set forth in SEQ ID NO:20 are in particular more preferred.

In particular, the present invention is directed to the H5 protein (1) described herein for use in a method of treating or preventing infections a. with Subclade A H5N1 virus of North African origin, namely an infection with a H5N1 virus comprising a H5 protein (2) having the amino acids according to (a) of claim 13 or 14 or comprising a H5 protein according to claim 16 or 17 relating to any one of the sequences as set forth in SEQ ID NOs: 9 to 19, or 42 or 43, or b. with Subclade B H5N1 virus of North African origin, namely an infection with a H5N1 virus comprising a H5 protein having the amino acids according to (b) or (c) of claim 13 or 14 or comprising a H5 protein according to claim 16 or 17 relating to any one of the sequences as set forth in SEQ ID NOs: 20 to 41, or 44 to 46.

According to a further embodiment, the present invention also relates to nucleic acid molecules, which code for any of the H5 proteins (1), as described supra, for use in a method of treating or preventing infections with H5N1 virus of a different clade. Preferably, those nucleic acid molecules are RNA, DNA or copy (c)DNA molecules. Thus, the present invention relates to a nucleic acid molecule, preferably a cDNA molecule coding for a H5 protein or any modified forms of H5 protein, including any deletion, substitution and/or insertion mutant of H5 protein, wherein those H5 proteins having the amino acid 223N and the modification 328K+, wherein numbering of the amino acid positions of the H5 protein refers to the amino acid position as exemplarily given in SEQ ID NO:2 and wherein the modification 328K+ means that at amino acid position 328 of H5 protein a second Lysine (K+) is inserted.

According to a further embodiment, the present invention also relates to a nucleic acid molecule, preferably a cDNA molecule coding for any part of the H5 protein (1), which means encoding for any peptide-fragment which shows antigenic properties in an standard hemagglutinin inhibition assay as described supra, and having at least the amino acid 223N and the modification 328K+, wherein numbering of the amino acid positions of the H5 protein refers to the amino acid position as exemplarily given in SEQ ID NO:2 and wherein the modification 328K+ means that at amino acid position 328 of H5 protein a second Lysine (K+) is inserted. Normally such nucleic acid molecules, which code for an antigenic part of H5 protein, comprise 600, 540, 480, 450, 420, 390, 360, 330 or most preferably 315 contiguous nucleotides of the nucleotide sequence that codes for the H5 protein as mentioned above, modified or non-modified, and which shows antigenic properties in an standard hemagglutinin inhibition assay as described herein.

Further embodiments of antigenic parts of the H5 protein (1) are described supra. It is in the common knowledge of a person skilled in the art to construct any such nucleic acid molecules, preferably cDNA molecules which codes for the antigenic part of the H5 protein as described supra. This also include but is not limited to the construction of nucleic acid molecules, preferably of cDNA molecules, which codes for antigenic parts of the H5 protein as mentioned above including deletion mutants of H5 protein, which comprises:

i. at least 105, 90, 75, 60, 48, 45, 39, 30, 27, or most preferably 24 contiguous amino nucleotides of the nucleotide sequence that surrounds and includes the coding sequence that codes for amino acid 223N; and ii. at least 105, 90, 75, 60, 48, 45, 39, 30, 27, or most preferably 24 contiguous amino nucleotides of the nucleotide sequence that surrounds and includes the coding sequence that codes for modification 328K+, and iii. wherein any of such antigenic part of H5 protein show hemagglutinin inhibition in a standard hemagglutinin inhibition assay as described in Example 2.

Preferably, those surrounding nucleotides of the nucleotides, which code for amino acids 223N and/or 328K+, coding for SEQ ID NO:2 or SEQ ID NO:5.

Furthermore preferred nucleic acid molecules encoding for the H5 protein (1) according to the invention are:

i. any of those mentioned supra encoding for the amino acid 223N and the modification 328K+;

ii. any of those mentioned supra encoding for the amino acid 94N/223N and the modification 328K+;

iii. any nucleic acid molecules of avian origin encoding for the amino acid 223N, and the modification 328K+, wherein avian origin means that the H5 sequence derived from a virus isolate that was originally isolated from poultry infected with avian influenza virus type 5; or iv. any nucleic acid molecules of avian origin encoding for the amino acids 94N/223N and the modification 328K+, wherein avian origin means that the H5 sequence derived from a virus isolate that was originally isolated from poultry infected with avian influenza virus type 5; or.

v. any nucleic acid molecules of avian origin encoding for the amino acids 155N/223N and the modification 328K+, wherein avian origin means that the H5 sequence derived from a virus isolate that was originally isolated from poultry infected with avian influenza virus type 5; or vi. any nucleic acid molecule encoding for H5 protein of avian origin having the amino acid 120N/155N/223N and the modification 328K+, wherein avian origin means that the H5 sequence derived from a virus isolate that was originally isolated from poultry infected with avian influenza virus type 5; or vii. any nucleic acid molecule encoding for H5 protein having the modifications 94N/223N and the modification 328K+; or viii. any nucleic acid molecule encoding for H5 protein having the modifications 94N/155N/223N and the modification 328K+; or;

ix. any nucleic acid molecule encoding for H5 protein having the modifications 94N/120N/155N/223N and the modification 328K+; or x. any nucleic acid molecule encoding for H5 protein having the modifications 223N, the modification 328K+, and one or more of the following amino acid clusters selected from the group consisting of:
  a. aa 93-95: GNF
  b. aa 123-125: SDH
  c. aa 128-130: SSG
  d. aa 138-140: GSS
  e. aa 226-228: MDF
  f. aa 270-272: EVE
  g. aa 309-311: NKL; or xi. any nucleic acid molecule encoding for H5 protein having the amino acid 223N, the modification 328K+, and one or more of the following amino acid clusters selected from the group consisting of:
  a. aa 93-95: GNF
  b. aa 128-130: SSG
  c. aa 138-140: GSS; or xii. any nucleic acid molecule encoding for H5 protein having the amino acid sequence of SEQ ID NO:5.

Furthermore preferred H5 proteins (1) as provided herewith include the H5 proteins as described by Hoffmann et al, *PNAS*, vol. 106, no. 36, pp. 12915-12920 of Sep. 6, 2005, wherein that H5 proteins includes one or more of the modifications as described above, at least the amino acid 223N and the modification 328K+, wherein numbering of the amino acid positions of the H5 protein refers to the amino acid position as exemplarily given in SEQ ID NO:2 and wherein the modification 328K+ means that at amino acid position 328 of H5 protein a second Lysine (K+) is inserted. The disclosure of this reference shall be entirely included herein by reference. Thus according to a further embodiments, the present invention also relates to any nucleic acid molecule, preferably a cDNA molecule coding for any of such proteins described by Hoffmann et al, *PNAS*, vol. 106, no. 36, pp. 12915-12920 of Sep. 6, 2005, wherein that H5 proteins includes one or more of the modifications as described above, at least the amino acid 223N and the modification 328K+, wherein numbering of the amino acid positions of the H5 protein refers to the amino acid position as exemplarily given in SEQ ID NO:2 and wherein the modification 328K+ means that at amino acid position 328 of H5 protein a second Lysine (K+) is inserted.

Methods, of how to introduce any of the above-mentioned modifications within the nucleotide sequence, including the encoding sequence of the H5 protein of an influenza virus, are well known in the art. The genomic sequence of the entire influenza virus can be modified according to the invention, for example according to the methods described in U.S. Pat. No. 6,951,754, with further references.

Furthermore, there may be employed conventional molecular biology, microbiology, and recombinant DNA techniques within the skill of the art to modify a nucleic acid sequence coding for an antigen as described herein. Such techniques are explained fully in the literature. See, e.g., Sambrook et al., *Molecular Cloning: A Laboratory Manual, Second Edition* (1989) Cold Spring Harbor Laboratory Press, Cold Spring Harbor, N.Y.; *DNA Cloning: A Practical Approach, Volumes I and II* (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. 1994).

According to a further embodiment, the present invention also relates to a vector that comprises any of such nucleic acid molecules as described supra. In other words, the present invention relates to a vector, that includes the coding sequence of any such H5 protein (1), or part thereof as described supra. Preferably, said vector is an expression vector, which allows the expression of any such H5 protein (1) or part thereof as described supra. Vectors according to the invention are those which are suitable for the transfection or infection of bacterial, yeast or animal cells, in vitro or in vivo.

Vectors and methods for making and/or using vectors (or recombinants) for expression can be by or analogous to the methods disclosed in: U.S. Pat. Nos. 4,603,112, 4,769,330, 5,174,993, 5,505,941, 5,338,683, 5,494,807, 4,722,848, 5,942,235, 5,364,773, 5,762,938, 5,770,212, 5,942,235, 382, 425, PCT publications WO 94/16716, WO 96/39491, WO 95/30018, Paoletti, "Applications of pox virus vectors to vaccination: An update," PNAS USA 93: 11349-11353, October 1996, Moss, "Genetically engineered poxviruses for recombinant gene expression, vaccination, and safety," PNAS USA 93: 11341-11348, October 1996, Smith et al., U.S. Pat. No. 4,745,051, (recombinant baculovirus), Richardson, C. D. (Editor), Methods in Molecular Biology 39, "Baculovirus Expression Protocols" (1995 Humana Press Inc.), Smith et al., "Production of Human Beta Interferon in Insect Cells Infected with a Baculovirus Expression Vector", Molecular and Cellular Biology, December, 1983, Vol. 3, No. 12, p. 2156-2165; Pennock et al., "Strong and Regulated Expression of *Escherichia coli* B-Galactosidase in Infect Cells with a Baculovirus vector," Molecular and Cellular Biology March 1984, Vol. 4, No. 3, p. 399-406; EPA0 370 573, U.S. application No. 920,197, filed Oct. 16, 1986, EP Patent publication No. 265785, U.S. Pat. No. 4,769,331 (recombinant herpesvirus), Roizman, "The function of herpes simplex virus genes: A primer for genetic engineering of novel vectors," PNAS USA 93:11307-11312, October 1996, Andreansky et al., "The application of genetically engineered herpes simplex viruses to the treatment of experimental brain tumors," PNAS USA 93: 11313-11318, October 1996, Robertson et al. "Epstein-Barr virus vectors for gene delivery to B lymphocytes", PNAS USA 93: 11334-11340, October 1996, Frolov et al., "Alphavirus-based expression vectors: Strategies and applications," PNAS USA 93: 11371-11377, October 1996, Kitson et al., J. Virol. 65, 3068-3075, 1991; U.S. Pat. Nos. 5,591,439, 5,552,143, WO 98/00166, allowed U.S. application Ser. Nos. 08/675, 556, and 08/675,566 both filed Jul. 3, 1996 (recombinant adenovirus), Grunhaus et al., 1992, "Adenovirus as cloning vectors," Seminars in Virology (Vol. 3) p. 237-52, 1993, Ballay et al. EMBO Journal, vol. 4, p. 3861-65, Graham, Tibtech 8, 85-87, April, 1990, Prevec et al., J. Gen Virol. 70, 42434, PCT WO 91/11525, Felgner et al. (1994), J. Biol. Chem. 269, 2550-2561, Science, 259: 1745-49, 1993 and McClements et al., "Immunization with DNA vaccines encoding glycoprotein D or glycoprotein B, alone or in combination, induces protective immunity in animal models of herpes simplex virus-2 disease", PNAS USA 93: 11414-11420, October 1996, and U.S. Pat. Nos. 5,591,639, 5,589, 466, and 5,580,859, as well as WO 90/11092, WO93/19183, WO94/21797, WO95/11307, WO95/20660, Tang et al., Nature and Furth et al. Analytical Biochemistry, relating to DNA expression vectors, inter alia. See also WO 98/33510; Ju et al., Diabetologia, 41: 736-739, 1998 (lentiviral expression system); Sanford et al., U.S. Pat. No. 4,945,050; Fischbachet al. (Intracel), WO 90/01543; Robinson et al., seminars in Immunology vol. 9, pp. 271-283 (1997), (DNA vector systems); Szoka et al., U.S. Pat. No. (method of inserting DNA into living cells); McCormick et al., U.S. Pat. No. 5,677,178 (use of cytopathic viruses); and U.S. Pat. No. 5,928,913 (vectors for gene delivery), as well as other documents cited herein, each of which is incorporated by reference herein.

A viral vector, for instance, selected from pig herpes viruses, such as Aujeszky's disease virus, porcine adenovirus, poxviruses, especially vaccinia virus, avipox virus, canarypox virus, and swinepox virus, as well as DNA vectors (DNA plasmids) are advantageously employed in the practice of the invention.

Methods of Producing the H5 Proteins (1)
According to the Present Invention

According to another aspect, the present invention provides methods of producing and/or recovering high amounts of recombinant H5 protein: i) by permitting infection of susceptible cells in culture with a recombinant viral vector containing H5 DNA coding sequences, wherein H5 protein is expressed by the recombinant viral vector, and ii) thereafter recovering the H5 protein from cell culture. High amounts of H5 protein means, but are not limited to, more than about 20 µg/mL cell culture, preferably more than about 25 µg/mL, even more preferred more than about 30 µg/mL, even more preferred more than about 40 µg/mL, even more preferred more than about 50 µg/mL, even more preferred more than about 60 µg/mL, even more preferred more than about 80 µg/mL, even more preferred more than about 100 µg/mL, even more preferred than about 150 µg/mL, most preferred more than about 190 µg/mL.

According to a preferred embodiment, the H5 protein (1) is recovered by harvesting the whole (i.e. intact) SF+ cells expressing the H5 protein.

Preferred cells are those susceptible for infection with an appropriate recombinant viral vector, containing a H5 DNA and expressing the H5 protein (1). Preferably the cells are insect cells, and more preferably, they include the insect cells sold under the trademark SF+ insect cells (Protein Sciences Corporation, Meriden, Conn.). Preferred cell cultures have a cell count between about $0.3$-$2.0 \times 10^6$ cells/mL, more preferably from about $0.35$-$1.9 \times 10^6$ cells/mL, still more preferably from about $0.4$-$1.8 \times 10^6$ cells/mL, even more preferably from about $0.45$-$1.7 \times 10^6$ cells/mL, and most preferably from about $0.5$-$1.5 \times 10^6$ cells/mL.

Preferred viral vectors include baculovirus such as BaculoGold (BD Biosciences Pharmingen, San Diego, Calif.), in particular provided that the production cells are insect cells. Although the baculovirus expression system is preferred, it is understood by those of skill in the art that other expression systems will work for purposes of the present invention, namely the expression of H5 into the supernatant of a cell culture. Such other expression systems may require the use of a signal sequence in order to cause H5 expression into the media.

Appropriate growth media will also be determinable by those of skill in the art with a preferred growth media being serum-free insect cell media such as Excell 420 (JRH Biosciences, Inc., Lenexa, Kans.) and the like.

The recombinant viral vector containing the H5 DNA sequences has a preferred multiplicity of infection (MOI) of between about 0.03-1.5, more preferably from about 0.05-1.3, still more preferably from about 0.09-1.1, and most preferably from about 0.1-1.0, when used for the infection of the susceptible cells. Preferably the MOIs mentioned above relates to one mL of cell culture fluid. Preferably, the method described herein comprises the infection of $0.35$-$1.9 \times 10^6$ cells/mL, still more preferably of about $0.4$-$1.8 \times 10^6$ cells/mL, even more preferably of about $0.45$-$1.7 \times 10^6$ cells/mL, and most preferably of about $0.5$-$1.5 \times 10^6$ cells/mL with a recombinant viral vector containing a H5 DNA and expressing the H5 protein having a MOI (multiplicity of infection) of between about 0.03-1.5, more preferably from about 0.05-1.3, still more preferably from about 0.09-1.1, and most preferably from about 0.1-1.0.

The infected cells are then incubated over a period of up to ten days, more preferably from about two days to about ten days, still more preferably from about four days to about nine days, and most preferably from about five days to about eight days. Preferred incubation conditions include a temperature between about 22-32° C., more preferably from about 24-30° C., still more preferably from about 25-29° C., even more preferably from about 26-28° C., and most preferably about 27° C. Preferably, the SF+ cells are observed following inoculation for characteristic baculovirus-induced changes. Such observation may include monitoring cell density trends and the decrease in viability during the post-infection period. It was found that peak viral titer is observed 3-5 days after infection and peak H5 protein expression in the cells is obtained between days 5 and 8, and/or when cell viability decreases to less than 10%.

Thus, one aspect of the present invention provides a method of producing and/or recovering recombinant H5 protein, preferably in amounts described above, by i) permitting infection of a number of susceptible cells (see above) in culture with a recombinant viral vector with a MOI as defined above, ii) expressing G5 protein by the recombinant viral vector, and iii) thereafter recovering the H5 protein from the cells obtained between days 5 and 8 after infection and/or cell viability decreases to less then 10%. Preferably, the recombinant viral vector is a recombinant baculovirus containing H5 DNA coding sequences and the cells are SF+ cells. Additionally, it is preferred that the culture be periodically examined for macroscopic and microscopic evidence of contamination or for atypical changes in cell morphology during the post-infection period. Any culture exhibiting any contamination should be discarded.

For recovery of H5 protein (1) that will be used in an immunogenic or immunological composition such as a vaccine, the inclusion of an inactivation step is preferred in order to inactivate the viral vector.

An "immunogenic or immunological composition" refers to a composition of matter that comprises at least one antigen which elicits an immunological response in the host of a cellular and/or antibody-mediated immune response to the composition or vaccine of interest. Usually, an "immunological response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

As used herein, "vaccine" refers to that term as it is used by those of skill in the art. More particularly, "vaccine" refers to an immunogenic composition that, when administered to an animal in need thereof, results in a reduction in the incidence of or severity of clinical signs of influenza infection up to an including the complete prevention of such clinical signs. Preferably, the reduction in incidence or severity is at least 10%, more preferably at least 20%, still more preferably at least 30%, even more preferably at least 40%, more preferably at least 50%, still more preferably at least 60%, even more preferably at least 70%, more preferably at least 80%, still more preferably at least 90%, even more preferably at least 95%, and most preferably 100% in comparison to an animal or group of animals that did not receive the compositions of the present invention but that were exposed to infectious levels of influenza virus that would normally result in influenza infection resulting in exhibiting clinical signs.

Thus, the present invention also relates to a method of producing and/or recovering recombinant H5 protein, preferably in amounts described above, by i) permitting infection of a number of susceptible cells (see above) in culture with a recombinant viral vector with a MOI as defined above, ii) expressing H5 protein by the recombinant viral vector, iii) recovering the H5 expressed in cells obtained between days 5 and 8 after infection and/or cell viability decreases to less then 10%, and iv) inactivating the recombinant viral vector.

Preferably, this inactivation is done either just before or just after the filtration step, with after the filtration step being the preferred time for inactivation. Any conventional inactivation method can be used for purposes of the present invention. Thus, inactivation can be performed by chemical and/or physical treatments. In preferred forms, the volume of harvest fluids is determined and the temperature is brought to between about 32-42° C., more preferably between about 34-40° C., and most preferably between about 35-39° C. Preferred inactivation methods include the addition of cyclized binary ethylenimine (BEI), preferably in a concentration of about 1 to about 20 mM, preferably of about 2 to about 10 mM, still more preferably of about 2 to about 8 mM, still more preferably of about 3 to about 7 mM, most preferably of about 5 mM. For example the inactivation includes the addition of a solution of 2-bromoethyl-eneamine hydrobromide, preferably of about 0.4M, which has been cyclized to 0.2M binary ethylenimine (BEI) in 0.3N NaOH, to the fluids to give a final concentration of about 5 mM BEI. Preferably, the fluids are then stirred continuously for 72-96 hours and the inactivated harvest fluids can be stored frozen at −40° C. or below or between about 1-7° C. After inactivation is completed a sodium thiosulfate solution, preferably at 1.0M is added to neutralize any residual BEI. Preferably, the sodium thiosulfate is added in equivalent amount as compared to the BEI added prior to for inactivation. For example, in the event BEI is added to a final concentration of 5 mM, a 1.0M sodium thiosulfate solution is added to give a final minimum concentration of 5 mM to neutralize any residual BEI.

Thus, one further aspect of the present invention relates to a method of producing recombinant H5 protein, preferably in amounts described above, by i) permitting infection of a number of susceptible cells (see above) in culture with a recombinant viral vector with a MOI as defined above, ii) expressing H5 protein by the recombinant viral vector, iii) recovering the H5 expressed in the cells obtained between days 5 and 8 after infection and/or cell viability decreases to less then 10%, and iv) inactivating the recombinant viral vector. Preferably, the recombinant viral vector is a baculovirus containing H5 DNA coding sequences and the cells are SF+ cells. Preferred inactivation steps are those described above. Preferably, inactivation is performed between about 35-39° C. and in the presence of 2 to 8 mM BEI, still more preferred in the presence of about 5 mM BEI.

According to one further aspect of the present invention, the method described above also includes a neutralization step after step iv). This step v) comprises adding of an equivalent amount of an agent that neutralizes the inactivation agent within the solution. Preferably, if the inactivation agent is BEI, addition of sodium thiosulfate to an equivalent amount is preferred. Thus, according to a further aspect, step v) comprises adding of a sodium thiosulfate solution to a final concentration of about 1 to about 20 mM, preferably of about 2 to about 10 mM, still more preferably of about 2 to about 8 mM, still more preferably of about 3 to about 7 mM most preferably of about 5 mM, when the inactivation agent is BEI.

In preferred forms and especially in forms that will use the recombinant H5 protein in an immunogenic composition such as a vaccine, each lot of harvested H5 protein will be tested for inactivation by passage in the anchorage dependent, baculovirus susceptible insect cells, such as Sf9 cells. In a preferred form of this testing, 150 cm² of appropriate cell culture monolayer is inoculated with 1.0 mL of inactivated H5 fluids and maintained at 25-29° C. for 14 days with at least two passages. At the end of the maintenance period, the cell monolayers are examined for cytopathogenic effect (CPE) typical of H5 baculovirus. Preferably, positive virus controls are also used. Such controls can consist of one culture of Sf9 cells inoculated with a non-inactivated reference H5 baculovirus and one flask of Sf9 cells that remain non-inoculated. After incubation and passage, the absence of virus-infected cells in the BEI treated viral fluids would constitute a satisfactory inactivation test. The control cells inoculated with the reference virus should exhibit CPE typical of H5 baculovirus and the non-inoculated flask should not exhibit any evidence of H5 baculovirus CPE. Alternatively, at the end of the maintenance period, the supernatant samples could be collected and inoculated onto a Sf9 96 well plate, which has been loaded with Sf9 cells, and then maintained at 25-29° C. for 5-6 days. The plate is then fixed and stained with anti-H5 antibody conjugated to FITC or any labeled antibody directed to baculovirus specific proteins (i.e. gp64). The absence of CPE, H5 expression, or expression of baculovirus specific proteins (i.e. gp64) in the BEI treated viral fluids constitutes a satisfactory inactivation test. The control cells inoculated with the reference virus should exhibit CPE and IFA activity and the non-inoculated flask should not exhibit any evidence of H5 baculovirus CPE and contain no IFA activity.

Thus a further aspect described herein, relates to an inactivation test for determining the effectiveness of the inactivation of the recombination viral vector expressing H5 protein (1), comprises the steps: i) contacting at least a portion of the culture fluid containing the recombinant viral vector with an inactivating agent, preferably as described above, ii) adding a neutralization agent to neutralize the inactivation agent, preferably as described above, and iii) determining the residual infectivity by the assays as described above.

After inactivation, the relative amount of recombinant H5 protein in a sample can be determined in a number of ways. Preferred methods of quantitation include SDS-PAGE densitometry, ELISA, and animal vaccination studies that correlate known quantities of vaccine with clinical outcomes (serology, etc.). When SDS-PAGE is utilized for quantitation, the sample material containing an unknown amount of recombinant H5 protein is run on a gel, together with samples that contain different known amounts of recombinant H5 protein. A standard curve can then be produced based on the known samples and the amount of recombinant H5 in the unknown sample can be determined by comparison with this standard curve. Because ELISAs are generally recognized as the industry standard for antigen quantitation, they are preferred for quantitation.

Vaccines Comprising H5 Proteins (1) or Nucleic Acid Molecules or Vectors Coding for Those The invention further provides a combination of
a. (a) the H5 protein (1) described herein and
b. (b) an inactivated Newcastle disease virus for use in a method of treating or preventing infections with H5N1 virus of a different clade, in particular for use in any method of treating or preventing infections with H5N1 virus of a different clade as described herein.

Said combination is also termed "the combination described herein" hereinafter.

According to the invention it is understood that the combination described herein is preferably included in a multivalent combination vaccine or the combination described herein is in particular directed to a combined vaccination, more particular to an administration of the H5 protein (1) described herein and of the inactivated Newcastle disease virus within a maximum of 24 hours to an animal, in particular poultry, or human being in need thereof.

Preferably, the inactivated Newcastle disease virus is an inactivated whole Newcastle disease virion.

In another preferred embodiment, the inactivated Newcastle disease virus is an inactivated Newcastle disease virus obtained by inactivation of a Newcastle disease virus comprising a RNA polynucleotide having at least 70%, preferably at least 80%, more preferably at least 90%, still more preferably at least 95% or in particular 100% sequence identity with a RNA copy of the polynucleotide set forth in SEQ ID NO: 51 (cDNA sequence of LaSota strain virus), which has been inactivated.

In particular, the inactivated Newcastle disease virus is an inactivated Newcastle disease LaSota strain virus.

In one preferred embodiment the inactivated Newcastle Disease Virus is a Newcastle Disease Virus which has been inactivated with a reagent selected from the group consisting of Formaldehyde, binary ethyleneimine (BEI), Beta-Propio-Lactone (BPL), and combinations thereof.

The amount of inactivated Newcastle disease virus in the combination described herein is preferably between $10^2$ and $10^{10}$ equivalents of egg infectious doses (EID50), preferably between $10^6$ and $10^9$ EID50, in particular preferably between $10^7$ and $10^9$ EID50. The amount of the H5 protein (1) in the combination described herein is preferably the same as mentioned hereinafter.

The amount of the H5 protein (1) according to the invention is preferably between 10 and 1000 Hemagglutination units (HAU's) per dose, more preferably between 50 and 950 HAU's per dose, even more preferably between 100 and 900 HAU's per dose, even more preferably between 200 and 800 HAU's per dose, even more preferably between 300 and 700 HAU's per dose, still more preferably between 300 and 500 HAU's per dose.

According to a further aspect, the present invention relates to vaccines or pharmaceutical compositions in general, that comprises,
i. one or more of the H5 proteins (1) as described herein or the combination described herein;
ii. one or more of the nucleic acid molecules as described herein, coding for any such H5 proteins (1); and/or
iii. one or more of the vectors as described herein, including any such nucleic acid molecules and coding for any such H5 proteins (1) as described herein; and
iv. a pharmaceutical acceptable carrier and/or excipient.

The term "pharmaceutical composition" "Pharmaceutical/vaccine composition" as described herein, includes but is not limited to, vaccines for the reduction or prevention of an infection or to a composition of matter for the treatment and lessening of an infection.

The preparation of nucleic acid based vaccines, preferably cDNA vaccines, coding for influenza hemagglutinin are described for example in Deck et al, *Vaccine* 1997; 15 (1):71-78; Ulmer et al., *Science* 1993; 259:1745-1749; Ulmer et al., *Vaccine* 1994; 12 (16):1541-1544. Any of those methods can be used for the production of nucleic acid based vaccines, preferably cDNA vaccines, coding for an influenza H5 protein as described herein.

Moreover, a vaccine, which comprises H5 protein (1) or parts thereof as described herein, can be produced by conventional approaches, e.g. by recombinant expression techniques or by biochemical purification and separation techniques. Recombinant expression techniques, including the expression in insect cells are well known in the art, and described for example in Sambrook et al., *Molecular Cloning: A Laboratory Manual, Second Edition* (1989) Cold Spring Harbor Laboratory Press, Cold Spring Harbor, N.Y.; *DNA Cloning: A Practical Approach, Volumes I and II* (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. 1994). Further examples of well established recombinant expression systems are bacterial expression systems such as *E. coli* or *B. subtilis*, yeast-based expression systems such as *S. cerevisiae* or *S. pombe*, or mammalian cell expression systems such as the BHK-, CHO- and/or NSO-based expression systems. Such systems are well known in the art and generally available, e.g. commercially through Clontech Laboratories, Inc. 4030 Fabian Way, Palo Alto, Calif. 94303-4607, USA. Further expression strategies are for example described in Liischow et al., *Vaccine no.* 19 (2001), pp. 4249-4259, or Veit et al., *PNAS* vol. 103 (2006), pp. 8197-8202. Furthermore, recombinant adeno-associated virus systems are well established and for example described in U.S. Pat. No. 5,436,146 or WO200203872 with further references. Moreover, vaccinia (pox) virus based expression systems, for example as described in U.S. Pat. No. 6,265,183 with further references, are also well established and suitable to produce recombinant antigen(s), antigenic composition(s) as used according to the invention. Further suitable expression systems make use of recombinant popova viruses, such as SV40, fowl pox virus, pseudorabies viruses and retroviruses.

The relevant pharmaceutical/vaccine compositions as described herein, can also comprise inactivated virus which comprises H5 protein (1) as described herein, an apathogenic version of a live virus comprising H5 protein (1) as described herein, preparation and/or fragments of a virus, wherein said preparation and/or fragment comprise the H5 protein (1) as described herein.

The skilled person knows additional components which may be comprised in said compositions/vaccines together with antigen (see for example, *Remington's Pharmaceutical Sciences*. (1990). 18th ed. Mack Publ., Easton). The expert may use known injectable, physiologically acceptable sterile solutions. For preparing a ready-to-use solution, aqueous isotonic solutions, such as e.g. saline or corresponding plasma protein solutions, are readily available. The pharmaceutical composition/vaccine may be present as lyophylisates or dry preparations, which can be reconstituted with a known injectable solution directly before use under sterile conditions, e.g. as a kit of parts.

In addition the pharmaceutical/vaccine compositions of the present invention can include one or more veterinary-acceptable carriers. As used herein, "a veterinary-acceptable carrier" includes but is not limited to any and all solvents, dispersion media, coatings, adjuvants, stabilizing agents, diluents, preservatives, antibacterial and antifungal agents, isotonic agents, adsorption delaying agents, and the like.

Diluents can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

A preservative as used herein, refers to an anti-microbiological active agent, such as for example Gentamycin, Merthiolate, and the like. In particular adding of a preservative is most preferred for the preparation of a multi-dose composition. Those anti-microbiological active agents are added in concentrations effective to prevent the composition of interest for any microbiological contamination or for inhibition of any microbiological growth within the composition of interest.

"Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion.

The emulsion can be based in particular on light liquid paraffin oil (European Pharmacopoeia type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed.Stewart-Tull, D. E. S.). John Wiley and Sons, NY, pp 51-94 (1995) and Todd et al., Vaccine 15:564-570 (1997). Examples for suitable oil-in water emulsions are Emulsigen-based adjuvants, such as EMULSIGEN®, EMULSIGEN-D®, EMULSIGEN-P®, EMULSIGEN-75® (MVP Laboratories, Inc. Omaha, Nebr., USA). It has been surprisingly found, that pharmaceutical/vaccine compositions that comprise H5 protein, preferably recombinant H5 protein as described herein, have been effectively adjuvanted with oil-in water emulsions, preferably with such Emulsigen-based adjuvants, more preferably with EMULSIGEN® and EMULSIGEN-D®.

Moreover, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars orpolyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of Carbopol 971P. Among the copolymers of maleic anhydride and alkenyl derivative, the copolymers EMA (Monsanto) which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from E. coli (recombinant or otherwise), cholera toxin, or muramyl dipeptide among many others.

Preferably, the adjuvant is added in an amount of about 100 μg to about 10 mg per dose. Even more preferred the adjuvant is added in an amount of about 100 μg to about 10 mg per dose. Even more preferred the adjuvant is added in an amount of about 500 μg to about 5 mg per dose. Even more preferred the adjuvant is added in an amount of about 750 μg to about 2.5 mg per dose. Most preferred the adjuvant is added in an amount of about 1 mg per dose.

The pharmaceutical/vaccine compositions, can further include one or more other immunomodulatory agents such as, e. g., interleukins, interferons, or other cytokines. The pharmaceutical/vaccine compositions can also include Gentamicin and Merthiolate. While the amounts and concentrations of adjuvants and additives useful in the context of the present invention can readily be determined by the skilled artisan, the present invention contemplates compositions comprising from about 50 μg to about 2000 μg of adjuvant and preferably about 250 ug/1 ml dose of the vaccine composition. In another preferred embodiment, the present invention contemplates vaccine compositions comprising from about 1 ug/ml to about 60 μg/ml of antibiotics, and more preferably less than about 30 μg/ml of antibiotics.

Thus, according to a further embodiment, the present invention also relates to a pharmaceutical/vaccine composition comprising i. a therapeutically effective amount of any one of the H5 proteins of influenza virus as described herein, wherein the H5 protein having the amino acid 223N and the modification 328K+, wherein numbering of the amino acid positions of the H5 protein refers to the amino acid position as exemplarily given in SEQ ID NO:2 and wherein the modification 328K+ means that at amino acid position 328 of H5 protein a second Lysine (K+) is inserted; and ii. a pharmaceutically acceptable adjuvants as described above.

Preferably, the adjuvant is selected from the group consisting of:

a. EMULSIGEN®, a oil-in-water emulsion (o/w);
b. EMULSIGEN-D®, a oil-in-water (o/w) with dimethyldioctadecylammonum bromide (DDA);
c. a Polygen, a copolymer
d. EMULSIGEN-P®, a oil-in-water (o/w) with a proprietary immunostimulant
e. Carbigen is a cross-linked polymer
f. EMULSIGEN-75®, a double adjuvants comprise of a oil-in-water (o/w) with a cross-linked polymer
g. ISA 70 is a water-in-oil (w/o)

Most preferably, the adjuvants is a oil-in-water emulsion such as an emulsigen-based adjuvant selected from the group consisting of EMULSIGEN®, EMULSIGEN-D®, EMULSIGEN-P®, EMULSIGEN-75®, EMULSIGEN® and EMULSIGEN-P®. Most preferably EMULSIGEN® and EMULSIGEN-P® are used in the formulation of the current invention.

According to a further aspect, the pharmaceutical/vaccine compositions as provided herewith, comprise one or more antigen. Preferably, that further antigen is an antigen of a poultry or mammalian pathogen. According to a further embodiments, that additional antigen is an further influenza antigen such as hemagglutinin H5, H7, H9, or any other hemagglutinin of influenza virus, wherein the H5 is preferably a H5 protein of a H5N1 virus of a clade different than clade 1, in particular of a H5N1 virus of North African origin, such as the H5 protein (2) described herein. The additional antigen(s) can be added in a purified form, as part of an antigenic preparation, in the form of a killed microorganism or in the form of a modified live microorganism.

The term "antigen", as used herein means, but is not limited to, peptides, polypeptides, glycopeptides, or polysaccharides which are capable of specifically interacting with an antigen recognition molecule of the immune system, such as an immunoglobulin (antibody) or T cell antigen receptor in order to elicit, activate or stimulate an immune response directed to said antigen in a host to which said antigen is administered. The term "antigen" also refers to nucleic acid molecules, preferably DNA- or RNA-molecules, each of which codes for and express a peptide, polypeptide, or glycopeptide that is capable of specifically interacting with an antigen recognition molecule of the immune system, such as an immunoglobulin (antibody) or T cell antigen receptor in order to elicit, activate or stimulate an immune response against the antigen that is coded by the nucleic acid molecule. The antigen used for the preparation of the pharmaceutical composition which is used according to the invention is a microorganism or an antigenic part and/or preparation of said microorganism. In this connection, the term "immunization", as used herein, means but is not limited to, any cause or enhancement of an immune response. The term "immune response" is already described supra.

Administration strategies for influenza vaccines are well known in the art. Mucosal vaccination strategies for inactivated and attenuated virus vaccines are contemplated. While the mucosa can be targeted by local delivery of a vaccine, various strategies have been employed to deliver immunogenic proteins to the mucosa.

In a specific embodiment, the vaccine can be administered in an admixture with, or as a conjugate or chimeric fusion protein with, cholera toxin, such as cholera toxin B or a cholera toxin A/B chimera (Hajishengallis, *J Immunol.*, 154:4322-32, 1995; Jobling and Holmes, *Infect Immun.*, 60:4915-24, 1992). Mucosal vaccines based on use of the cholera toxin B subunit have been described (Lebens and Holmgren, *Dev Biol Stand* 82:215-27, 1994). In another embodiment, an admixture with heat labile enterotoxin (LT) can be prepared for mucosal vaccination.

Other mucosal immunization strategies include encapsulating the virus in microcapsules (U.S. Pat. Nos. 5,075,109, 5,820,883, and 5,853,763) and using an immunopotentiating membranous carrier (WO 98/0558). Immunogenicity of orally administered immunogens can be enhanced by using red blood cells (rbc) or rbc ghosts (U.S. Pat. No. 5,643,577), or by using blue tongue antigen (U.S. Pat. No. 5,690,938).

According to another aspect, the present invention relates to a method for preparing a pharmaceutical/vaccine composition as described above, preferably a method for producing a vaccine which comprises a recombinant, baculovirus expressed H5 protein as described supra. Generally, this method includes the steps of transfecting a construct into a virus, wherein the construct comprises i) recombinant H5 cDNA as described herein, ii) infecting cells in growth media with the transfected virus, iii) causing the virus to express the recombinant H5 protein as described herein iv) recovering the expressed H5 protein from the culture v) and preparing the composition by blending the expressed H5 protein with a suitable adjuvant and/or other pharmaceutically acceptable carrier.

Preferred adjuvants are those described above. Thus according to a further aspect, the method for preparing an antigenic composition, such as for example a vaccine, for invoking an immune response against influenza infections comprises i) preparing and recovering H5 protein, and ii) admixing this with a suitable adjuvants.

In addition, the vaccine composition of the present invention can also include diluents, isotonic agents, stabilizers, an/or preservatives. Diluents can include water, saline, dextrose, ethanol, glycerol, and the like. Isotonic agents can include anorganic or organic salts, e.g. sodium chloride, dextrose, mannitol, sorbitol, and lactose, saccharides, trehalose, mannitol, saccharose among others. Stabilizers include albumin and alkali salts of ethylendiamintetracetic acid, among others. Suitable adjuvants, are those described above.

Medicinal Use of Any of Such H5 Proteins (1), Nucleic Acid Molecules, Vectors, Vaccines, and Combinations Described Herein The H5 proteins (1) as provided herewith, the nucleic acid molecules coding for any such H5 proteins (1), the vectors comprising any such nucleic acid molecules coding for any such H5 proteins (1) as described herein, and any pharmaceutical/vaccine composition comprising any of such H5 protein (1), nucleic acid molecule or vector or the combination described herein can be used as a medicine, preferably for the treatment and prophylaxis of infections, caused by influenza virus, most preferably by influenza A virus. The H5 proteins (1) as provided herewith, the nucleic acid molecules encoding for any such H5 proteins, the vectors comprising any such nucleic acid molecules encoding for any such H5 proteins (1) as described herein, and any pharmaceutical/vaccine composition comprising any of such H5 protein (1), nucleic acid molecule or vector, as described herein, or the combination described herein can be used for the treatment or prophylaxis of human beings as well as in veterinary medicine. When used in veterinary medicine, the treatment of poultry, preferably bird, chicken, duck, turkey and the like as well as mammals, preferably pigs, cattle, horses, seals, camels, dogs, cats, hamsters, mice and the like, is preferred.

In terms of the present invention, "prophylaxis" refers to the reduction in the incidence of or severity of clinical signs of influenza infection up to an including the complete prevention of such clinical signs. Preferably, the reduction in incidence or severity is at least 10%, more preferably at least 20%, still more preferably at least 30%, even more preferably at least 40%, more preferably at least 50%, still more preferably at least 60%, even more preferably at least 70%, more preferably at least 80%, still more preferably at least 90%, even more preferably at least 95%, and most preferably 100% in comparison to an animal or group of animals that did not receive the compositions of the present invention but that were exposed to infectious levels of influenza virus that would normally result in influenza infection resulting in exhibiting clinical signs.

Thus, according to another aspect the present invention relates to the use of H5 proteins (1) as provided herewith, the nucleic acid molecules encoding for any such H5 proteins (1), the vectors comprising any such nucleic acid molecules encoding for any such H5 proteins (1) as described herein and any pharmaceutical/vaccine compositions comprising any of such H5 protein (1), nucleic acid molecule or vector as described herein or the combination described herein, can be used as a medicine, preferably as a medicine for human beings and/or as veterinary medicine, preferably for poultry, in particular for chicken.

Moreover, H5 proteins (1) as provided herewith, the nucleic acid molecules coding for any such H5 proteins (1), the vectors comprising any such nucleic acid molecules coding for any such H5 protein (1), as described herein, or the combination described herein can be used for the preparation of a pharmaceutical composition, as described herein, preferably of a single-shot vaccine or a one dose vaccine, for the prophylaxis or treatment of infections caused by H5N1 virus of a clade other than clade 1, wherein said H5N1 virus of a clade other than clade 1 is preferably the H5N1 virus of a different clade as described herein. As mentioned above, those pharmaceutical compositions/vaccine compositions can be used for the treatment and/or prophylaxis of human beings as well as for the treatment and/or prophylaxis of animals, such as poultry, preferably bird, chicken, duck, turkey and the like as well as mammals, preferably pigs, cattle, horses, seals, camels, dogs, cats, hamsters, mice and the like.

According to a further aspect, the present invention also relates to a method for the treatment or prophylaxis of influenza virus infections caused by H5N1 virus of a clade other than clade 1, wherein said H5N1 virus of a clade other than clade 1 is preferably the H5N1 virus of a different clade as described herein, wherein the method comprising administration of a therapeutically effective amount of the H5 protein (1) as described herein or of the combination described herein, to a subject in need of such a treatment. Moreover, the present invention also relates to a method for the treatment or prophylaxis of influenza virus infections caused by H5N1 virus of a clade other than clade 1, wherein said H5N1 virus of a clade other than clade 1 is preferably the H5N1 virus of a different clade as described herein, wherein the method comprising administration of a therapeutically effective amount of any H5 nucleic acid molecule or vector as described herein, that codes for any H5 protein (1) as described herein, to a subject in need of such a treatment. Furthermore, the present invention also relates to a method for the treatment or prophylaxis of influenza virus infections caused by H5N1 virus of a clade other than clade 1, wherein said H5N1 virus of a clade other than clade 1 is preferably the H5N1 virus of a different clade described herein, wherein the method comprising administration of a therapeutically effective amount of the vaccine comprising any such H5 protein (1), nucleic acid molecule or vector, as described herein, to a subject in need of such a treatment. The subject in need thereof can be a human being as well as an animal, preferably poultry, even more preferably bird, chicken, duck, turkey or a mammal, preferably pig, cattle, horse, seal, camel, dog, cat, hamster, mouse and the like.

Preferably, the administration, as described herein, is a single-shot administration or a one dose administration.

Preferably, when chicken are vaccinated, the H5 protein as described herein can be used for vaccination at day 1 of age or later, e.g. at day 10, or at day 1 to 10, or at day 10 or later.

Preferably the influenza infection that can be treated by the administration of any H5 protein (1), the nucleic acid molecule or vector encoding for any such H5 protein, or any pharmaceutical/vaccine compositions as described herein, is caused by H5N1 virus of a clade other than clade 1, wherein said H5N1 virus of a clade other than clade 1 is preferably the H5N1 virus of a different clade as described herein and, as the case may be, also in combination with another avian, swine or human influenza virus or any combination or hybrid thereof.

A further advantage of the present invention is that it benefits a "DIVA" (Differentiation of Infected and Vaccinated Animals) concept with specific Elisa Kits for differentiating between vaccinated human beings or animals and human beings or animals infected with H5N1 virus.

According to another aspect, the present invention relates to a kit of parts, that comprises i) any of such H5 protein (1) as described herein, the nucleic acid molecule or vector encoding for any such H5 protein, or any pharmaceutical/vaccine composition comprising any of such H5 protein, nucleic acid molecule or vector as described herein, and ii) a package leaflet indicating the use of such H5 protein, nucleic acid molecule, vector or vaccine for the treatment or prophylaxis of infections caused by H5N1 virus of a clade other than clade 1, wherein said H5N1 virus of a clade other than clade 1 is preferably the H5N1 virus of a different clade as described herein. When chicken are vaccinated, the H5 protein (1) as described herein can be used for vaccination at day 1 on age or later.

It is thus understood that the kit of parts as mentioned herein is for the use, or is used, respectively, for the treatment or prophylaxis of infections caused by H5N1 virus of a clade other than clade 1, wherein said H5N1 virus of a clade other than clade 1 is preferably the H5N1 virus of a different clade as described herein.

According to a further embodiment, that kit in parts comprises at least one further antigen of a poultry or mammalian pathogen and the information indication the medicinal, human or veterinary use of that additional antigen, in particular the further antigen as mentioned above.

The invention further provides a method for reducing viral shedding in a subject, comprising administering the H5 protein (1) described herein or the combination as described herein to a subject infected with or at risk of a viral infection with H5N1 virus of a clade other than clade 1, wherein said H5N1 virus of a clade other than clade 1 is preferably the H5N1 virus of a different clade as described herein.

The invention also relates to the H5 protein (1) described herein or the combination as described herein for use in a method for reducing viral shedding in a subject, wherein said H5 protein (1) or said combination is to be administered to a subject infected with or at risk of a viral infection with H5N1 virus of a clade other than clade 1, and wherein said H5N1 virus of a clade other than clade 1 is preferably the H5N1 virus of a different clade as described herein.

Also, the invention provides the use of the H5 protein (1) described herein or of the combination as described herein for the preparation of a medicament for reducing viral shedding in a subject infected with or at risk of a viral infection with H5N1 virus of a clade other than clade 1, wherein said H5N1 virus of a clade other than clade 1 is preferably the H5N1 virus of a different clade as described herein.

Preferably, the H5 protein (1) according to the invention, the combination described herein, the vaccine as described herein or the kit mentioned herein is for use as a single-shot vaccine or in a one-dose vaccination.

EXAMPLES

The following examples set forth preferred materials and procedures in accordance with the present invention. It is to be understood, however, that these examples are provided by way of illustration only, and nothing therein should be deemed a limitation upon the overall scope of the invention.

Example 1

Construction of a Recombinant Baculoviruses Coding for and Expressing HA H5 Antigens The recombinant baculovirus containing the H5 HA antigen was generated as follows: the coding sequences of the H5 HA (SEQ ID NO:3) was chemically synthesized and subcloned into the transfer vector pVL1392 (BD Biosciences Pharmingen, San Diego, Calif.). The H5 HA MutK+ (SEQ ID NO:5) was generated by using oligonucleotide primers and the QuikChange® Site-Directed Mutagenesis Kit (Stratagene, La Jolla, Calif.) and subcloned into the transfer vector pVL1392 (BD Biosciences Pharmingen, San Diego, Calif.). The pVL1392 plasmids containing the genes coding for H5 HA antigen (SEQ ID NO:3) and H5 HA MutK+ (SEQ ID NO:5) were then co-transfected with DiamondBac® (Sigma) baculovirus DNA into Sf9 insect cells (BD Biosciences Pharmingen) to generate the recombinant baculovirus containing the genes H5 HA coding for SEQ ID NO:3 and H5 HA mutK+ coding for SEQ ID NO:5. The recombinant baculoviruses containing the genes coding for H5 HA (SEQ ID NO:3) and H5 HA MutK+ (SEQ ID NO:5) were plaque-purified and Master Seed Viruses (MSVs) were propagated on the SF+ cell line, aliquoted, and stored at −70° C. Insect cells infected with H5 HA baculoviruses ás described above to generate MSV or Working Seed Viruses express H5 HA antigen (SEQ ID NO:3) and H5 HA MutK+ (SEQ ID NO:5) antigen as detected by polyclonal serum or monoclonal antibodies in an indirect fluorescent antibody assay or Western blot.

After being seeded with the appropriate amounts of recombinant baculoviruses (H5 HA and H5 HA MutK+, respectively), spinner flasks containing SF+ cells (Protein Sciences, Inc., Meriden, Conn.) were then incubated at 27±2° C. for 7 days and with stirring 100 rpm during that time. The flasks used ventilated caps to allow for air flow. The crude whole cell culture containing baculovirus infected SF+ cells and the cell culture supernatents of each culture were harvested.

Example 2

Preparation of Pharmaceutical Compositions (Vaccines) Comprising HA H5 Antigens The crude whole cell H5 HA protein and H5 HA Mutk+ protein expressed in insect cells by baculovirus-based expression system were harvested. Baculoviruses were inactivated in the presence of 5 mM cyclized binary ethylenimine (BEI) (final concentration) between about 32 and 39° C. for 72 to 96 hours. After inactivation is completed, a 0.3 M sodium thiosulfate solution was added to a final concentration of 5 mM to neutralize any residual BEI. After neutralization, various adjuvants were added and the following vaccine/pharmaceutical compositions were generated.

Vaccines

| | |
|---|---|
| Generic product name | 501 |
| Antigen | Crude whole-cell H5 HA protein expressed in insect cells by a baculovirus-based expression system. |
| Formulation | An experimental vaccine comprised of cultured insect cells and supernatant expressing recombinant H5 HA. The vaccine was adjuvanted with Emulsigen. |
| Generic product name | 502 |
| Antigen | Crude whole-cell H5 HA protein expressed in insect cells by a baculovirus-based expression system. |
| Formulation | An experimental vaccine comprised of cultured insect cells and supernatant expressing recombinant H5 HA. The vaccine was adjuvanted with Emulsigen-D. |
| Generic product name | 503 |
| Antigen | Crude whole-cell H5 HA protein expressed in insect cells by a baculovirus-based expression system. |
| Formulation | An experimental vaccine comprised of cultured insect cells and supernatant expressing recombinant H5 HA. The vaccine was adjuvanted with Polygen. |
| Generic product name | 504 |
| Antigen | Crude whole-cell H5 HA protein expressed in insect cells by a baculovirus-based expression system. |
| Formulation | An experimental vaccine comprised of cultured insect cells and supernatant expressing recombinant H5 HA. The vaccine was adjuvanted with Emulsigen-P. |
| Generic product name | 505 |
| Antigen | Crude whole-cell H5 HA protein expressed in insect cells by a baculovirus-based expression system. |
| Formulation | An experimental vaccine comprised of cultured insect cells and supernatant expressing recombinant H5 HA. The vaccine was adjuvanted with Carbigen. |
| Generic product name | 506 |
| Antigen | Crude whole-cell H5 HA protein expressed in insect cells by a baculovirus-based expression system. |
| Formulation | An experimental vaccine comprised of cultured insect cells and supernatant expressing recombinant H5 HA. The vaccine was adjuvanted with Emulsigen-75. |
| Generic product name | 507 |
| Antigen | Crude whole-cell H5 HA protein expressed in insect cells by a baculovirus-based expression system. |
| Formulation | An experimental vaccine comprised of cultured insect cells and supernatant expressing recombinant H5 HA. The vaccine was adjuvanted with ISA 70. |
| Generic product name | 508 |
| Antigen | Crude whole-cell H5 HA mutK+ protein expressed in insect cells by a baculovirus-based expression system. |
| Formulation | An experimental vaccine comprised of cultured insect cells and supernatant expressing recombinant H5 HA. The vaccine was adjuvanted with Emulsigen. |
| Generic product name | 509 |
| Antigen | Crude whole-cell H5 HA mutK+ protein expressed in insect cells by a baculovirus-based expression system. |
| Formulation | An experimental vaccine comprised of cultured insect cells and supernatant expressing recombinant H5 HA. The vaccine was adjuvanted with Emulsigen-D. |

-continued

| | |
|---|---|
| Generic product name | 510 |
| Antigen | Crude whole-cell H5 HA mutK+ protein expressed in insect cells by a baculovirus-based expression system. |
| Formulation | An experimental vaccine comprised of cultured insect cells and supernatant expressing recombinant H5 HA. The vaccine was adjuvanted with Polygen. |
| Generic product name | 511 |
| Antigen | Crude whole-cell H5 HA mutK+ protein expressed in insect cells by a baculovirus-based expression system. |
| Formulation | An experimental vaccine comprised of cultured insect cells and supernatant expressing recombinant H5 HA. The vaccine was adjuvanted with Emulsigen-P. |
| Generic product name | 512 |
| Antigen | Crude whole-cell H5 HA mutK+ protein expressed in insect cells by a baculovirus-based expression system. |
| Formulation | An experimental vaccine comprised of cultured insect cells and supernatant expressing recombinant H5 HA. The vaccine was adjuvanted with Carbigen. |
| Generic product name | 513 |
| Antigen | Crude whole-cell H5 HA mutK+ protein expressed in insect cells by a baculovirus-based expression system. |
| Formulation | An experimental vaccine comprised of cultured insect cells and supernatant expressing recombinant H5 HA. The vaccine was adjuvanted with Emulsigen-75. |
| Generic product name | 514 |
| Antigen | Crude whole-cell H5 HA K+ protein expressed in insect cells by a baculovirus-based expression system. |
| Formulation | An experimental vaccine comprised of cultured insect cells and supernatant expressing recombinant H5 HA. The vaccine was adjuvanted with ISA 70. |

Example 3

Vaccination of Chicken Against Avian Influenza

A combination vaccine comprising H5 HA Mutk+ (Fraction 1) and inactivated Newcastle disease virus (Fraction 2), named "BACULO AI+ND KV" has been evaluated in animal trials. The vaccine was formulated with the haemmagglutinin H5 produced in the Baculovirus expression system based on the MutK+ construct (Examples 1 and 2). The origin of the Newcastle Disease (ND) virus fraction is the whole virus.

Fraction 1

Recombinant, baculovirus-expressed, H5 hemagglutinin (H5 HA) from Avian Influenza H5N1 virus. Avian Influenza (AI) fraction.

AI fraction is inactivated with binary ethyleneimine (BEI). No residual infectivity coming from Baculovirus vector is allowed.

Fraction 2

Whole virion, Newcastle Disease Virus (ND), LaSota Strain. Newcastle Disease fraction.

ND fraction is inactivated with Formaldehyde, BEI or Beta-Propio-Lactone (BPL). No residual infectivity coming from ND virus is allowed.

Formula Composition

Inactivated harvest material from H5 HA protein and ND are blended into a water/oil emulsion. The mixture includes mineral oil as an adjuvant.

For evaluation of vaccine efficacy, three clinical parameters were considered: 1) Morbidity/mortality. 2) Antibodies levels. 3) Viral shedding.

In all studies SPF chickens were vaccinated, administration of the vaccine was by subcutaneous route, in the back of the neck. A dose of 0.5 ml was administered unless otherwise stated.

Chickens were maintained inside isolator units during the whole duration of the studies. Studies were compliant with OIE international guidelines for evaluation of Avian Influenza vaccines.

Challenge was conducted to evaluate the Avian Influenza (AI) antigenic fraction. Chickens were inoculated 3 weeks after vaccination by the intra-nasal (50 µl) and oral (50 µl) route administering a total of 100 µl of allantoic fluid containing $10^6$ $EID_{50}$ of the challenge virus.

To evaluate protection from challenge against HPAI H5N1 two studies were conducted:

1) Protectotypes study, using a single or double vaccination (evaluating boosting effect), ages of 1 day old or 10 days old chickens (evaluating age effect), and doses of 0.5 or 0.2 ml (evaluating dose effect).

Two different challenge strains were used for this study: a) A subclade 2.3.2 Vietnamese strain (isolated in 2006) which has been recently causing disease in South-East-Asia (China, Vietnam) Poultry production. b) A subclade 2.2.1 group B1 Egyptian strain (isolated in 2010), which has been recently causing disease in Egyptian Poultry production. Challenge strains are not genetically close to the vaccine baculovirus construct (MutK+). Results are interpreted in the context of protectotypes as broadening up the protection conferred for two immunizations with similar or different vaccines.

Conclusions

1) Protection between 80 and 100% was observed depending on the age or dose. 100% protection was observed when administered as 0.5 ml dose at 10 days old of the bivalent formulation.

2) When administered as a single 0.5 ml immunization of BACULO AI+ND KV at 10 days of age, the same protection is observed than administering two shots of the inactivated traditionally-produced commercial Volvac AI KV vaccine.

3) When administered as a single 0.5 ml immunization of BACULO AI+ND KV at 10 days of age, similar level of H5-specific antibodies were detected in comparison with administering two shots of the inactivated traditionally-produced commercial Volvac AI KV vaccine.

4) Low levels of viral shedding were observed until 3 days post-challenge, when the vaccine was administered as a single 0.5 ml immunization of BACULO AI+ND KV at 10 days of age.

2) BACULO efficacy study, using a single, unique vaccination at 10 days of age.

Three different challenge strains were used for this study: a) A subclade 2.2.1 Egyptian strain (isolated in 2008). b) A subclade 2.2.1 group A1 Egyptian strain (isolated in 2010). c) A subclade 2.2.1 group B1 Egyptian strain (isolated in 2010). The last two have been recently causing disease in Egyptian Poultry production.

Conclusions

1) Protection between 90 and 100% was observed.
2) Vaccine BACULO AI+ND KV showed performance compliant with European Medicine Agency (EMA) guidelines for vaccines against HPAI virus in birds.
3) This is the first report available demonstrating efficacy with a single shot administration for a baculovirus-based vaccine including a hemagglutinin genetically distant from those of the viruses used for challenge.

Example 4

2. Experimental Design

This experiment was designed and conducted similar to the above described Example 3:

For evaluation of vaccine efficacy, three clinical parameters were considered: 1) Morbidity/mortality. 2) Antibodies levels. 3) Viral shedding.

In all studies SPF chickens were vaccinated, the administration of the vaccine was by subcutaneous route, in the back of the neck. A vaccine prototype containing a clade 1 H5 protein was used (called Mut K+) formulated as a bivalent product with a second, ND (Newcastle disease virus) antigenic fraction.

A dose of 0.5 ml was administered unless otherwise stated. Animals were vaccinate at 10 days of age.

Chickens were maintained inside isolator units during the whole duration of the studies. Studies were compliant with OIE international guidelines for evaluation of Avian Influenza vaccines.

Challenge was conducted to evaluate the Avian Influenza (AI) antigenic fraction. Chickens were inoculated 3 weeks after vaccination by the intra-nasal (50 µl) and oral (50 µl) route administering a total of 100 µl of allantoic fluid containing $10^6$ $EID_{50}$ of the challenge virus.

This is also summarized in the table (Table A) below (Vaccination was performed at 10 days of age, column 1 (ID of experimental groups according to the vaccine applied), column 2 (Vaccine dose), and column 3 (Challenge age)).

Challenge virus was A/Chicken/Egypt/1063/2010, which is classified as subclade 2.2.1.1 HP AIV H5N1 subtype. This is the official challenge strain used in Egypt for evaluation of vaccine batches. The challenge dose was $10^6$ $EID_{50}$.

2. Results & Data Analysis

Results & Data analysis are summarized in the table below (Table A): Column 4 (HI GMT (Geometric Mean Titre) 3 weeks post-vaccination, pre-challenge), column 5 (Percentage of survival, 2 weeks post-challenge), and column 6 (Detection of viral shedding, RT-PCR positive samples).

3. Conclusions

The vaccinated group survived the challenge. The vaccine prototype triggered an efficient immune response, as measured as HI titration using the homologous antigen.

The Mut K+ vaccine prototype provided good virological protection, as measured as ability to reduce viral shedding. RT-PCR Ct values were far low to represent infectious virus but only residual genetical material instead.

In the sequence listing (SEQ ID NOs: 1 to 51):

SEQ ID NO: 1 corresponds to H5 of A/Hong Kong/213/2003(H5N1) without signal peptide, SEQ ID NOs: 2-7 correspond to SEQ ID NOs: 1-6 of the international (PCT) application number PCT/US2007/082699, SEQ ID NO: 8 corresponds to H5 sequence of H5N1 "1709-6", SEQ ID NO: 9 corresponds to H5 sequence of H5N1 "1553-1/A1", SEQ ID NO: 10 corresponds to H5 sequence of H5N1 "1553-15/A1", SEQ ID NO: 11 corresponds to H5 sequence of H5N1 "2095-50/A1", SEQ ID NO: 12 corresponds to H5 sequence of H5N1 "3982-2/A1", SEQ ID NO: 13 corresponds to H5 sequence of H5N1 "3982-5/A1", SEQ ID NO: 14 corresponds to H5 sequence of H5N1 "3982-7/A1", SEQ ID NO: 15 corresponds to H5 sequence of H5N1 "3982-8/A1", SEQ ID NO: 16 corresponds to H5 sequence of H5N1 "3982-9/A1", SEQ ID NO: 17 corresponds to H5 sequence of H5N1 "3982-12/A1", SEQ ID NO: 18 corresponds to H5 sequence of H5N1 "3982-20/A1", SEQ ID NO: 19 corresponds to H5 sequence of H5N1 "3982-44/A1", SEQ ID NO: 20 corresponds to H5 sequence of H5N1 "1553-2B1", SEQ ID NO: 21 corresponds to H5 sequence of H5N1 "1553-6/B1", SEQ ID NO: 22 corresponds to H5 sequence of H5N1 "1553-13/B2", SEQ ID NO: 23 corresponds to H5 sequence of H5N1 "1553-26/B2", SEQ ID NO: 24 corresponds to H5 sequence of H5N1 "1553-28/B1", SEQ ID NO: 25 corresponds to H5 sequence of H5N1 "2095-39/B2",

TABLE A

Summary of the experimental design and of the results and data analysis of Example 4.

| Experimental group (10 chickens each) -Vaccine ID- | Challenge Vaccine Dose (age) | Challenge dose (age) -Strain 1063- | GMT measured at 31 days of age Homologous (vaccine strain) | GMT measured at 31 days of age Heterologous (challenge virus) | Percentage of survival post-challenge (%) | Viral Shedding-Detection of viral RNA using RT-PCR- (#positives/total) |
|---|---|---|---|---|---|---|
| Mut K+ | 0.5 ml (10 days of age) | $10^6$ $EID_{50}$ (31 days of age) | 9.1 | 0.9 | 100 | 2/10 |
| No vaccine | | | — | — | 0 | 10/10 |

SEQ ID NO: 26 corresponds to H5 sequence of H5N1 "2095-46/B1",
SEQ ID NO: 27 corresponds to H5 sequence of H5N1 "2095-49/B1",
SEQ ID NO: 28 corresponds to H5 sequence of H5N1 "2095-65/B1",
SEQ ID NO: 29 corresponds to H5 sequence of H5N1 "2095-68/B2",
SEQ ID NO: 30 corresponds to H5 sequence of H5N1 "2095-70/B2",
SEQ ID NO: 31 corresponds to H5 sequence of H5N1 "2095-73/B2",
SEQ ID NO: 32 corresponds to H5 sequence of H5N1 "2095-75/B2",
SEQ ID NO: 33 corresponds to H5 sequence of H5N1 "3982-3/B1",
SEQ ID NO: 34 corresponds to H5 sequence of H5N1 "3982-4/B1",
SEQ ID NO: 35 corresponds to H5 sequence of H5N1 "3982-13/B1",
SEQ ID NO: 36 corresponds to H5 sequence of H5N1 "3982-14/B2",
SEQ ID NO: 37 corresponds to H5 sequence of H5N1 "3982-19/B3",
SEQ ID NO: 38 corresponds to H5 sequence of H5N1 "3982-21/B2",
SEQ ID NO: 39 corresponds to H5 sequence of H5N1 "3982-43/B1",
SEQ ID NO: 40 corresponds to H5 sequence of H5N1 "3982-50/B1",
SEQ ID NO: 41 corresponds to H5 sequence of H5N1 "3982-52/B1",
SEQ ID NO: 42 corresponds to H5 sequence of H5N1 "3982-55/A1",
SEQ ID NO: 43 corresponds to H5 sequence of H5N1 "3982-56/A1",
SEQ ID NO: 44 corresponds to H5 sequence of H5N1 "3982-78/B2",
SEQ ID NO: 45 corresponds to H5 sequence of H5N1 "4794-17/B",
SEQ ID NO: 46 corresponds to H5 sequence of H5N1 "4794-18/B",
SEQ ID NO: 47 corresponds to H5 sequence translated from SEQ ID NO: 50,
SEQ ID NO: 48 codes for a H5 sequence of H5N1 "3982-8/A1" (SEQ ID NO: 15),
SEQ ID NO: 49 codes for a H5 sequence of H5N1 "1553-2/B1" (SEQ ID NO: 20),
SEQ ID NO: 50 corresponds to the consensus sequence obtained after analysis of the 38 H5 HA gene sequences coding for SEQ ID NOs: 9 to 46,
SEQ ID NO: 51 corresponds to the cDNA of Newcastle Disease Virus LaSota strain.

The invention claimed is:

1. A method for protecting an animal against a clade 2 H5N1 influenza virus infection, comprising:
administering to the animal a composition comprising (i) a crude whole cell H5 protein of a clade 1 H5N1 influenza virus, expressed in insect cells by a baculovirus based expression system, in an amount effective to induce a cross-clade protective immune response in the animal against the clade 2 H5N1 influenza virus infection, and (ii) an inactivated Newcastle disease virus;
wherein the H5 protein of the clade 1 H5N1 influenza virus comprises a polypeptide sequence that has at least 98% sequence identity to SEQ ID NO:1;
wherein the H5 protein of the clade 1 H5N1 influenza virus has amino acid 223N and modification 328K+;
wherein amino acid position numbering of the H5 protein of the clade 1 H5N1 influenza virus refers to amino acid positions as given in SEQ ID NO:2; and
wherein modification 328K+ means that a second Lysine (K+) is inserted at amino acid position 328 of the H5 protein of the clade 1 H5N1 influenza virus.

2. The method of claim 1, wherein the H5 protein of the clade 1 H5N1 influenza virus has amino acid 94N, amino acid 120N, amino acid 155N, or any combinations thereof.

3. The method of claim 1, wherein the H5 protein of the clade 1 H5N1 influenza virus comprises an amino acid sequence according to:
  i. any one of SEQ ID NOs: 5-7;
  ii. any one of SEQ ID NOs: 5-7 modified to have at least one of the following amino acid clusters:
    a. aa 93-95: GNF
    b. aa 123-125: SDH
    c. aa 128-130: SSG
    d. aa 138-140: GSS
    e. aa 226-228: MDF
    f. aa 270-272: EVE
    g. aa 309-311: NKL;
  iii. any one of SEQ ID NOs: 5-7 modified to have at least one of the following amino acids: 36T, 36K, 83A, 83T, 83D, 86A, 86V, 120S, 155S, 156A, 156T, 189R, 189K, 212K, 212R, 212E, 263A, or 263T; or
  iv. any one of SEQ ID NOs: 5-7 modified to have at least one of the following amino acids: 36T, 36K, 83A, 83T, 83D, 86A, 86V, 120S, 155S, 156A, 156T, 189R, 189K, 212K, 212R, 212E, 263A, or 263T, and modified to have at least one of the following amino acid clusters:
    a. aa 93-95: GNF
    b. aa 123-125: SDH
    c. aa 128-130: SSG
    d. aa 138-140: GSS
    e. aa 226-228: MDF
    f. aa 270-272: EVE
    g. aa 309-311: NKL.

4. The method of claim 1, wherein the clade 2 H5N1 influenza virus is a clade 2.2 or clade 2.3 H5N1 influenza virus.

5. The method of claim 1, wherein the clade 2 H5N1 influenza virus is a clade 2.2.1 or clade 2.3.2 H5N1 influenza virus.

6. The method of claim 1, wherein the clade 2 H5N1 influenza virus is of North African or Vietnamese origin.

7. The method of claim 1, wherein the clade 2 H5N1 influenza virus comprises an H5 protein having:
  i. amino acids 113D, 126H, 145(−), 156R, 160F, 167T, and 181N, wherein modification 145(−) means that amino acid position 145 is deleted;
  ii. amino acids 87P, 145L, 172T, 201E, 206I, 208K, 254T, 341G, and 421K; or
  iii. amino acids 145L, 172T, and 254V,
  wherein amino acid position numbering of the H5 protein of the clade 2 H5N1 influenza virus refers to amino acid positions as given in SEQ ID NO:8.

8. The method of claim 1, wherein the clade 2 H5N1 influenza virus comprises an H5 protein having at least 95% sequence identity with at least one of SEQ ID NOs: 9-46.

9. The method of claim 1, wherein the clade 2 H5N1 influenza virus comprises an H5 protein having:
  i. amino acids 87L, 113D, 126H, 145(–), 156R, 160F, 167T, and 181N;
  ii. amino acids 87P, 113N, 126R, 145L, 160Y, 172T, 181H, 201E, 206I, 208K, 254T, 341G and 421K, or
  iii. amino acids 87L, 113N, 126R, 145L, 156G, 160Y, 172T, 181H, and 254V,
  wherein amino acid position numbering of the H5 protein of the clade 2 H5N1 influenza virus refers to amino acid positions as given in SEQ ID NO:8.

10. The method of claim 1, wherein the inactivated Newcastle disease virus was obtained by inactivating a Newcastle disease virus comprising a RNA polynucleotide having at least 95% sequence identity with a RNA copy of SEQ ID NO: 51.

11. The method of claim 1, wherein the inactivated Newcastle disease virus is an inactivated LaSota strain Newcastle disease virus.

12. The method of claim 1, wherein the inactivated Newcastle disease virus was obtained by inactivation with formaldehyde, binary ethylenimine, β-propiolactone, or any combinations thereof.

13. The method of claim 1, wherein the animal is a poultry.

14. The method of claim 1, wherein the composition is administered as a single dose.

15. A method for protecting an animal against clade 2 H5N1 influenza virus infection, comprising:
  administering to the animal a vaccine comprising (i) an H5 protein of a clade 1 H5N1 influenza virus in an amount effective to induce a cross-clade protective immune response in the animal against clade 2 H5N1 influenza virus infection, (ii) an inactivated Newcastle disease virus, and (iii) an adjuvant,
  wherein the H5 protein of the clade 1 H5N1 influenza virus comprises a polypeptide sequence that has at least 98% sequence identity to SEQ ID NO:1,
  wherein amino acid position numbering of the H5 protein of the clade 1 H5N1 influenza virus refers to amino acid positions as given in SEQ ID NO:2; and
  wherein modification 328K+ means that a second Lysine (K+) is inserted at amino acid position 328 of the H5 protein of the clade 1 H5N1 influenza virus.

16. The method of claim 15, wherein the adjuvant is an oil-in water emulsified adjuvant.

17. The method of claim 15, wherein the H5 protein of the clade 1 H5N1 influenza virus has amino acid 94N, amino acid 120N, amino acid 155N, or any combinations thereof.

18. The method of claim 15, wherein the H5 protein of the clade 1 H5N1 influenza virus comprises an amino acid sequence according to:
  i. any one of SEQ ID NOs: 5-7;
  ii. any one of SEQ ID NOs: 5-7 modified to have at least one of the following amino acid clusters:
    a. aa 93-95: GNF
    b. aa 123-125: SDH
    c. aa 128-130: SSG
    d. aa 138-140: GSS
    e. aa 226-228: MDF
    f. aa 270-272: EVE
    g. aa 309-311: NKL;
  iii. any one of SEQ ID NOs: 5-7 modified to have at least one of the following amino acids: 36T, 36K, 83A, 83T, 83D, 86A, 86V, 120S, 155S, 156A, 156T, 189R, 189K, 212K, 212R, 212E, 263A, or 263T; or
  iv. any one of SEQ ID NOs: 5-7 modified to have at least one of the following amino acids: 36T, 36K, 83A, 83T, 83D, 86A, 86V, 120S, 155S, 156A, 156T, 189R, 189K, 212K, 212R, 212E, 263A, or 263T, and modified to have at least one of the following amino acid clusters:
    a. aa 93-95: GNF
    b. aa 123-125: SDH
    c. aa 128-130: SSG
    d. aa 138-140: GSS
    e. aa 226-228: MDF
    f. aa 270-272: EVE
    g. aa 309-311: NKL.

19. The method of claim 15, wherein the clade 2 H5N1 influenza virus is a clade 2.2 or clade 2.3 H5N1 influenza virus.

20. The method of claim 15, wherein the clade 2 H5N1 influenza virus is a clade 2.2.1 or clade 2.3.2 H5N1 influenza virus.

21. The method of claim 15, wherein the clade 2 H5N1 influenza virus is of North African or Vietnamese origin.

22. The method of claim 15, wherein the clade 2 H5N1 influenza virus comprises an H5 protein having:
  i. amino acids 113D, 126H, 145(–), 156R, 160F, 167T, and 181N, wherein modification 145(–) means that amino acid position 145 is deleted;
  ii. amino acids 87P, 145L, 172T, 201E, 206I, 208K, 254T, 341G, and 421K; or
  iii. amino acids 145L, 172T, and 254V,
  wherein amino acid position numbering of the H5 protein of the clade 2 H5N1 influenza virus refers to amino acid positions as given in SEQ ID NO:8.

23. The method of claim 15, wherein the clade 2 H5N1 influenza virus comprises an H5 protein having at least 95% sequence identity with at least one of SEQ ID NOs: 9-46.

24. The method of claim 15, wherein the clade 2 H5N1 influenza virus comprises an H5 protein having:
  i. amino acids 87L, 113D, 126H, 145(–), 156R, 160F, 167T, and 181N;
  ii. amino acids 87P, 113N, 126R, 145L, 160Y, 172T, 181H, 201E, 206I, 208K, 254T, 341G and 421K, or
  iii. amino acids 87L, 113N, 126R, 145L, 156G, 160Y, 172T, 181H, and 254V,
  wherein amino acid position numbering of the H5 protein of the clade 2 H5N1 influenza virus refers to amino acid positions as given in SEQ ID NO:8.

25. The method of claim 15, wherein the inactivated Newcastle disease virus was obtained by inactivating a Newcastle disease virus comprising a RNA polynucleotide having at least 95% sequence identity with a RNA copy of SEQ ID NO: 51.

26. The method of claim 15, wherein the inactivated Newcastle disease virus is an inactivated LaSota strain Newcastle disease virus.

27. The method of claim 15, wherein the inactivated Newcastle disease virus was obtained by inactivation with formaldehyde, binary ethylenimine, β-propiolactone, or any combinations thereof.

28. The method of claim 15, wherein the animal is a poultry.

29. The method of claim 15, wherein the composition is administered as a single dose.

* * * * *

SEQUENCE LISTING

```
<160> NUMBER OF SEQ ID NOS: 51

<210> SEQ ID NO 1
<211> LENGTH: 552
<212> TYPE: PRT
<213> ORGANISM: Avian influenza virus

<400> SEQUENCE: 1

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Asn Pro Ala Asn Asp Leu Cys Tyr Pro Gly Asp Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Asn Ser Trp Ser Ser His Glu Ala Ser
        115                 120                 125

Leu Gly Val Ser Ser Ala Cys Pro Tyr Gln Gly Lys Ser Ser Phe Phe
    130                 135                 140

Arg Asn Val Val Trp Leu Ile Lys Lys Asn Ala Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Arg Leu Tyr Gln
            180                 185                 190
```

```
Asn Pro Thr Thr Tyr Ile Ser Val Gly Thr Ser Thr Leu Asn Gln Arg
        195                 200                 205

Leu Val Pro Lys Ile Ala Thr Arg Ser Lys Val Asn Gly Gln Asn Gly
    210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Ala Ile Met Lys Ser Glu Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
    290                 295                 300

Tyr Val Lys Ser Asn Arg Leu Val Leu Ala Thr Gly Leu Arg Asn Ser
305                 310                 315                 320

Pro Gln Arg Glu Arg Arg Lys Lys Arg Gly Leu Phe Gly Ala Ile
                325                 330                 335

Ala Gly Phe Ile Glu Gly Gly Trp Gln Gly Met Val Asp Gly Trp Tyr
                340                 345                 350

Gly Tyr His His Ser Asn Glu Gln Gly Ser Gly Tyr Ala Ala Asp Lys
            355                 360                 365

Glu Ser Thr Gln Lys Ala Ile Asp Gly Val Thr Asn Lys Val Asn Ser
    370                 375                 380

Ile Ile Asp Lys Met Asn Thr Gln Phe Glu Ala Val Gly Arg Glu Phe
385                 390                 395                 400

Asn Asn Leu Glu Arg Arg Ile Glu Asn Leu Asn Lys Lys Met Glu Asp
                405                 410                 415

Gly Phe Leu Asp Val Trp Thr Tyr Asn Ala Glu Leu Leu Val Leu Met
                420                 425                 430

Glu Asn Glu Arg Thr Leu Asp Phe His Asp Ser Asn Val Lys Asn Leu
    435                 440                 445

Tyr Asp Lys Val Arg Leu Gln Leu Arg Asp Asn Ala Lys Glu Leu Gly
450                 455                 460

Asn Gly Cys Phe Glu Phe Tyr His Lys Cys Asp Asn Glu Cys Met Glu
465                 470                 475                 480

Ser Val Arg Asn Gly Thr Tyr Asp Tyr Pro Gln Tyr Ser Glu Glu Ala
                485                 490                 495

Arg Leu Lys Arg Glu Glu Ile Ser Gly Val Lys Leu Glu Ser Ile Gly
                500                 505                 510

Thr Tyr Gln Ile Leu Ser Ile Tyr Ser Thr Val Ala Ser Ser Leu Ala
    515                 520                 525

Leu Ala Ile Met Val Ala Gly Leu Ser Leu Trp Met Cys Ser Asn Gly
530                 535                 540

Ser Leu Gln Cys Arg Ile Cys Ile
545                 550

<210> SEQ ID NO 2
<211> LENGTH: 551
<212> TYPE: PRT
<213> ORGANISM: Avian influenza virus

<400> SEQUENCE: 2

Asp Gln Ile Cys Ile Gly Tyr His Ala Asn Asn Ser Thr Glu Gln Val
```

-continued

```
1               5                   10                  15
Asp Thr Ile Met Glu Lys Asn Val Thr Val Thr His Ala Gln Asp Ile
                20                  25                  30
Leu Glu Lys Thr His Asn Gly Lys Leu Cys Asp Leu Asp Gly Val Lys
                35                  40                  45
Pro Leu Ile Leu Arg Asp Cys Ser Val Ala Gly Trp Leu Leu Gly Asn
50                  55                  60
Pro Met Cys Asp Glu Phe Ile Asn Val Pro Glu Trp Ser Tyr Ile Val
65                  70                  75                  80
Glu Lys Ala Asn Pro Ala Asn Asp Leu Cys Tyr Pro Gly Asn Phe Asn
                85                  90                  95
Asp Tyr Glu Glu Leu Lys His Leu Leu Ser Arg Ile Asn His Phe Glu
                100                 105                 110
Lys Ile Gln Ile Ile Pro Lys Ser Ser Trp Ser Asp His Glu Ala Ser
                115                 120                 125
Ser Gly Val Ser Ser Ala Cys Pro Tyr Gln Gly Ser Ser Ser Phe Phe
                130                 135                 140
Arg Asn Val Val Trp Leu Ile Lys Lys Asn Asp Ala Tyr Pro Thr Ile
145                 150                 155                 160
Lys Arg Ser Tyr Asn Asn Thr Asn Gln Glu Asp Leu Leu Val Leu Trp
                165                 170                 175
Gly Ile His His Pro Asn Asp Ala Ala Glu Gln Thr Arg Leu Tyr Gln
                180                 185                 190
Asn Pro Thr Thr Tyr Ile Ser Val Gly Thr Ser Thr Leu Asn Gln Arg
                195                 200                 205
Leu Val Pro Lys Ile Ala Thr Arg Ser Lys Val Asn Gly Gln Ser Gly
                210                 215                 220
Arg Met Asp Phe Phe Trp Thr Ile Leu Lys Pro Asn Asp Ala Ile Asn
225                 230                 235                 240
Phe Glu Ser Asn Gly Asn Phe Ile Ala Pro Glu Tyr Ala Tyr Lys Ile
                245                 250                 255
Val Lys Lys Gly Asp Ser Ala Ile Met Lys Ser Glu Val Glu Tyr Gly
                260                 265                 270
Asn Cys Asn Thr Lys Cys Gln Thr Pro Met Gly Ala Ile Asn Ser Ser
                275                 280                 285
Met Pro Phe His Asn Ile His Pro Leu Thr Ile Gly Glu Cys Pro Lys
                290                 295                 300
Tyr Val Lys Ser Asn Lys Leu Val Leu Ala Thr Gly Leu Arg Asn Ser
305                 310                 315                 320
Pro Gln Arg Glu Arg Arg Lys Arg Gly Leu Phe Gly Ala Ile Ala
                325                 330                 335
Gly Phe Ile Glu Gly Gly Trp Gln Gly Met Val Asp Gly Trp Tyr Gly
                340                 345                 350
Tyr His His Ser Asn Glu Gln Gly Ser Gly Tyr Ala Ala Asp Lys Glu
                355                 360                 365
Ser Thr Gln Lys Ala Ile Asp Gly Val Thr Asn Lys Val Asn Ser Ile
                370                 375                 380
Ile Asp Lys Met Asn Thr Gln Phe Glu Ala Val Gly Arg Glu Phe Asn
385                 390                 395                 400
Asn Leu Glu Arg Arg Ile Glu Asn Leu Asn Lys Lys Met Glu Asp Gly
                405                 410                 415
Phe Leu Asp Val Trp Thr Tyr Asn Ala Glu Leu Leu Val Leu Met Glu
                420                 425                 430
```

```
Asn Glu Arg Thr Leu Asp Phe His Asp Ser Asn Val Lys Asn Leu Tyr
            435                 440                 445

Asp Lys Val Arg Leu Gln Leu Arg Asp Asn Ala Lys Glu Leu Gly Asn
        450                 455                 460

Gly Cys Phe Glu Phe Tyr His Lys Cys Asp Asn Glu Cys Met Glu Ser
465                 470                 475                 480

Val Arg Asn Gly Thr Tyr Asp Tyr Pro Gln Tyr Ser Glu Glu Ala Arg
                485                 490                 495

Leu Lys Arg Glu Glu Ile Ser Gly Val Lys Leu Glu Ser Ile Gly Thr
            500                 505                 510

Tyr Gln Ile Leu Ser Ile Tyr Ser Thr Val Ala Ser Ser Leu Ala Leu
            515                 520                 525

Ala Ile Met Val Ala Gly Leu Ser Leu Trp Met Cys Ser Asn Gly Ser
        530                 535                 540

Leu Gln Cys Arg Ile Cys Ile
545                 550

<210> SEQ ID NO 3
<211> LENGTH: 567
<212> TYPE: PRT
<213> ORGANISM: Avian influenza virus

<400> SEQUENCE: 3

Met Glu Lys Thr Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Ser Ser Ser Phe Phe
145                 150                 155                 160

Arg Asn Val Val Trp Leu Ile Lys Lys Asn Asp Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Asp Phe Phe Trp Thr Ile Leu Lys Pro Asn Asp Ala Ile Asn
```

```
            245                 250                 255
Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Val Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Gln Arg Glu Arg Arg Lys Arg Gly Leu Phe Gly Ala Ile Ala
                340                 345                 350

Gly Phe Ile Glu Gly Gly Trp Gln Gly Met Val Asp Gly Trp Tyr Gly
            355                 360                 365

Tyr His His Ser Asn Glu Gln Gly Ser Gly Tyr Ala Ala Asp Lys Glu
        370                 375                 380

Ser Thr Gln Lys Ala Ile Asp Gly Val Thr Asn Lys Val Asn Ser Ile
385                 390                 395                 400

Ile Asp Lys Met Asn Thr Gln Phe Glu Ala Val Gly Arg Glu Phe Asn
                405                 410                 415

Asn Leu Glu Arg Arg Ile Glu Asn Leu Asn Lys Lys Met Glu Asp Gly
            420                 425                 430

Phe Leu Asp Val Trp Thr Tyr Asn Ala Glu Leu Leu Val Leu Met Glu
        435                 440                 445

Asn Glu Arg Thr Leu Asp Phe His Asp Ser Asn Val Lys Asn Leu Tyr
    450                 455                 460

Asp Lys Val Arg Leu Gln Leu Arg Asp Asn Ala Lys Glu Leu Gly Asn
465                 470                 475                 480

Gly Cys Phe Glu Phe Tyr His Lys Cys Asp Asn Glu Cys Met Glu Ser
                485                 490                 495

Val Arg Asn Gly Thr Tyr Asp Tyr Pro Gln Tyr Ser Glu Glu Ala Arg
            500                 505                 510

Leu Lys Arg Glu Glu Ile Ser Gly Val Lys Leu Glu Ser Ile Gly Thr
        515                 520                 525

Tyr Gln Ile Leu Ser Ile Tyr Ser Thr Val Ala Ser Ser Leu Ala Leu
    530                 535                 540

Ala Ile Met Val Ala Gly Leu Ser Leu Trp Met Cys Ser Asn Gly Ser
545                 550                 555                 560

Leu Gln Cys Arg Ile Cys Ile
                565
```

<210> SEQ ID NO 4
<211> LENGTH: 568
<212> TYPE: PRT
<213> ORGANISM: Avian influenza virus

<400> SEQUENCE: 4

```
Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45
```

-continued

Leu Glu Lys Thr His Asn Gly Lys Leu Cys Asp Leu Asp Gly Val Lys
 50                  55                  60

Pro Leu Ile Leu Arg Asp Cys Ser Val Ala Gly Trp Leu Leu Gly Asn
 65                  70                  75                  80

Pro Met Cys Asp Glu Phe Ile Asn Val Pro Glu Trp Ser Tyr Ile Val
                 85                  90                  95

Glu Lys Ala Asn Pro Ala Asn Asp Leu Cys Tyr Pro Gly Asp Phe Asn
             100                 105                 110

Asp Tyr Glu Glu Leu Lys His Leu Leu Ser Arg Ile Asn His Phe Glu
         115                 120                 125

Lys Ile Gln Ile Ile Pro Lys Asn Ser Trp Ser Ser His Glu Ala Ser
130                 135                 140

Leu Gly Val Ser Ser Ala Cys Pro Tyr Gln Gly Lys Ser Ser Phe Phe
145                 150                 155                 160

Arg Asn Val Val Trp Leu Ile Lys Lys Asn Asn Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Asn Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly

```
                465            470            475            480
        Asn Gly Cys Phe Glu Phe Tyr His Lys Cys Asp Asn Glu Cys Met Glu
                        485                490                495

Ser Val Arg Asn Gly Thr Tyr Asp Tyr Pro Gln Tyr Ser Glu Glu Ala
                        500                505                510

Arg Leu Lys Arg Glu Glu Ile Ser Gly Val Lys Leu Glu Ser Ile Gly
                        515                520                525

Thr Tyr Gln Ile Leu Ser Ile Tyr Ser Thr Val Ala Ser Ser Leu Ala
                        530                535                540

Leu Ala Ile Met Val Ala Gly Leu Ser Leu Trp Met Cys Ser Asn Gly
        545                550                555                560

Ser Leu Gln Cys Arg Ile Cys Ile
                        565

<210> SEQ ID NO 5
<211> LENGTH: 568
<212> TYPE: PRT
<213> ORGANISM: Avian influenza virus

<400> SEQUENCE: 5

Met Glu Lys Thr Val Leu Leu Leu Ala Ile Val Ser Leu Val Lys Ser
        1                   5                   10                  15

Asp Gln Ile Cys Ile Gly Tyr His Ala Asn Asn Ser Thr Glu Gln Val
                        20                  25                  30

Asp Thr Ile Met Glu Lys Asn Val Thr Val Thr His Ala Gln Asp Ile
                        35                  40                  45

Leu Glu Lys Thr His Asn Gly Lys Leu Cys Asp Leu Asp Gly Val Lys
        50                  55                  60

Pro Leu Ile Leu Arg Asp Cys Ser Val Ala Gly Trp Leu Leu Gly Asn
        65                  70                  75                  80

Pro Met Cys Asp Glu Phe Ile Asn Val Pro Glu Trp Ser Tyr Ile Val
                        85                  90                  95

Glu Lys Ala Asn Pro Ala Asn Asp Leu Cys Tyr Pro Gly Asn Phe Asn
                        100                 105                 110

Asp Tyr Glu Glu Leu Lys His Leu Leu Ser Arg Ile Asn His Phe Glu
                        115                 120                 125

Lys Ile Gln Ile Ile Pro Lys Asn Ser Trp Ser Asp His Glu Ala Ser
        130                 135                 140

Ser Gly Val Ser Ser Ala Cys Pro Tyr Gln Gly Ser Ser Ser Phe Phe
        145                 150                 155                 160

Arg Asn Val Val Trp Leu Ile Lys Lys Asn Asn Ala Tyr Pro Thr Ile
                        165                 170                 175

Lys Arg Ser Tyr Asn Asn Thr Asn Gln Glu Asp Leu Leu Val Leu Trp
                        180                 185                 190

Gly Ile His His Pro Asn Asp Ala Ala Glu Gln Thr Arg Leu Tyr Gln
                        195                 200                 205

Asn Pro Thr Thr Tyr Ile Ser Val Gly Thr Ser Thr Leu Asn Gln Arg
        210                 215                 220

Leu Val Pro Lys Ile Ala Thr Arg Ser Lys Val Asn Gly Gln Asn Gly
        225                 230                 235                 240

Arg Met Asp Phe Phe Trp Thr Ile Leu Lys Pro Asn Asp Ala Ile Asn
                        245                 250                 255

Phe Glu Ser Asn Gly Asn Phe Ile Ala Pro Glu Tyr Ala Tyr Lys Ile
                        260                 265                 270
```

```
Val Lys Lys Gly Asp Ser Ala Ile Met Lys Ser Glu Val Glu Tyr Gly
            275                 280                 285

Asn Cys Asn Thr Lys Cys Gln Thr Pro Met Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
            325                 330                 335

Pro Gln Arg Glu Arg Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
            355                 360                 365

Gly Tyr His His Ser Asn Glu Gln Gly Ser Gly Tyr Ala Ala Asp Lys
            370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
                420                 425                 430

Gly Phe Leu Asp Val Trp Thr Tyr Asn Ala Glu Leu Leu Val Leu Met
            435                 440                 445

Glu Asn Glu Arg Thr Leu Asp Phe His Asp Ser Asn Val Lys Asn Leu
            450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Gly Val Lys Leu Glu Ser Ile Gly
            515                 520                 525

Thr Tyr Gln Ile Leu Ser Ile Tyr Ser Thr Val Ala Ser Ser Leu Ala
530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 6
<211> LENGTH: 263
<212> TYPE: PRT
<213> ORGANISM: Avian influenza virus

<400> SEQUENCE: 6

His Ala Asn Asn Trp Thr Glu Gln Val Asp Thr Ile Met Glu Lys Asn
1               5                   10                  15

Val Thr Val Thr His Ala Gln Asp Ile Leu Glu Lys Thr His Asn Gly
            20                  25                  30

Lys Leu Cys Asp Leu Asp Gly Val Lys Pro Leu Ile Leu Arg Asp Cys
        35                  40                  45

Ser Val Ala Gly Trp Leu Leu Gly Asn Pro Met Cys Asp Glu Phe Ile
    50                  55                  60

Asn Val Pro Glu Trp Ser Tyr Ile Val Glu Lys Ala Asn Pro Ala Asn
65                  70                  75                  80
```

-continued

Asp Leu Cys Tyr Pro Gly Asp Phe Asn Asp Tyr Glu Glu Leu Lys His
            85                  90                  95

Leu Leu Ser Arg Ile Asn His Phe Glu Lys Ile Gln Ile Ile Pro Lys
            100                 105                 110

Asn Ser Trp Ser Ser His Glu Ala Ser Leu Gly Val Ser Ser Ala Cys
            115                 120                 125

Pro Tyr Gln Gly Lys Ser Ser Phe Phe Arg Asn Val Val Trp Leu Ile
            130                 135                 140

Lys Lys Asn Asn Ala Tyr Pro Thr Ile Lys Arg Ser Tyr Asn Asn Thr
145                 150                 155                 160

Asn Gln Glu Asp Leu Leu Val Leu Trp Gly Ile His Pro Asn Asp
                    165                 170                 175

Ala Ala Glu Gln Thr Arg Leu Tyr Gln Asn Pro Thr Thr Tyr Ile Ser
                    180                 185                 190

Val Gly Thr Ser Thr Leu Asn Gln Arg Leu Val Pro Lys Ile Ala Thr
                    195                 200                 205

Arg Ser Lys Val Asn Gly Gln Asn Gly Arg Met Glu Phe Phe Trp Thr
210                 215                 220

Ile Leu Lys Pro Asn Asp Ala Ile Asn Phe Glu Ser Asn Gly Asn Phe
225                 230                 235                 240

Ile Ala Pro Glu Tyr Ala Tyr Lys Ile Val Lys Lys Gly Asp Ser Ala
                    245                 250                 255

Ile Met Lys Ser Glu Leu Glu
                    260

<210> SEQ ID NO 7
<211> LENGTH: 290
<212> TYPE: PRT
<213> ORGANISM: Avian influenza virus

<400> SEQUENCE: 7

Gly Ser Ala Thr Met Glu Lys Thr Val Leu Leu Leu Ala Ile Val Ser
1               5                   10                  15

Leu Val Lys Ser Asp Gln Ile Cys Ile Gly Tyr His Ala Asn Asn Ser
                20                  25                  30

Thr Glu Gln Val Asp Thr Ile Met Glu Lys Asn Val Thr Val Thr His
            35                  40                  45

Ala Gln Asp Ile Leu Glu Lys Thr His Asn Gly Lys Leu Cys Asp Leu
        50                  55                  60

Asp Gly Val Lys Pro Leu Ile Leu Arg Asp Cys Ser Val Ala Gly Trp
65                  70                  75                  80

Leu Leu Gly Asn Pro Met Cys Asp Glu Phe Ile Asn Val Pro Glu Trp
                85                  90                  95

Ser Tyr Ile Val Glu Lys Ala Asn Pro Ala Asn Asp Leu Cys Tyr Pro
            100                 105                 110

Gly Asn Phe Asn Asp Tyr Glu Glu Leu Lys His Leu Leu Ser Arg Ile
            115                 120                 125

Asn His Phe Glu Lys Ile Gln Ile Ile Pro Lys Ser Ser Trp Ser Asp
        130                 135                 140

His Glu Ala Ser Ser Gly Val Ser Ser Ala Cys Pro Tyr Gln Gly Ser
145                 150                 155                 160

Ser Ser Phe Phe Arg Asn Val Val Trp Leu Ile Lys Lys Asn Asp Ala
                165                 170                 175

Tyr Pro Thr Ile Lys Arg Ser Tyr Asn Asn Thr Asn Gln Glu Asp Leu

```
            180                 185                 190
Leu Val Leu Trp Gly Ile His His Pro Asn Asp Ala Ala Glu Gln Thr
            195                 200                 205

Arg Leu Tyr Gln Asn Pro Thr Thr Tyr Ile Ser Val Gly Thr Ser Thr
        210                 215                 220

Leu Asn Gln Arg Leu Val Pro Lys Ile Ala Thr Arg Ser Lys Val Asn
225                 230                 235                 240

Gly Gln Ser Gly Arg Met Asp Phe Phe Trp Thr Ile Leu Lys Pro Asn
                245                 250                 255

Asp Ala Ile Asn Phe Glu Ser Asn Gly Asn Phe Ile Ala Pro Glu Tyr
            260                 265                 270

Ala Tyr Lys Ile Val Lys Lys Gly Asp Ser Ala Ile Met Lys Ser Glu
        275                 280                 285

Val Glu
    290

<210> SEQ ID NO 8
<211> LENGTH: 562
<212> TYPE: PRT
<213> ORGANISM: H5N1

<400> SEQUENCE: 8

Met Glu Lys Ile Val Leu Leu Leu Ala Ile Val Ser Leu Val Lys Ser
1               5                   10                  15

Asp Gln Ile Cys

-continued

Phe Glu Ser Asn Gly Asn Phe Ile Ala Pro Glu Asn Ala Tyr Lys Ile
                260                 265                 270

Val Lys Lys Gly Asp Ser Thr Ile Met Lys Ser Glu Leu Glu Tyr Gly
            275                 280                 285

Asn Cys Asn Thr Lys Cys Gln Thr Pro Ile Gly Ala Ile Asn Ser Ser
        290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Gly Glu Arg Arg Lys Lys Arg Gly Leu Phe Gly Ala Ile
                340                 345                 350

Ala Gly Phe Ile Glu Gly Gly Trp Gln Gly Met Val Asp Gly Trp Tyr
            355                 360                 365

Gly Tyr His His Ser Asn Glu Gln Gly Ser Gly Tyr Ala Ala Asp Lys
        370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Arg Cys Asp Asn Glu Cys Met Glu
            485                 490                 495

Ser Val Arg Asn Gly Thr Tyr Asp Tyr Pro Gln Tyr Ser Glu Glu Ala
        500                 505                 510

Arg Leu Lys Arg Glu Glu Ile Ser Gly Val Lys Leu Glu Ser Ile Gly
515                 520                 525

Thr Tyr Gln Ile Leu Ser Ile Tyr Ser Thr Val Ala Ser Ser Leu Ala
        530                 535                 540

Leu Ala Ile Met Val Ala Gly Leu Phe Leu Trp Met Cys Ser Asn Gly
545                 550                 555                 560

Ser Leu

<210> SEQ ID NO 9
<211> LENGTH: 567
<212> TYPE: PRT
<213> ORGANISM: H5N1

<400> SEQUENCE: 9

Met Glu Lys Ile Met Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asn Leu Asp Gly Val Lys
    50                  55                  60

```
Pro Leu Ile Leu Arg Asp Cys Ser Val Ala Gly Trp Leu Leu Gly Asn
 65                  70                  75                  80

Pro Met Cys Asp Glu Phe Leu Asn Val Pro Glu Trp Ser Tyr Ile Val
                 85                  90                  95

Glu Lys Ile Asn Pro Ala Asn Asp Leu Cys Tyr Pro Gly Lys Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Arg Asn Ser Trp Ser Asp His Glu Thr Ser
    130                 135                 140

Gly Val Ser Ser Ala Cys Gln Tyr Gln Gly Arg Ser Ser Phe Phe Arg
145                 150                 155                 160

Asn Val Val Trp Leu Thr Lys Lys Asp Asn Ala Tyr Ser Thr Ile Lys
                165                 170                 175

Arg Ser Tyr Asn Asn Thr Asn Gln Glu Asp Leu Leu Val Leu Trp Gly
            180                 185                 190

Ile His His Pro Asn Asp Ala Ala Glu Gln Thr Arg Leu Tyr Gln Asn
        195                 200                 205

Pro Thr Thr Tyr Ile Ser Val Gly Thr Ser Thr Leu Asn Gln Arg Leu
    210                 215                 220

Val Pro Lys Ile Ala Thr Arg Ser Lys Val Asn Gly Gln Ser Gly Arg
225                 230                 235                 240

Met Glu Phe Phe Trp Thr Ile Leu Lys Ser Asn Asp Ala Ile Asn Phe
                245                 250                 255

Glu Ser Asn Gly Asn Phe Ile Ala Pro Glu Asn Ala Tyr Lys Ile Val
            260                 265                 270

Lys Lys Gly Asp Ser Thr Ile Met Lys Ser Glu Leu Glu Tyr Gly Asn
        275                 280                 285

Cys Asn Thr Lys Cys Gln Thr Pro Ile Gly Ala Ile Asn Ser Ser Met
    290                 295                 300

Pro Phe His Asn Ile His Pro Leu Thr Ile Gly Glu Cys Pro Lys Tyr
305                 310                 315                 320

Val Lys Ser Asn Arg Leu Val Leu Ala Thr Gly Leu Arg Asn Ser Pro
                325                 330                 335

Gln Glu Glu Arg Arg Lys Lys Arg Gly Leu Phe Gly Ala Ile Ala
            340                 345                 350

Gly Phe Ile Glu Gly Gly Trp Gln Gly Met Val Asp Gly Trp Tyr Gly
        355                 360                 365

Tyr His His Ser Asn Glu Gln Gly Ser Gly Tyr Ala Ala Asp Lys Glu
    370                 375                 380

Ser Thr Gln Lys Ala Ile Asp Gly Val Thr Asn Lys Val Asn Ser Ile
385                 390                 395                 400

Ile Asp Lys Met Asn Thr Gln Phe Glu Ala Val Gly Arg Glu Phe Asn
                405                 410                 415

Asn Leu Glu Arg Arg Ile Glu Asn Leu Asn Lys Lys Met Glu Asp Gly
            420                 425                 430

Phe Leu Asp Val Trp Thr Tyr Asn Ala Glu Leu Leu Val Leu Met Glu
        435                 440                 445

Asn Glu Arg Thr Leu Asp Phe His Asp Ser Asn Val Lys Asn Leu Tyr
    450                 455                 460

Asp Lys Val Arg Leu Gln Leu Arg Asp Asn Ala Lys Glu Leu Gly Asn
465                 470                 475                 480

Gly Cys Phe Glu Phe Tyr His Arg Cys Asp Asn Glu Cys Met Glu Ser
```

```
                485                 490                 495
Val Arg Asn Gly Thr Tyr Asp Tyr Pro Gln Tyr Ser Glu Glu Ala Arg
            500                 505                 510

Leu Lys Arg Glu Glu Ile Ser Gly Val Lys Leu Glu Ser Ile Gly Thr
            515                 520                 525

Tyr Gln Ile Leu Ser Ile Tyr Ser Thr Val Ala Ser Ser Leu Ala Leu
            530                 535                 540

Ala Ile Met Val Ala Gly Leu Phe Leu Trp Met Cys Ser Asn Gly Ser
545                 550                 555                 560

Leu Gln Cys Arg Ile Cys Ile
                565

<210> SEQ ID NO 10
<211> LENGTH: 567
<212> TYPE: PRT
<213> ORGANISM: H5N1

<400> SEQUENCE: 10

Met Glu Lys Ile Val Leu Leu Leu Ala Ile Val Ser Ile Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asn Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Leu Asn Val Pro Glu Trp Ser Tyr Ile Val
                85                  90                  95

Glu Lys Ile Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Gly Ser Trp Ser Asp His Glu Ala Ser
    130                 135                 140

Gly Val Ser Ser Ala Cys Pro Tyr Gln Gly Arg Ser Ser Phe Phe Arg
145                 150                 155                 160

Asn Val Val Trp Leu Thr Lys Lys Asn Asn Ala Tyr Pro Thr Ile Lys
                165                 170                 175

Lys Ser Tyr Asn Asn Thr Asn Gln Glu Asp Leu Leu Val Leu Trp Gly
            180                 185                 190

Ile His His Pro Asn Asp Ala Ala Glu Gln Thr Arg Leu Tyr Gln Asn
        195                 200                 205

Pro Thr Thr Tyr Ile Ser Val Gly Thr Ser Thr Leu Asn Gln Arg Leu
    210                 215                 220

Val Pro Lys Ile Ala Thr Arg Ser Lys Val Asn Gly Gln Ser Gly Arg
225                 230                 235                 240

Met Glu Phe Phe Trp Thr Ile Leu Lys Ser Asn Asp Ala Ile Asn Phe
                245                 250                 255

Glu Ser Asn Gly Asn Phe Ile Ala Pro Glu Asn Ala Tyr Lys Ile Val
            260                 265                 270

Lys Lys Gly Asp Ser Thr Ile Met Lys Ser Glu Leu Glu Tyr Gly Asn
        275                 280                 285
```

```
Cys Asn Thr Lys Cys Gln Thr Pro Ile Gly Ala Ile Asn Ser Ser Met
            290                 295                 300
Pro Phe His Asn Ile His Pro Leu Thr Ile Gly Glu Cys Pro Lys Tyr
305                 310                 315                 320
Val Lys Ser Asn Arg Leu Val Leu Ala Thr Gly Leu Arg Asn Ser Pro
                325                 330                 335
Gln Gly Glu Arg Arg Lys Arg Gly Leu Phe Gly Ala Ile Ala
            340                 345                 350
Gly Phe Ile Glu Gly Gly Trp Gln Gly Met Val Asp Gly Trp Tyr Gly
                355                 360                 365
Tyr His His Ser Asn Glu Gln Gly Ser Gly Tyr Ala Ala Asp Lys Glu
370                 375                 380
Ser Thr Gln Lys Ala Ile Asp Gly Val Thr Asn Lys Val Asn Ser Ile
385                 390                 395                 400
Ile Asp Lys Met Asn Thr Gln Phe Glu Ala Val Gly Arg Glu Phe Asn
                405                 410                 415
Asn Leu Glu Arg Arg Ile Glu Asn Leu Asn Lys Lys Met Glu Asp Gly
            420                 425                 430
Phe Leu Asp Val Trp Thr Tyr Asn Ala Glu Leu Leu Val Leu Met Glu
        435                 440                 445
Asn Glu Arg Thr Leu Asp Phe His Asp Ser Asn Val Lys Asn Leu Tyr
450                 455                 460
Asp Arg Val Arg Leu Gln Leu Arg Asp Asn Ala Lys Glu Leu Gly Asn
465                 470                 475                 480
Gly Cys Phe Glu Phe Tyr His Arg Cys Asp Asn Glu Cys Met Glu Ser
                485                 490                 495
Val Arg Asn Gly Thr Tyr Asp Tyr Pro Gln Tyr Ser Glu Glu Ala Arg
            500                 505                 510
Leu Lys Arg Glu Glu Ile Ser Gly Val Lys Leu Glu Ser Ile Gly Thr
        515                 520                 525
Tyr Gln Ile Leu Ser Ile Tyr Ser Thr Val Ala Ser Ser Leu Ala Leu
530                 535                 540
Ala Ile Met Val Ala Gly Leu Phe Leu Trp Met Cys Ser Asn Gly Ser
545                 550                 555                 560
Leu Gln Cys Arg Ile Cys Ile
            565

<210> SEQ ID NO 11
<211> LENGTH: 560
<212> TYPE: PRT
<213> ORGANISM: H5N1
<220> FEATURE:
<221> NAME/KEY: misc_feature
<222> LOCATION: (560)..(560)
<223> OTHER INFORMATION: Xaa can

```
                65                  70                  75                  80
Pro Met Cys Asp Glu Phe Leu Asn Val Pro Glu Trp Ser Tyr Ile Val
                        85                  90                  95
Glu Lys Ile Tyr Pro Ala Asn Asp Leu Cys Tyr Pro Gly Asn Phe Asn
                        100                 105                 110
Asp Tyr Glu Glu Leu Lys His Leu Leu Ser Arg Ile Asn His Phe Glu
                        115                 120                 125
Lys Ile Gln Ile Ile Pro Lys Ser Ser Trp Ser Asp His Glu Ala Ser
            130                 135                 140
Gly Val Ser Ser Ala Cys Pro Tyr Gln Gly Arg Ser Ser Phe Phe Arg
145                 150                 155                 160
Asn Val Val Trp Leu Thr Lys Lys Asp Asn Ala Tyr Pro Thr Ile Lys
                    165                 170                 175
Lys Ser Tyr Asn Asn Thr Asn Gln Glu Asp Leu Leu Ile Leu Trp Gly
                    180                 185                 190
Ile His His Pro Asn Asp Ala Ala Glu Gln Thr Arg Leu Tyr Gln Asn
            195                 200                 205
Pro Thr Thr Tyr Ile Ser Val Gly Thr Ser Thr Leu Asn Gln Arg Leu
            210                 215                 220
Val Pro Lys Ile Ala Thr Arg Ser Lys Val Asn Gly Gln Ser Gly Arg
225                 230                 235                 240
Met Glu Phe Phe Trp Thr Ile Leu Lys Ser Asn Asp Ala Ile Asn Phe
                    245                 250                 255
Glu Ser Asn Gly Asn Phe Ile Ala Pro Glu Asn Ala Tyr Lys Ile Val
                    260                 265                 270
Lys Lys Gly Asp Ser Thr Ile Met Lys Ser Glu Leu Glu Tyr Gly Asn
                275                 280                 285
Cys Asn Thr Lys Cys Gln Thr Pro Ile Gly Ala Ile Asn Ser Ser Met
            290                 295                 300
Pro Phe His Asn Ile His Pro Leu Thr Ile Gly Glu Cys Pro Lys Tyr
305                 310                 315                 320
Val Lys Ser Asn Arg Leu Val Leu Ala Thr Gly Leu Arg Asn Ser Pro
                325                 330                 335
Gln Gly Glu Arg Arg Lys Lys Arg Gly Leu Phe Gly Ala Ile Ala
                340                 345                 350
Gly Phe Ile Glu Gly Gly Trp Gln Gly Met Val Asp Gly Trp Tyr Gly
            355                 360                 365
Tyr His His Ser Asn Glu Gln Gly Ser Gly Tyr Ala Ala Asp Lys Glu
            370                 375                 380
Ser Thr Gln Lys Ala Ile Asp Gly Val Thr Asn Lys Val Asn Ser Ile
385                 390                 395                 400
Ile Asp Lys Met Asn Thr Gln Phe Glu Ala Val Gly Arg Glu Phe Asn
                405                 410                 415
Asn Leu Glu Arg Arg Ile Glu Asn Leu Asn Lys Lys Met Glu Asp Gly
                420                 425                 430
Phe Leu Asp Val Trp Thr Tyr Asn Ala Glu Leu Leu Val Leu Met Glu
                435                 440                 445
Asn Glu Arg Thr Leu Asp Phe His Asp Ser Asn Val Lys Asn Leu Tyr
            450                 455                 460
Asp Lys Val Arg Leu Gln Leu Arg Asp Asn Ala Lys Glu Leu Gly Asn
465                 470                 475                 480
Gly Cys Phe Glu Phe Tyr His Arg Cys Asp Asn Glu Cys Met Glu Ser
                485                 490                 495
```

-continued

Val Arg Asn Gly Thr Tyr Asp Tyr Pro Gln Tyr Ser Glu Glu Ala Arg
                500                 505                 510

Leu Lys Arg Glu Glu Ile Ser Gly Val Lys Leu Glu Ser Ile Gly Thr
        515                 520                 525

Tyr Gln Ile Leu Ser Ile Tyr Ser Thr Val Ala Ser Ser Leu Ala Leu
    530                 535                 540

Ala Ile Met Val Ala Gly Leu Phe Leu Trp Met Cys Ser Asn Gly Xaa
545                 550                 555                 560

<210> SEQ ID NO 12
<211> LENGTH: 544
<212> TYPE: PRT
<213> ORGANISM: H5N1
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (544)..(544)
<223> OTHER INFORMATION: Xaa can be any naturally occurring amino acid

<400> SEQUENCE: 12

Xaa Leu Leu Ala Ile Val Ser Ile Val Lys Ser Asp Gln Ile Cys Ile
1               5                   10                  15

Gly Tyr His Ala Asn Asn Ser Thr Glu Gln Val Asp Thr Ile Met Glu
            20                  25                  30

Lys Asn Val Thr Val Thr His Ala Gln Asp Ile Leu Glu Lys Thr His
        35                  40                  45

Asn Gly Lys Leu Cys Asn Leu Asp Gly Val Lys Pro Leu Ile Leu Arg
    50                  55                  60

Asp Cys Ser Val Ala Gly Trp Leu Leu Gly Asn Pro Met Cys Asp Glu
65                  70                  75                  80

Phe Leu Asp Val Pro Glu Trp Ser Tyr Ile Val Glu Lys Ile Asn Pro
                85                  90                  95

Ala Asn Asp Leu Cys Tyr Pro Gly Asn Phe Asn Asp Tyr Glu Glu Leu
            100                 105                 110

Lys His Leu Leu Ser Arg Ile Asn His Phe Glu Lys Ile Gln Ile Ile
        115                 120                 125

Pro Lys Asn Ser Trp Ser Asp His Glu Thr Ser Gly Val Ser Ser Ala
    130                 135                 140

Cys Pro Tyr Gln Gly Arg Ser Ser Phe Phe Arg Asn Val Val Trp Leu
145                 150                 155                 160

Thr Lys Lys Asn Thr Ala Tyr Pro Thr Ile Lys Lys Ser Tyr Asn Asn
                165                 170                 175

Thr Asn Gln Glu Asp Leu Leu Val Leu Trp Gly Ile His His Pro Asn
            180                 185                 190

Asp Ala Ala Glu Gln Thr Arg Leu Tyr Gln Asn Pro Thr Thr Tyr Ile
        195                 200                 205

Ser Val Gly Thr Ser Thr Leu Asn Gln Arg Leu Val Pro Lys Ile Ala
    210                 215                 220

Thr Arg Ser Lys Val Asn Gly Gln Ser Gly Arg Met Glu Phe Phe Trp
225                 230                 235                 240

Thr Ile Leu Lys Ser Asn Asp Ala Ile Asn Phe Glu Ser Asn Gly Asn
                245                 250                 255

Phe Ile Ala Pro Glu Asn Ala Tyr Lys Ile Val Lys Lys Gly Asp Ser
            260                 265                 270

-continued

```
Thr Ile Met Lys Ser Glu Leu Glu Tyr Gly Asn Cys Asn Thr Lys Cys
            275                 280                 285

Gln Thr Pro Ile Gly Ala Ile Asn Ser Ser Met Pro Phe His Asn Ile
        290                 295                 300

His Pro Leu Thr Ile Gly Glu Cys Pro Lys Tyr Val Lys Ser Asn Arg
305                 310                 315                 320

Leu Val Leu Ala Thr Gly Leu Arg Asn Ser Pro His Gly Glu Arg Arg
                325                 330                 335

Arg Lys Lys Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Glu Gln Gly Ser Gly Tyr Ala Ala Asp Lys Glu Ser Thr Gln Lys Ala
    370                 375                 380

Ile Asp Gly Val Thr Asn Lys Val Asn Ser Ile Ile Asp Lys Met Asn
385                 390                 395                 400

Thr Gln Phe Glu Ala Val Gly Arg Glu Phe Asn Asn Leu Glu Arg Arg
                405                 410                 415

Ile Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Leu
    450                 455                 460

Gln Leu Arg Asp Asn Ala Lys Glu Leu Gly Asn Gly Cys Phe Glu Phe
465                 470                 475                 480

Tyr His Arg Cys Asp Asn Glu Cys Met Glu Ser Val Arg Asn Gly Thr
                485                 490                 495

Tyr Asp Tyr Pro Gln Tyr Ser Glu Glu Ala Arg Leu Lys Arg Glu Glu
            500                 505                 510

Ile Ser Gly Val Lys Leu Glu Ser Ile Gly Thr Tyr Gln Ile Leu Ser
        515                 520                 525

Ile Tyr Ser Thr Val Ala Ser Ser Leu Ala Leu Ala Ile Met Val Xaa
    530                 535                 540
```

<210> SEQ ID NO 13
<211> LENGTH: 534
<212> TYPE: PRT
<213> ORGANISM: H5N1
<220> FEATURE:
<221> NAME/KEY: misc_feature
<222> LOCATION: (1)..(1)
<223> OTHER INFORMATION: Xaa can be any naturally occurring amino acid

<400> SEQUENCE: 13

```
Xaa Val Lys Ser Asp Gln Ile Cys Ile Gly Tyr His Ala Asn Asn Ser
1               5                   10                  15

Thr Glu Gln Val Asp Thr Ile Met Glu Lys Asn Val Thr Val Thr His
                20                  25                  30

Ala Gln Asp Ile Leu Glu Lys Thr His Asn Gly Lys Leu Cys Asn Leu
            35                  40                  45

Asp Gly Val Lys Pro Leu Ile Leu Arg Asp Cys Ser Val Ala Gly Trp
        50                  55                  60

Leu Leu Gly Asn Pro Met Cys Asp Glu Phe Leu Asn Val Glu Trp Ser
65                  70                  75                  80
```

```
Tyr Ile Val Glu Lys Ile Asn Pro Thr Asn Asp Leu Cys Tyr Pro Gly
             85                  90                  95

Asn Phe Asn Asp Tyr Glu Glu Leu Lys His Leu Leu Ser Arg Ile Asn
            100                 105                 110

His Phe Glu Lys Ile Gln Ile Ile Pro Lys Asn Tyr Trp Ser Asp His
            115                 120                 125

Glu Thr Ser Gly Val Ser Ser Ala Cys Pro Tyr Gln Gly Arg Pro Ser
            130                 135                 140

Phe Phe Arg Asn Val Val Trp Leu Thr Lys Asn Asn Ala Tyr Pro
145                 150                 155                 160

Thr Ile Lys Lys Ser Tyr Asn Asn Thr Asn Gln Glu Asp Leu Leu Val
                165                 170                 175

Leu Trp Gly Ile His His Pro Asn Asp Ala Ala Glu Gln Thr Arg Leu
            180                 185                 190

Tyr Gln Asn Pro Thr Thr Tyr Ile Ser Val Gly Thr Ser Thr Leu Asn
            195                 200                 205

Gln Arg Leu Val Pro Lys Ile Ala Thr Arg Ser Lys Val Asn Gly Gln
            210                 215                 220

Ser Gly Arg Met Glu Phe Phe Trp Thr Ile Leu Lys Ser Asn Asp Ala
225                 230                 235                 240

Ile Asn Phe Glu Ser Asn Gly Asn Phe Ile Ala Pro Glu Asn Ala Tyr
                245                 250                 255

Lys Ile Val Lys Lys Gly Asp Ser Thr Ile Met Lys Ser Glu Leu Glu
            260                 265                 270

Tyr Gly Asn Cys Asn Thr Lys Cys Gln Thr Pro Ile Gly Ala Ile Asn
            275                 280                 285

Ser Ser Met Pro Phe His Asn Ile His Pro Leu Thr Ile Gly Glu Cys
290                 295                 300

Pro Lys Tyr Val Lys Ser Asn Arg Leu Val Leu Ala Thr Gly Leu Arg
305                 310                 315                 320

Asn Ser Pro Gln Gly Glu Arg Arg Lys Arg Gly Leu Phe Gly
            325                 330                 335

Ala Ile Ala Gly Phe Ile Glu Gly Gly Trp Gln Gly Met Val Asp Gly
            340                 345                 350

Trp Tyr Gly Tyr His His Ser Asn Glu Gln Gly Ser Gly Tyr Ala Ala
            355                 360                 365

Asp Lys Glu Ser Thr Gln Lys Ala Ile Asp Gly Val Thr Asn Lys Val
            370                 375                 380

Asn Ser Ile Ile Asp Lys Met Asn Thr Gln Phe Glu Ala Val Gly Arg
385                 390                 395                 400

Glu Phe Asn Asn Leu Glu Arg Arg Ile Glu Asn Leu Asn Lys Lys Met
                405                 410                 415

Glu Asp Gly Phe Leu Asp Val Trp Thr Tyr Asn Ala Glu Leu Leu Val
            420                 425                 430

Leu Met Glu Asn Glu Arg Thr Leu Asp Phe His Asp Ser Asn Val Lys
            435                 440                 445

Asn Leu Tyr Asp Lys Val Arg Leu Gln Leu Arg Asp Asn Ala Lys Glu
            450                 455                 460

Leu Gly Asn Gly Cys Phe Glu Phe Tyr His Arg Cys Asp Asn Glu Cys
465                 470                 475                 480

Met Glu Ser Val Arg Asn Gly Thr Tyr Asp Tyr Pro Gln Tyr Ser Glu
                485                 490                 495

Glu Ala Arg Leu Lys Arg Glu Glu Ile Ser Gly Val Lys Leu Glu Ser
```

```
                500                 505                 510
Ile Gly Thr Tyr Gln Ile Leu Ser Ile Tyr Ser Thr Val Ala Ser Ser
            515                 520                 525

Leu Ala Leu Ala Ile Met
        530

<210> SEQ ID NO 14
<211> LENGTH: 548
<212> TYPE: PRT
<213> ORGANISM: H5N1
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (548)..(548)
<223> OTHER INFORMATION: Xaa can be any naturally occurring amino acid

<400> SEQUENCE: 14

Xaa Val Lys Ser Asp Gln Ile Cys Ile Gly Tyr His Ala Asn Asn Ser
1               5                   10                  15

Thr Glu Gln Val Asp Thr Ile Met Glu Lys Asn Val Thr Val Thr His
            20                  25                  30

Ala Gln Asp Ile Leu Glu Lys Thr His Asn Gly Lys Leu Cys Asn Leu
        35                  40                  45

Asp Gly Val Lys Pro Leu Ile Leu Arg Asp Cys Ser Val Ala Gly Trp
    50                  55                  60

Leu Leu Gly Asn Pro Met Cys Asp Lys Phe Leu Asn Val Pro Glu Trp
65                  70                  75                  80

Ser Tyr Ile Val Glu Lys Ile Asn Pro Thr Asn Asp Leu Cys Tyr Pro
                85                  90                  95

Gly Asn Phe Asn Asp Tyr Glu Glu Leu Lys His Leu Leu Ser Arg Ile
            100                 105                 110

Asn His Phe Glu Lys Ile Gln Ile Ile Pro Lys Asn Ser Trp Ser Asp
        115                 120                 125

His Glu Ala Ser Gly Val Ser Ser Ala Cys Pro Tyr Gln Gly Arg Ser
    130                 135                 140

Ser Phe Phe Arg Asn Val Val Trp Leu Thr Lys Lys Asn Asn Ala Tyr
145                 150                 155                 160

Pro Thr Ile Lys Lys Ser Tyr Asn Asn Thr Asn Gln Glu Asp Leu Leu
                165                 170                 175

Val Leu Trp Gly Ile His His Pro Asn Asp Ala Ala Glu Gln Thr Arg
            180                 185                 190

Leu Tyr Gln Asn Pro Thr Thr Tyr Ile Ser Val Gly Thr Ser Thr Leu
        195                 200                 205

Asn Gln Arg Leu Val Pro Lys Ile Ala Thr Arg Ser Lys Val Asn Gly
    210                 215                 220

Gln Ser Gly Arg Met Glu Phe Phe Trp Thr Ile Leu Lys Ser Asn Asp
225                 230                 235                 240

Ala Ile Asn Phe Glu Ser Asn Gly Asn Phe Ile Ala Pro Glu Asn Ala
                245                 250                 255

Tyr Lys Ile Val Lys Lys Gly Asp Ser Thr Ile Met Lys Ser Glu Leu
            260                 265                 270

Glu Tyr Gly Asp Cys Asn Thr Lys Cys Gln Thr Pro Ile Gly Ala Ile
        275                 280                 285

Asn Ser Ser Met Pro Phe His Asn Ile His Pro Leu Thr Ile Gly Glu
```

```
            290                 295                 300
Cys Pro Lys Tyr Val Lys Ser Asn Arg Leu Val Leu Ala Thr Gly Leu
305                 310                 315                 320

Arg Asn Ser Pro Gln Gly Glu Arg Arg Lys Lys Arg Gly Leu Phe
                325                 330                 335

Gly Ala Ile Ala Gly Phe Ile Glu Gly Gly Trp Gln Gly Met Val Asp
                340                 345                 350

Gly Trp Tyr Gly Tyr His His Ser Asn Glu Gln Gly Ser Gly Tyr Ala
                355                 360                 365

Ala Asp Lys Glu Ser Thr Gln Lys Ala Ile Asp Gly Val Thr Asn Lys
                370                 375                 380

Val Asn Ser Ile Ile Asp Lys Met Asn Thr Gln Phe Glu Ala Val Gly
385                 390                 395                 400

Arg Glu Phe Asn Asn Leu Glu Arg Arg Ile Glu Asn Leu Asn Lys Lys
                405                 410                 415

Met Glu Asp Gly Phe Leu Asp Val Trp Thr Tyr Asn Ala Glu Leu Leu
                420                 425                 430

Val Leu Met Glu Asn Glu Arg Thr Leu Asp Phe His Asp Ser Asn Val
                435                 440                 445

Lys Asn Leu Tyr Asp Lys Val Arg Leu Gln Leu Arg Asp Asn Ala Lys
450                 455                 460

Glu Leu Gly Asn Gly Cys Phe Glu Phe Tyr His Arg Cys Asp Asn Glu
465                 470                 475                 480

Cys Met Glu Ser Val Arg Asn Gly Thr Tyr Asp Tyr Pro Gln Tyr Ser
                485                 490                 495

Glu Glu Ala Arg Leu Lys Arg Glu Glu Ile Ser Gly Val Lys Leu Glu
                500                 505                 510

Ser Ile Gly Thr Tyr Gln Ile Leu Ser Ile Tyr Ser Thr Val Ala Ser
                515                 520                 525

Ser Leu Ala Leu Ala Ile Met Val Ala Gly Leu Phe Leu Trp Met Cys
                530                 535                 540

Ser Asn Gly Xaa
545

<210> SEQ ID NO 15
<211> LENGTH: 541
<212> TYPE: PRT
<213> ORGANISM: H5N1
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (541)..(541)
<223> OTHER INFORMATION: Xaa can be any naturally occurring amino acid

<400> SEQUENCE: 15

Xaa Ile Val Ser Ile Val Lys Ser Asp Gln Ile Cys Ile Gly Tyr His
1               5                   10                  15

Ala Asn Asn Ser Thr Glu Gln Val Asp Thr Ile Met Glu Lys Asn Val
                20                  25                  30

Thr Val Thr His Ala Gln Asp Ile Leu Glu Lys Thr His Asn Gly Lys
                35                  40                  45

Leu Cys Asn Leu Asp Gly Val Lys Pro Leu Ile Leu Arg Asp Cys Ser
50                  55                  60

Val Ala Gly Trp Leu Leu Gly Asn Pro Met Cys Asp Glu Phe Leu Asn
```

-continued

```
               65                  70                  75                  80
Val Pro Glu Trp Ser Tyr Ile Val Glu Lys Ile Asn Pro Thr Asn Asp
                    85                  90                  95
Leu Cys Tyr Pro Gly Asn Phe Asn Asp Tyr Glu Glu Leu Lys His Leu
                   100                 105                 110
Leu Ser Arg Ile Asn His Phe Glu Lys Ile Gln Ile Pro Lys Asn
                   115                 120                 125
Ser Trp Ser Asp His Glu Ala Ser Gly Val Ser Ala Cys Pro Tyr
           130                 135                 140
Gln Gly Arg Ser Ser Phe Phe Arg Asn Val Val Trp Leu Thr Lys Lys
145                 150                 155                 160
Asn Asn Ala Tyr Pro Thr Ile Lys Lys Ser Tyr Asn Asn Thr Asn Gln
                   165                 170                 175
Glu Asp Leu Leu Val Leu Trp Gly Ile His His Pro Asn Asp Ala Ala
               180                 185                 190
Glu Gln Thr Arg Leu Tyr Gln Asn Pro Thr Thr Tyr Ile Ser Val Gly
               195                 200                 205
Thr Ser Thr Leu Asn Gln Arg Leu Val Pro Lys Ile Ala Thr Arg Ser
       210                 215                 220
Lys Val Asn Gly Gln Ser Gly Arg Met Glu Phe Phe Trp Thr Ile Leu
225                 230                 235                 240
Lys Ser Asn Asp Ala Ile Asn Phe Glu Ser Asn Gly Asn Phe Ile Ala
                   245                 250                 255
Pro Glu Asn Ala Tyr Lys Ile Val Lys Lys Gly Asp Ser Thr Ile Met
                   260                 265                 270
Lys Ser Glu Leu Glu Tyr Gly Asp Cys Asn Thr Lys Cys Gln Thr Pro
           275                 280                 285
Ile Gly Ala Ile Asn Ser Ser Met Pro Phe His Asn Ile His Pro Leu
           290                 295                 300
Thr Ile Gly Glu Cys Pro Lys Tyr Val Lys Ser Asn Arg Leu Val Leu
305                 310                 315                 320
Ala Thr Gly Leu Arg Asn Ser Pro Gln Gly Glu Arg Arg Lys Lys
                   325                 330                 335
Arg Gly Leu Phe Gly Ala Ile Ala Gly Phe Ile Glu Gly Gly Trp Gln
               340                 345                 350
Gly Met Val Asp Gly Trp Tyr Gly Tyr His His Ser Asn Glu Gln Gly
           355                 360                 365
Ser Gly Tyr Ala Ala Asp Lys Glu Ser Thr Gln Lys Ala Ile Asp Gly
       370                 375                 380
Val Thr Asn Lys Val Asn Ser Ile Ile Asp Lys Met Asn Thr Gln Phe
385                 390                 395                 400
Glu Ala Val Gly Arg Glu Phe Asn Asn Leu Glu Arg Arg Ile Glu Asn
                   405                 410                 415
Leu Asn Lys Lys Met Glu Asp Gly Phe Leu Asp Val Trp Thr Tyr Asn
                   420                 425                 430
Ala Glu Leu Leu Val Leu Met Glu Asn Glu Arg Thr Leu Asp Phe His
               435                 440                 445
Asp Ser Asn Val Lys Asn Leu Tyr Asp Lys Val Arg Leu Gln Leu Arg
       450                 455                 460
Asp Asn Ala Lys Glu Leu Gly Asn Gly Cys Phe Glu Phe Tyr His Arg
465                 470                 475                 480
Cys Asp Asn Glu Cys Met Glu Ser Val Arg Asn Gly Thr Tyr Asp Tyr
                   485                 490                 495
```

```
Pro Gln Tyr Ser Glu Glu Ala Arg Leu Lys Arg Glu Ile Ser Gly
            500                 505                 510

Val Lys Leu Glu Ser Ile Gly Thr Tyr Gln Ile Leu Ser Ile Tyr Ser
515                 520                 525

Thr Val Ala Ser Ser Leu Ala Leu Ala Ile Met Val Xaa
            530                 535                 540

<210> SEQ ID NO 16
<211> LENGTH: 520
<212> TYPE: PRT
<213> ORGANISM: H5N1
<220> FEATURE:
<221> NAME/KEY: misc_feature
<222>

-continued

```
Asn Ser Ser Met Pro Phe His Asn Ile His Pro Leu Thr Ile Gly Glu
    290                 295                 300

Cys Pro Lys Tyr Val Lys Ser Asn Arg Leu Val Leu Ala Thr Gly Leu
305                 310                 315                 320

Arg Asn Ser Pro Gln Gly Glu Arg Arg Arg Lys Lys Arg Gly Leu Phe
                325                 330                 335

Gly Ala Ile Ala Gly Phe Ile Glu Gly Gly Trp Gln Gly Met Val Asp
            340                 345                 350

Gly Trp Tyr Gly Tyr His His Ser Asn Glu Gln Gly Ser Gly Tyr Ala
        355                 360                 365

Ala Asp Lys Glu Ser Thr Gln Lys Ala Ile Asp Gly Val Thr Asn Lys
    370                 375                 380

Val Asn Ser Ile Ile Asp Lys Met Asn Thr Gln Phe Glu Ala Val Gly
385                 390                 395                 400

Arg Glu Phe Asn Asn Leu Glu Arg Arg Ile Glu Asn Leu Asn Lys Lys
                405                 410                 415

Met Glu Asp Gly Phe Leu Asp Val Trp Thr Tyr Asn Ala Glu Leu Leu
            420                 425                 430

Val Leu Met Glu Asn Glu Arg Thr Leu Asp Phe His Asp Ser Asn Val
        435                 440                 445

Lys Asn Leu Tyr Asp Lys Val Arg Leu Gln Leu Arg Asp Asn Ala Lys
    450                 455                 460

Glu Leu Gly Asn Gly Cys Phe Glu Phe Tyr His Arg Cys Asp Asn Glu
465                 470                 475                 480

Cys Met Glu Ser Val Arg Asn Gly Thr Tyr Asp Tyr Pro Gln Tyr Ser
                485                 490                 495

Glu Glu Ala Arg Leu Lys Arg Glu Glu Ile Ser Gly Val Lys Leu Glu
            500                 505                 510

Ser Ile Gly Thr Tyr Gln Ile Leu
        515                 520
```

<210> SEQ ID NO 17
<211> LENGTH: 537
<212> TYPE: PRT
<213> ORGANISM: H5N1
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (537)..(537)
<223> OTHER INFORMATION: Xaa can be any naturally occurring amino acid

<400> SEQUENCE: 17

```
Xaa Ser Ile Val Lys Ser Asp Gln Ile Cys Ile Gly Tyr His Ala Asn
1               5                   10                  15

Asn Ser Thr Glu Gln Val Asp Thr Ile Met Glu Lys Asn Val Thr Val
            20                  25                  30

Thr His Ala Gln Asp Ile Leu Glu Lys Thr His Asn Gly Lys Leu Cys
        35                  40                  45

Asn Leu Asp Gly Val Lys Pro Leu Ile Leu Arg Asp Cys Ser Val Ala
    50                  55                  60

Gly Trp Leu Leu Gly Asn Pro Met Cys Asp Glu Phe Leu Asn Val Pro
65                  70                  75                  80

Glu Trp Ser Tyr Ile Val Glu Lys Ile Asn Pro Ala Asn Asp Leu Cys
                85                  90                  95
```

Tyr Pro Gly Asn Phe Asn Asp Tyr Glu Glu Leu Lys His Leu Leu Ser
            100                 105                 110

Arg Ile Asn His Phe Glu Lys Ile Gln Ile Ile Pro Lys Asn Ser Trp
            115                 120                 125

Ser Asp His Glu Ala Ser Gly Val Ser Ser Ala Cys Pro Tyr Gln Gly
130                 135                 140

Arg Ser Ser Phe Phe Arg Asn Val Val Trp Leu Thr Lys Lys Asn Asn
145                 150                 155                 160

Ala Tyr Pro Thr Ile Lys Lys Ser Tyr Asn Asn Thr Asn Gln Glu Asp
            165                 170                 175

Leu Leu Val Leu Trp Gly Ile His His Pro Asn Asp Glu Ala Glu Gln
            180                 185                 190

Thr Arg Leu Tyr Gln Asn Pro Thr Thr Tyr Ile Ser Val Gly Thr Ser
            195                 200                 205

Thr Leu Asn Gln Arg Leu Val Pro Lys Ile Ala Thr Arg Ser Lys Val
210                 215                 220

Asn Gly Gln Ser Gly Arg Met Glu Phe Phe Trp Thr Ile Leu Lys Ser
225                 230                 235                 240

Asn Asp Ala Ile Asn Phe Glu Ser Asn Gly Asn Phe Ile Ala Pro Glu
            245                 250                 255

Asn Ala Tyr Lys Ile Val Lys Lys Gly Asp Ser Thr Ile Met Lys Ser
            260                 265                 270

Glu Leu Glu Tyr Gly Asn Cys Asn Thr Lys Cys Gln Thr Pro Ile Gly
            275                 280                 285

Ala Ile Asn Ser Ser Met Pro Phe His Asn Ile His Pro Leu Thr Ile
            290                 295                 300

Gly Glu Cys Pro Lys Tyr Val Lys Ser Asn Arg Leu Val Leu Ala Thr
305                 310                 315                 320

Gly Leu Arg Asn Ser Pro Gln Gly Glu Arg Arg Lys Lys Arg Gly
            325                 330                 335

Leu Phe Gly Ala Ile Ala Gly Phe Ile Glu Gly Gly Trp Gln Gly Met
            340                 345                 350

Val Asp Gly Trp Tyr Gly Tyr His His Ser Asn Glu Gln Gly Ser Gly
            355                 360                 365

Tyr Ala Ala Asp Lys Glu Ser Thr Gln Lys Ala Ile Asp Gly Val Thr
            370                 375                 380

Asn Lys Val Asn Ser Ile Ile Asp Lys Met Asn Thr Gln Phe Glu Ala
385                 390                 395                 400

Val Gly Arg Glu Phe Asn Asn Leu Glu Arg Arg Ile Glu Asn Leu Asn
            405                 410                 415

Lys Lys Met Glu Asp Gly Phe Leu Asp Val Trp Thr Tyr Asn Ala Glu
            420                 425                 430

Leu Leu Val Leu Met Glu Asn Glu Arg Thr Leu Asp Phe His Asp Ser
            435                 440                 445

Asn Val Lys Asn Leu Tyr Asp Lys Val Arg Leu Gln Leu Arg Asp Asn
            450                 455                 460

Ala Lys Glu Leu Gly Asn Gly Cys Phe Glu Phe Tyr His Arg Cys Asp
465                 470                 475                 480

Asn Glu Cys Met Glu Ser Val Arg Asn Gly Thr Tyr Asp Tyr Pro Gln
            485                 490                 495

Tyr Ser Glu Glu Ala Arg Leu Lys Arg Glu Glu Ile Ser Gly Val Lys
            500                 505                 510

```
Leu Glu Ser Ile Gly Thr Tyr Gln Ile Leu Ser Ile Tyr Ser Thr Val
            515                 520                 525

Ala Ser Ser Leu Ala Leu Ala Ile Xaa
    530                 535

<210> SEQ ID NO 18
<211> LENGTH: 528
<212> TYPE: PRT
<213> ORGANISM: H5N1
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (528)..(528)
<223> OTHER INFORMATION: Xaa can be any naturally occurring amino acid

<400> SEQUENCE: 18

Xaa Ile Val Ser Ile Val Lys Ser Asp Gln Ile Cys Ile Gly Tyr His
1               5                  10                  15

Ala Asn Asn Ser Thr Glu Gln Val Asp Thr Ile Met Glu Lys Asn Val
            20                  25                  30

Thr Val Thr His Ala Gln Asp Ile Leu Glu Lys Thr His Asn Gly Lys
        35                  40                  45

Leu Cys Asn Leu Asp Gly Val Lys Pro Leu Ile Leu Arg Asp Cys Ser
    50                  55                  60

Val Ala Gly Trp Leu Leu Gly Asn Pro Met Cys Asp Glu Phe Leu Asn
65                  70                  75                  80

Val Pro Glu Trp Ser Tyr Ile Val Glu Lys Ile Asn Pro Ala Asn Asp
                85                  90                  95

Leu Cys Tyr Pro Gly Asn Phe Asn Asp Tyr Glu Glu Leu Lys His Leu
            100                 105                 110

Leu Ser Arg Ile Asn His Phe Glu Lys Ile Gln Ile Ile Pro Lys Asn
        115                 120                 125

Ser Trp Ser Asp His Glu Ala Ser Gly Val Ser Ser Ala Cys Pro Tyr
    130                 135                 140

Gln Gly Arg Ser Ser Phe Phe Arg Asn Val Val Trp Leu Thr Lys Lys
145                 150                 155                 160

Asn Asn Ala Tyr Pro Thr Ile Lys Lys Ser Tyr Asn Asn Thr Asn Gln
                165                 170                 175

Glu Asp Leu Leu Val Leu Trp Gly Ile His His Pro Asn Asp Ala Ala
            180                 185                 190

Glu Gln Thr Arg Leu Tyr Gln Asn Pro Thr Thr Tyr Ile Ser Val Gly
        195                 200                 205

Thr Ser Thr Leu Asn Gln Arg Leu Val Pro Lys Ile Ala Asn Arg Ser
    210                 215                 220

Lys Val Asn Gly Gln Ser Gly Arg Met Glu Phe Phe Trp Thr Ile Leu
225                 230                 235                 240

Lys Ser Asn Asp Ala Ile Asn Phe Glu Ser Asn Gly Asn Phe Ile Ala
                245                 250                 255

Pro Glu Asn Ala Tyr Lys Ile Val Lys Lys Gly Asp Ser Thr Ile Met
            260                 265                 270

Lys Ser Glu Leu Glu Tyr Gly Asn Cys Asn Thr Lys Cys Gln Thr Pro
        275                 280                 285

Ile Gly Ala Ile Asn Ser Ser Met Pro Phe His Asn Ile His Pro Leu
    290                 295                 300
```

```
Thr Ile Gly Glu Cys Pro Lys Tyr Val Lys Ser Asn Arg Leu Val Leu
305                 310                 315                 320

Ala Thr Gly Leu Arg Asn Ser Pro Gln Gly Glu Arg Arg Lys Lys
            325                 330                 335

Arg Gly Leu Phe Gly Ala Ile Ala Gly Phe Ile Glu Gly Gly Trp Gln
            340                 345                 350

Gly Met Val Asp Gly Trp Tyr Gly Tyr His His Ser Asn Glu Gln Gly
            355                 360                 365

Ser Gly Tyr Ala Ala Asp Lys Glu Ser Thr Gln Lys Ala Ile Asp Gly
            370                 375                 380

Val Thr Asn Lys Val Asn Ser Ile Ile Asp Lys Met Asn Thr Gln Phe
385                 390                 395                 400

Glu Ala Val Gly Arg Glu Phe Asn Asn Leu Glu Arg Arg Ile Glu Asn
                405                 410                 415

Leu Asn Lys Lys Met Glu Asp Gly Phe Leu Asp Val Trp Thr Tyr Asn
            420                 425                 430

Ala Glu Leu Leu Val Leu Met Glu Asn Glu Arg Thr Leu Asp Phe His
            435                 440                 445

Asp Ser Asn Val Lys Asn Leu Tyr Asp Lys Val Arg Leu Gln Leu Arg
450                 455                 460

Asp Asn Ala Lys Glu Leu Gly Asn Gly Cys Phe Glu Phe Tyr His Arg
465                 470                 475                 480

Cys Asp Asn Glu Cys Met Glu Ser Val Arg Asn Gly Thr Tyr Asp Tyr
                485                 490                 495

Pro Gln Tyr Ser Glu Glu Ala Arg Leu Lys Arg Glu Glu Ile Ser Gly
            500                 505                 510

Val Lys Leu Glu Ser Ile Gly Thr Tyr Gln Ile Leu Ser Ile Tyr Xaa
            515                 520                 525

<210> SEQ ID NO 19
<211> LENGTH: 535
<212> TYPE: PRT
<213> ORGANISM: H5N1
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (535)..(535)
<223> OTHER INFORMATION: Xaa can be any naturally occurring amino acid

<400> SEQUENCE: 19

Xaa Val Lys Ser Asp Gln Ile Cys Ile Gly Tyr His Ala Asn Asn Ser
1               5                   10                  15

Thr Glu Gln Val Asp Thr Ile Met Glu Lys Asn Val Thr Val Thr His
            20                  25                  30

Ala Gln Asp Ile Leu Glu Lys Thr His Asn Gly Lys Leu Cys Asn Leu
        35                  40                  45

Asp Gly Val Lys Pro Leu Ile Leu Arg Asp Cys Ser Val Ala Gly Trp
    50                  55                  60

Leu Leu Gly Asn Pro Met Cys Asp Glu Phe Leu Asn Val Pro Glu Trp
65                  70                  75                  80

Ser Tyr Ile Val Glu Lys Ile Asn Pro Ala Asn Asp Leu Cys Tyr Pro
                85                  90                  95

Gly Asn Phe Asn Asp Tyr Glu Glu Leu Lys His Leu Leu Ser Arg Ile
            100                 105                 110
```

```
Asn His Phe Glu Lys Ile Gln Ile Ile Pro Lys Asn Ser Trp Ser Asp
            115                 120                 125
His Glu Ala Ser Gly Val Ser Ser Ala Cys Pro Tyr Gln Gly Arg Ser
130                 135                 140
Ser Phe Phe Arg Asn Val Val Trp Leu Thr Lys Lys Asp Asn Ala Tyr
145                 150                 155                 160
Pro Thr Ile Lys Arg Ser Tyr Asn Asn Thr Asn Gln Glu Asp Leu Leu
                165                 170                 175
Val Leu Trp Gly Ile His His Pro Asn Asp Ala Ala Glu Gln Thr Arg
            180                 185                 190
Leu Tyr Gln Asn Pro Thr Thr Tyr Ile Ser Val Gly Thr Ser Thr Leu
    195                 200                 205
Asn Gln Arg Leu Val Pro Lys Ile Ala Thr Arg Ser Lys Val Asn Gly
210                 215                 220
Gln Ser Gly Arg Met Glu Phe Phe Trp Thr Ile Leu Lys Ser Asn Asp
225                 230                 235                 240
Ala Ile Asn Phe Glu Ser Asn Gly Asn Phe Ile Ala Pro Glu Asn Ala
                245                 250                 255
Tyr Lys Ile Val Lys Lys Gly Asp Ser Thr Ile Met Lys Ser Glu Leu
            260                 265                 270
Glu Tyr Gly Asn Cys Asn Thr Lys Cys Gln Thr Pro Ile Gly Ala Ile
    275                 280                 285
Asn Ser Ser Met Pro Phe His Asn Ile His Pro Leu Thr Ile Gly Glu
290                 295                 300
Cys Pro Lys Tyr Val Lys Ser Asn Arg Leu Val Leu Ala Thr Gly Leu
305                 310                 315                 320
Arg Asn Ser Pro Gln Gly Glu Arg Arg Lys Lys Arg Gly Leu Phe
                325                 330                 335
Gly Ala Ile Ala Gly Phe Ile Glu Gly Gly Trp Gln Gly Met Val Asp
            340                 345                 350
Gly Trp Tyr Gly Tyr His His Ser Asn Glu Gln Gly Ser Gly Tyr Ala
    355                 360                 365
Ala Asp Lys Glu Ser Thr Gln Lys Ala Ile Asp Gly Val Thr Asn Lys
370                 375                 380
Val Asn Ser Ile Ile Asp Lys Met Asn Thr Gln Phe Glu Ala Val Gly
385                 390                 395                 400
Arg Glu Phe Asn Asn Leu Glu Arg Arg Ile Glu Asn Leu Asn Lys Lys
                405                 410                 415
Met Glu Asp Gly Phe Leu Asp Val Trp Thr Tyr Asn Ala Glu Leu Leu
            420                 425                 430
Val Leu Met Glu Asn Glu Arg Thr Leu Asp Phe His Asp Ser Asn Val
    435                 440                 445
Lys Asn Leu Tyr Asp Lys Val Arg Leu Gln Leu Arg Asp Asn Ala Lys
450                 455                 460
Glu Leu Gly Asn Gly Cys Phe Glu Phe Tyr His Arg Cys Asp Asn Glu
465                 470                 475                 480
Cys Met Glu Ser Val Arg Asn Gly Thr Tyr Asp Tyr Pro Gln Tyr Ser
                485                 490                 495
Glu Glu Ala Arg Leu Lys Arg Glu Glu Ile Ser Gly Val Lys Leu Glu
            500                 505                 510
Ser Ile Gly Thr Tyr Gln Ile Leu Ser Ile Tyr Ser Thr Val Ala Ser
    515                 520                 525

Ser Leu Ala Leu Ala Ile Xaa
```

<210> SEQ ID NO 20
<211> LENGTH: 568
<212> TYPE: PRT
<213> ORGANISM: H5N1

<400> SEQUENCE: 20

Met Glu Lys Ile Val Leu Leu Leu Ala Ile Val Ser Leu Val Lys Ser
1 5 10 15

Asp Gln Ile Cys Ile Gly Tyr His Ala Asn Asn Ser Thr Glu Gln Val
20 25 30

Asp Thr Ile Met Glu Lys Asn Val Thr Val Thr His Ala Gln Asp Ile
35 40 45

Leu Glu Lys Thr His Asn Gly Lys Leu Cys Asp Leu Gly Gly Val Lys
50 55 60

Pro Leu Ile Leu Arg Asp Cys Ser Val Ala Gly Trp Leu Leu Gly Asn
65 70 75 80

Pro Met Cys Asp Glu Phe Pro Asn Val Ser Glu Trp Ser Tyr Ile Val
85 90 95

Glu Lys Ile Asn Pro Ala Asn Asp Leu Cys Tyr Pro Gly Asn Phe Asn
100 105 110

Asn Tyr Glu Glu Leu Lys His Leu Leu Ser Arg Ile Asn Arg Phe Glu
115 120 125

Lys Ile Gln Ile Ile Pro Lys Ser Ser Trp Pro Asp His Glu Ala Ser
130 135 140

Leu Gly Val Ser Ser Ala Cys Pro Tyr Gln Gly Gly Pro Ser Phe Tyr
145 150 155 160

Arg Asn Val Val Trp Leu Ile Lys Lys Asn Asp Thr Tyr Pro Thr Ile
165 170 175

Lys Glu Ser Tyr His Asn Thr Asn Gln Glu Asp Leu Leu Val Leu Trp
180 185 190

Gly Ile His His Pro Asn Asn Glu Glu Glu Gln Lys Arg Ile Tyr Lys
195 200 205

Asn Pro Thr Thr Tyr Val Ser Val Gly Thr Ser Thr Leu Asn Gln Arg
210 215 220

Leu Val Pro Lys Ile Ala Thr Arg Ser Lys Val Asn Gly Gln Ser Gly
225 230 235 240

Arg Val Glu Phe Phe Trp Thr Ile Leu Lys Ser Asn Asp Thr Ile Asn
245 250 255

Phe Glu Ser Asn Gly Asn Phe Ile Ala Pro Glu Asn Ala Tyr Lys Ile
260 265 270

Val Lys Lys Gly Asp Ser Thr Ile Met Lys Ser Glu Leu Glu Tyr Gly
275 280 285

Asn Cys Ser Thr Lys Cys Gln Thr Pro Ile Gly Ala Ile Asn Thr Ser
290 295 300

Met Pro Phe His Asn Ile His Pro Leu Thr Ile Gly Glu Cys Pro Lys
305 310 315 320

Tyr Val Lys Ser Asn Arg Leu Val Leu Ala Thr Gly Leu Arg Asn Ser
325 330 335

Pro Gln Gly Glu Gly Arg Arg Lys Lys Arg Gly Leu Phe Gly Ala Ile
340 345 350

Ala Gly Phe Ile Glu Gly Gly Trp Gln Gly Met Val Asp Gly Trp Tyr
355 360 365

```
Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Lys Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Arg Asn Leu
450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Arg Cys Asp Asn Glu Cys Met Glu
                485                 490                 495

Ser Val Arg Asn Gly Thr Tyr Asp Tyr Pro Gln Tyr Ser Glu Glu Ala
                500                 505                 510

Arg Leu Lys Arg Glu Glu Ile Ser Gly Val Lys Leu Glu Ser Ile Gly
                515                 520                 525

Thr Tyr Gln Ile Leu Ser Ile Tyr Ser Thr Val Ala Ser Ser Leu Ala
            530                 535                 540

Leu Ala Ile Met Val Ala Gly Leu Phe Leu Trp Met Cys Ser Asn Gly
545                 550                 555                 560

Ser Leu Gln Cys Arg Ile Cys Ile
                565

<210> SEQ ID NO 21
<211> LENGTH: 568
<212> TYPE: PRT
<213> ORGANISM: H5N1
<220> FEATURE:
<221> NAME/KEY

```
            145                 150                 155                 160
Arg Asn Val Val Trp Leu Ile Lys Lys Asn Asn Thr Tyr Pro Thr Ile
                        165                 170                 175

Lys Glu Ser Tyr His Asn Thr Asn Gln Glu Asp Leu Leu Val Leu Trp
                    180                 185                 190

Gly Ile His His Pro Asn Asp Glu Glu Gln Thr Arg Ile Tyr Lys
                195                 200                 205

Asn Pro Thr Thr Tyr Ile Ser Val Gly Thr Ser Thr Leu Asn Gln Arg
210                 215                 220

Leu Val Pro Lys Ile Ala Thr Arg Ser Lys Val Asn Gly Gln Ser Gly
225                 230                 235                 240

Arg Val Glu Phe Phe Trp Thr Ile Leu Lys Ser Asn Asp Thr Ile Asn
                    245                 250                 255

Phe Glu Ser Asn Gly Asn Phe Ile Ala Pro Glu Asn Ala Tyr Lys Ile
                260                 265                 270

Val Lys Lys Gly Asp Ser Thr Ile Met Lys Ser Glu Leu Glu Tyr Gly
            275                 280                 285

Asn Cys Ser Thr Lys Cys Gln Thr Pro Val Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Gly Glu Gly Arg Arg Lys Lys Arg Gly Leu Phe Gly Ala Ile
                340                 345                 350

Ala Gly Phe Ile Glu Gly Gly Trp Gln Gly Met Val Asp Gly Trp Tyr
                355                 360                 365

Gly Tyr His His Ser Asn Xaa Gln Gly Ser Gly Tyr Ala Ala Asp Arg
                370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Lys Arg Ile Glu Asn Leu Asn Lys Lys Met Glu Asp
                420                 425                 430

Gly Phe Leu Asp Val Trp Thr Tyr Asn Ala Glu Leu Leu Val Leu Met
                435                 440                 445

Glu Asn Glu Arg Thr Leu Asp Phe His Asp Ser Asn Val Lys Asn Leu
450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Arg Cys Asp Asn Glu Cys Ile Glu
                485                 490                 495

Ser Val Arg Asn Gly Thr Tyr Asp Tyr Pro Gln Tyr Ser Glu Glu Ala
                500                 505                 510

Arg Leu Lys Arg Glu Glu Ile Ser Gly Val Lys Leu Glu Ser Ile Gly
                515                 520                 525

Thr Tyr Gln Ile Leu Ser Ile Tyr Ser Thr Val Ala Ser Ser Leu Ala
                530                 535                 540

Leu Ala Ile Ile Val Ala Gly Leu Phe Leu Trp Met Cys Ser Asn Gly
545                 550                 555                 560

Ser Leu Gln Cys Arg Ile Cys Ile
                565
```

```
<210> SEQ ID NO 22
<211> LENGTH: 568
<212> TYPE: PRT
<213> ORGANISM: H5N1

<400> SEQUENCE: 22
```

Met Glu Lys Ile Val Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
            35                  40                  45

Leu Glu Lys Thr His Asn Gly Lys Leu Cys Asp Leu Asp Gly Val Lys
50                  55                  60

Pro Leu Ile Leu Arg Asp Cys Ser Val Ala Gly Trp Leu Leu Gly Asn
65                  70                  75                  80

Pro Met Cys Asp Glu Phe Pro Asn Val Ser Glu Trp Ser Tyr Ile Val
                85                  90                  95

Glu Lys Ile Asn Pro Ala Asn Asp Leu Cys Tyr Pro Gly Asn Phe Asn
            100                 105                 110

Asn Tyr Glu Glu Leu Lys His Leu Leu Ser Arg Ile Asn Arg Phe Glu
        115                 120                 125

Lys Ile Lys Ile Ile Pro Lys Ser Ser Trp Pro Asp His Glu Ala Ser
130                 135                 140

Leu Gly Val Ser Ser Ala Cys Pro Tyr Gln Arg Gly Pro Ser Phe Tyr
145                 150                 155                 160

Arg Asn Val Val Trp Leu Ile Lys Lys Asn Asn Thr Tyr Pro Thr Ile
                165                 170                 175

Lys Lys Ser Tyr His Asn Thr Asn Gln Glu Asp Leu Leu Val Leu Trp
            180                 185                 190

Gly Ile His His Pro Asn Asp Glu Glu Glu Gln Thr Arg Ile Tyr Lys
        195                 200                 205

Asn Pro Thr Thr Tyr Ile Ser Val Gly Thr Ser Thr Leu Asn Gln Arg
210                 215                 220

Leu Val Pro Lys Ile Ala Thr Arg Ser Lys Val Asn Gly Gln Ser Gly
225                 230                 235                 240

Arg Val Glu Phe Phe Trp Thr Ile Leu Lys Ser Asn Asp Thr Ile Asn
                245                 250                 255

Phe Glu Ser Asn Gly Asn Phe Ile Ala Pro Glu Asn Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Ile Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Gly Glu Gly Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys

```
                370              375             380
Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Lys Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Arg Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Met Ala Gly Leu Phe Leu Trp Met Cys Ser Asn Gly
545                 550                 555                 560

Ser Leu Gln Cys Arg Ile Cys Ile
                565

<210> SEQ ID NO 23
<211> LENGTH: 568
<212> TYPE: PRT
<213>

```
Lys Glu Ser Tyr His Asn Thr Asn Gln Glu Asp Leu Leu Val Leu Trp
            180                 185                 190

Gly Ile His His Pro Asn Asp Glu Glu Gln Thr Arg Ile Tyr Lys
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Arg Gly
225                 230                 235                 240

Arg Val Glu Phe Phe Trp Thr Ile Leu Lys Ser Asn Asp Thr Ile Asn
                245                 250                 255

Phe Glu Ser Asn Gly Asn Phe Ile Ala Pro Glu Asn Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Ile Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Gly Glu Gly Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Lys Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Arg Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Met Ala Gly Leu Phe Leu Trp Met Cys Ser Asn Gly
545                 550                 555                 560

Ser Leu Gln Cys Arg Ile Cys Ile
                565

<210> SEQ ID NO 24
<211> LENGTH: 568
<212> TYPE: PRT
```

<213> ORGANISM: H5N1

<400> SEQUENCE: 24

Met Glu Lys Ile Val Leu Leu Leu Ala Ile Val Ser Leu Val Lys Ser
1 5 10 15

Asp Gln Ile Cys Ile Gly Tyr His Ala Asn Asn Ser Thr Glu Gln Val
20 25 30

Asp Thr Ile Met Glu Lys Asn Val Thr Val Thr His Ala Gln Asp Ile
35 40 45

Leu Glu Lys Thr His Asn Gly Lys Leu Cys Asp Leu Asp Gly Val Lys
50 55 60

Pro Leu Ile Leu Arg Asp Cys Ser Val Ala Gly Trp Leu Leu Gly Asn
65 70 75 80

Pro Met Cys Asp Glu Phe Pro Asn Val Ser Glu Trp Ser Tyr Ile Val
85 90 95

Glu Lys Ile Asn Pro Ala Asn Asp Leu Cys Tyr Pro Gly Asn Phe Asn
100 105 110

Asn Tyr Glu Glu Leu Lys His Leu Leu Ser Arg Ile Asn Arg Phe Glu
115 120 125

Lys Ile Gln Ile Ile Pro Lys Ser Ser Trp Pro Asp His Glu Ala Ser
130 135 140

Leu Gly Val Ser Ser Ala Cys Pro Tyr Gln Gly Glu Pro Ser Phe Tyr
145 150 155 160

Arg Asn Val Val Trp Leu Ile Lys Lys Asn Asn Thr Tyr Pro Thr Ile
165 170 175

Lys Glu Ser Tyr His Asn Thr Asn Gln Glu Asp Leu Leu Val Leu Trp
180 185 190

Gly Ile His His Pro Asn Asp Glu Glu Glu Gln Lys Arg Ile Tyr Lys
195 200 205

Asn Pro Thr Thr Tyr Ile Ser Val Gly Thr Ser Thr Leu Asn Gln Arg
210 215 220

Leu Val Pro Lys Ile Ala Thr Arg Pro Lys Val Asn Gly Gln Ser Gly
225 230 235 240

Arg Val Glu Phe Phe Trp Thr Ile Leu Lys Ser Asn Asp Thr Ile Asn
245 250 255

Phe Glu Ser Asn Gly Asn Phe Ile Ala Pro Lys Asn Ala Tyr Lys Ile
260 265 270

Val Lys Lys Gly Ser Ser Thr Ile Met Lys Ser Glu Leu Glu Tyr Gly
275 280 285

Asn Cys Ser Thr Lys Cys Gln Thr Pro Ile Gly Ala Ile Asn Ser Ser
290 295 300

Met Pro Phe His Asn Ile His Pro Leu Thr Ile Gly Glu Cys Pro Lys
305 310 315 320

Tyr Val Lys Ser Asn Arg Leu Val Leu Ala Thr Gly Leu Arg Asn Ser
325 330 335

Pro Gln Gly Glu Gly Arg Arg Lys Lys Arg Gly Leu Phe Gly Ala Ile
340 345 350

Ala Gly Phe Ile Glu Gly Gly Trp Gln Gly Met Val Asp Gly Trp Tyr
355 360 365

Gly Tyr His His Ser Asn Glu Gln Gly Thr Gly Tyr Ala Ala Asp Lys
370 375 380

Glu Ser Thr Gln Lys Ala Ile Asp Gly Val Thr Asn Lys Val Asn Ser
385 390 395 400

```
Ile Ile Asp Lys Met Asn Thr Gln Phe Glu Ala Val Gly Arg Glu Phe
                405                 410                 415

Asn Asn Leu Glu Lys Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Arg Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Lys Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Thr Ser Ser Leu Ala
    530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 25
<211> LENGTH: 556
<212> TYPE: PRT
<213> ORGANISM: H5N1
<220> FEATURE:
<221> NAME/KEY: misc_feature
<222> LOCATION: (556)..(556)
<223> OTHER INFORMATION: Xaa can be any naturally occurring amino acid

<400> SEQUENCE: 25

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Pro Asn Val Ser Glu Trp Ser Tyr Ile Val
                85                  90                  95

Glu Lys Thr Asn Pro Ala Asn Asp Leu Cys Tyr Pro Gly Asn Phe Asn
            100                 105                 110

Asn Tyr Glu Glu Leu Lys His Leu Leu Ser Arg Ile Asn Arg Phe Glu
        115                 120                 125

Lys Ile Lys Ile Ile Pro Lys Ser Ser Trp Pro Asp His Glu Ala Ser
    130                 135                 140

Leu Gly Val Ser Ser Ala Cys Pro Tyr Gln Gly Arg Pro Ser Phe Tyr
145                 150                 155                 160

Arg Asn Val Val Trp Leu Ile Lys Lys Asn Asn Thr Tyr Pro Thr Ile
                165                 170                 175

Lys Glu Ser Tyr His Asn Thr Asn Gln Glu Asp Leu Leu Val Leu Trp
```

```
                180             185             190
Gly Ile His His Pro Asn Asp Glu Glu Gln Thr Arg Ile Tyr Lys
                195                 200                 205
Asn Pro Thr Thr Tyr Ile Ser Ile Gly Thr Ser Thr Leu Asn Gln Arg
    210                 215                 220
Leu Ile Pro Lys Ile Ala Thr Arg Ser Lys Val Asn Gly Gln Ser Gly
225                 230                 235                 240
Arg Val Glu Phe Phe Trp Thr Ile Leu Lys Ser Asn Asp Thr Ile Asn
                245                 250                 255
Phe Glu Ser Asn Gly Asn Phe Ile Ala Pro Glu Asn Ala Tyr Lys Ile
                260                 265                 270
Val Lys Lys Gly Asp Ser Thr Ile Met Lys Ser Glu Leu Glu Tyr Gly
                275                 280                 285
Asn Cys Asn Thr Lys Cys Gln Thr Pro Ile Gly Ala Ile Asn Ser Ser
                290                 295                 300
Met Pro Phe His Asn Ile His Pro Leu Thr Ile Gly Glu Cys Pro Lys
305                 310                 315                 320
Tyr Val Lys Ser Asn Arg Leu Val Leu Ala Thr Gly Leu Arg Asn Ser
                325                 330                 335
Pro Gln Gly Glu Gly Arg Arg Lys Lys Arg Gly Leu Phe Gly Ala Ile
                340                 345                 350
Ala Gly Phe Ile Glu Gly Gly Trp Gln Gly Met Val Asp Gly Trp Tyr
                355                 360                 365
Gly Tyr His His Ser Asn Glu Gln Gly Ser Gly Tyr Ala Ala Asp Lys
                370                 375                 380
Glu Ser Thr Gln Lys Ala Ile Asp Gly Val Thr Asn Lys Val Asn Ser
385                 390                 395                 400
Ile Ile Asp Lys Met Asn Thr Gln Phe Glu Ala Val Gly Arg Glu Phe
                405                 410                 415
Asn Asn Leu Glu Lys Arg Ile Glu Asn Leu Asn Lys Lys Met Glu Asp
                420                 425                 430
Gly Phe Leu Asp Val Trp Thr Tyr Asn Ala Glu Leu Leu Val Leu Met
                435                 440                 445
Glu Asn Glu Arg Thr Leu Asp Phe His Asp Ser Asn Val Lys Asn Leu
                450                 455                 460
Tyr Asp Lys Val Arg Leu Gln Leu Arg Asp Asn Ala Lys Glu Leu Gly
465                 470                 475                 480
Asn Gly Cys Phe Glu Phe Tyr His Arg Cys Asp Asn Glu Cys Met Glu
                485                 490                 495
Ser Val Arg Asn Gly Thr Tyr Asp Tyr Pro Gln Tyr Ser Glu Glu Ala
                500                 505                 510
Arg Leu Lys Arg Glu Glu Ile Ser Gly Val Lys Leu Glu Ser Ile Gly
                515                 520                 525
Thr Tyr Gln Ile Leu Ser Ile Tyr Ser Thr Val Ala Ser Ser Leu Ala
                530                 535                 540
Leu Ala Ile Met Met Ala Gly Leu Phe Leu Trp Xaa
545                 550                 555

<210> SEQ ID NO 26
<211> LENGTH: 554
<212> TYPE: PRT
<213> ORGANISM: H5N1
<220> FEATURE:
<221> NAME/KEY: misc_feature
<222> LOCATION: (1)..(1)
```

<223> OTHER INFORMATION: Xaa can be any naturally occurring amino acid
<220> FEATURE:
<221> NAME/KEY: misc_feature
<222> LOCATION: (554)..(554)
<223> OTHER INFORMATION: Xaa can be any naturally occurring amino acid

<400> SEQUENCE: 26

```
Xaa Leu Leu Ala Ile Val Ser Leu Val Lys Ser Asp Gln Ile Cys Ile
1               5                   10                  15

Gly Tyr His Ala Asn Asn Ser Thr Glu Gln Val Asp Thr Ile Met Glu
            20                  25                  30

Lys Asn Val Thr Val Thr His Ala Gln Asp Ile Leu Glu Lys Thr His
        35                  40                  45

Asn Gly Lys Leu Cys Asp Leu Asp Gly Val Lys Pro Leu Ile Leu Arg
    50                  55                  60

Asp Cys Ser Val Ala Gly Trp Leu Leu Gly Asn Pro Met Cys Asp Glu
65                  70                  75                  80

Phe Pro Asn Val Ser Glu Trp Ser Tyr Ile Val Glu Lys Ile Asn Pro
                85                  90                  95

Ala Asn Asp Leu Cys Tyr Pro Gly Asn Phe Asn Asn Tyr Glu Glu Leu
            100                 105                 110

Lys His Leu Leu Ser Arg Ile Asn Arg Phe Glu Lys Ile Gln Ile Ile
        115                 120                 125

Pro Lys Ser Ser Trp Pro Asp His Glu Ala Ser Leu Gly Val Ser Ser
    130                 135                 140

Ala Cys Pro Tyr Gln Gly Glu Pro Ser Phe Tyr Arg Asn Val Val Trp
145                 150                 155                 160

Leu Ile Lys Lys Asn Asn Thr Tyr Pro Thr Ile Lys Glu Asn Tyr His
                165                 170                 175

Asn Thr Asn Gln Glu Asp Leu Leu Val Leu Trp Gly Ile His His Pro
            180                 185                 190

Asn Asp Glu Glu Glu Gln Lys Arg Ile Tyr Lys Asn Pro Thr Thr Tyr
        195                 200                 205

Ile Ser Val Gly Thr Ser Thr Leu Asn Gln Arg Leu Val Pro Lys Ile
    210                 215                 220

Ala Thr Arg Pro Lys Val Asn Gly Gln Ser Gly Arg Val Glu Phe Phe
225                 230                 235                 240

Trp Thr Ile Leu Lys Ser Asn Asp Thr Ile Asn Phe Glu Ser Asn Gly
                245                 250                 255

Asn Phe Ile Ala Pro Lys Asn Ala Tyr Lys Ile Val Lys Lys Gly Ser
            260                 265                 270

Ser Thr Ile Met Lys Ser Glu Leu Glu Tyr Gly Asn Cys Ser Thr Lys
        275                 280                 285

Cys Gln Thr Pro Ile Gly Ala Ile Asn Ser Ser Met Pro Phe His Asn
    290                 295                 300

Ile His Pro Leu Thr Ile Gly Glu Cys Pro Lys Tyr Val Lys Ser Asn
305                 310                 315                 320

Arg Leu Val Leu Ala Thr Gly Leu Arg Asn Ser Pro Gln Gly Glu Gly
                325                 330                 335

Arg Arg Lys Lys Arg Gly Leu Phe Gly Ala Ile Ala Gly Phe Ile Glu
            340                 345                 350

Gly Gly Trp Gln Gly Met Val Asp Gly Trp Tyr Gly Tyr His His Ser
        355                 360                 365

Asn Glu Gln Gly Thr Gly Tyr Ala Ala Asp Lys Glu Ser Thr Gln Lys
    370                 375                 380
```

```
Ala Ile Asp Gly Val Thr Asn Lys Val Asn Ser Ile Ile Asp Lys Met
385                 390                 395                 400

Asn Thr Gln Phe Glu Ala Val Gly Arg Glu Phe Asn Asn Leu Glu Lys
            405                 410                 415

Arg Ile Glu Asn Leu Asn Lys Lys Met Glu Asp Gly Phe Leu Asp Val
            420                 425                 430

Trp Thr Tyr Asn Ala Glu Leu Leu Val Leu Met Glu Asn Glu Arg Thr
            435                 440                 445

Leu Asp Phe His Asp Ser Asn Val Arg Asn Leu Tyr Asp Lys Val Arg
450                 455                 460

Leu Gln Leu Arg Asp Asn Ala Lys Glu Leu Gly Asn Gly Cys Phe Glu
465                 470                 475                 480

Phe Tyr His Lys Cys Asp Asn Glu Cys Met Glu Ser Val Arg Asn Gly
                485                 490                 495

Thr Tyr Asp Tyr Pro Gln Tyr Ser Lys Glu Ala Arg Leu Lys Arg Glu
            500                 505                 510

Glu Ile Ser Gly Val Lys Leu Glu Ser Ile Gly Thr Tyr Gln Ile Leu
            515                 520                 525

Ser Ile Tyr Ser Thr Val Ala Ser Ser Leu Ala Leu Ala Ile Met Val
530                 535                 540

Ala Gly Leu Ser Leu Trp Met Cys Ser Xaa
545                 550

<210> SEQ ID NO 27
<211> LENGTH: 564
<212> TYPE: PRT
<213> ORGANISM: H5N1

<400> SEQUENCE: 27

Val Leu Leu Leu Ala Ile Val Ser Leu Val Lys Ser Asp Gln Ile Cys
1               5                   10                  15

Ile Gly Tyr His Ala Asn Asn Ser Thr Glu Gln Val Asp Thr Ile Met
            20                  25                  30

Glu Lys Asn Val Thr Val Thr His Ala Gln Asp Ile Leu Glu Lys Thr
        35                  40                  45

His Asn Gly Lys Leu Cys Asp Leu Asp Gly Val Lys Pro Leu Ile Leu
50                  55                  60

Arg Asp Cys Ser Val Ala Gly Trp Leu Leu Gly Asn Pro Met Cys Asp
65                  70                  75                  80

Glu Phe Pro Asn Val Ser Glu Trp Ser Tyr Ile Val Glu Lys Ile Asn
                85                  90                  95

Pro Ala Asn Asp Leu Cys Tyr Pro Gly Asn Phe Asn Asn Tyr Glu Glu
            100                 105                 110

Leu Lys His Leu Leu Ser Arg Ile Asn Arg Phe Glu Lys Ile Gln Ile
        115                 120                 125

Ile Pro Lys Ser Ser Trp Pro Asp His Glu Ala Ser Leu Gly Val Ser
130                 135                 140

Ser Ala Cys Pro Tyr Gln Gly Glu Pro Ser Phe Tyr Arg Asn Val Val
145                 150                 155                 160

Trp Leu Ile Lys Lys Asn Asn Thr Tyr Pro Thr Ile Lys Glu Asn Tyr
                165                 170                 175

His Asn Thr Asn Gln Glu Asp Leu Leu Val Leu Trp Gly Ile His His
            180                 185                 190

Pro Asn Asp Glu Glu Glu Gln Lys Arg Ile Tyr Lys Asn Pro Thr Thr
```

```
        195                 200                 205

Tyr Ile Ser Val Gly Thr Ser Thr Leu Asn Gln Arg Leu Val Pro Lys
    210                 215                 220

Ile Ala Thr Arg Pro Lys Val Asn Gly Gln Ser Gly Arg Val Glu Phe
225                 230                 235                 240

Phe Trp Thr Ile Leu Lys Ser Asn Asp Thr Ile Asn Phe Glu Ser Asn
                245                 250                 255

Gly Asn Phe Ile Ala Pro Lys Asn Ala Tyr Lys Ile Val Lys Lys Gly
            260                 265                 270

Ser Ser Thr Ile Met Lys Ser Glu Leu Glu Tyr Gly Asn Cys Ser Thr
        275                 280                 285

Lys Cys Gln Thr Pro Ile Gly Ala Ile Asn Ser Ser Met Pro Phe His
    290                 295                 300

Asn Ile His Pro Leu Thr Ile Gly Glu Cys Pro Lys Tyr Val Lys Ser
305                 310                 315                 320

Asn Arg Leu Val Leu Ala Thr Gly Leu Arg Asn Ser Pro Gln Gly Glu
                325                 330                 335

Gly Arg Arg Lys Lys Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Thr Gly Tyr Ala Ala Asp Lys Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Lys Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Arg Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Lys Glu Ala Arg Leu Lys Arg
            500                 505                 510

Glu Glu Ile Ser Gly Val Lys Leu Glu Ser Ile Gly Thr Tyr Gln Ile
        515                 520                 525

Leu Ser Ile Tyr Ser Thr Val Ala Ser Ser Leu Ala Leu Ala Ile Met
    530                 535                 540

Val Ala Gly Leu Ser Leu Trp Met Cys Ser Asn Gly Ser Leu Gln Cys
545                 550                 555                 560

Arg Ile Cys Ile
```

<210> SEQ ID NO 28
<211> LENGTH: 553
<212> TYPE: PRT
<213> ORGANISM: H5N1
<220> FEATURE:
<221> NAME/KEY: misc_feature
<222> LOCATION: (1)..(1)
<223> OTHER INFORMATION: Xaa can be any naturally occurring amino acid

<400> SEQUENCE: 28

```
Xaa Val Leu Leu Leu Ala Ile Ile Ser Leu Val Lys Ser Asp Gln Ile
1               5                   10                  15

Cys Ile Gly Tyr His Ala Asn Asn Ser Thr Glu Gln Val Asp Thr Ile
            20                  25                  30

Met Glu Lys Asn Val Thr Val Thr His Ala Gln Asp Ile Leu Glu Lys
        35                  40                  45

Thr His Asn Gly Lys Leu Cys Asp Leu Asp Gly Val Lys Pro Leu Ile
    50                  55                  60

Leu Arg Gly Cys Ser Val Ala Gly Trp Leu Leu Gly Asn Pro Met Cys
65                  70                  75                  80

Asp Glu Phe Pro Asn Val Ser Glu Trp Ser Tyr Ile Val Glu Lys Ile
            85                  90                  95

Asn Pro Ala Asn Asp Leu Cys Tyr Pro Gly Asn Phe Asn Asn Tyr Glu
        100                 105                 110

Glu Leu Lys His Leu Leu Ser Arg Ile Asn Arg Phe Glu Lys Ile Gln
    115                 120                 125

Ile Ile Pro Lys Ser Ser Trp Pro Asp His Glu Ala Ser Leu Gly Val
130                 135                 140

Ser Ser Ala Cys Pro Tyr Gln Gly Glu Pro Ser Phe Tyr Arg Asn Val
145                 150                 155                 160

Val Trp Leu Ile Lys Lys Asn Asn Thr Tyr Pro Thr Ile Lys Glu Ser
            165                 170                 175

Tyr His Asn Thr Asn Gln Glu Asp Leu Leu Val Leu Trp Gly Ile His
        180                 185                 190

His Pro Asn Asp Glu Glu Glu Gln Lys Arg Ile Tyr Lys Asn Pro Thr
    195                 200                 205

Thr Tyr Ile Ser Val Gly Thr Ser Thr Leu Asn Gln Arg Leu Val Pro
210                 215                 220

Lys Ile Ala Thr Arg Pro Lys Val Asn Gly Gln Ser Gly Arg Val Glu
225                 230                 235                 240

Phe Phe Trp Thr Ile Leu Lys Ser Asn Asp Thr Ile Asn Phe Glu Ser
            245                 250                 255

Asn Gly Asn Phe Ile Ala Pro Lys Asn Ala Tyr Lys Ile Val Lys Lys
        260                 265                 270

Gly Ser Ser Thr Ile Met Lys Ser Glu Leu Glu Tyr Gly Asn Cys Ser
    275                 280                 285

Thr Lys Cys Gln Thr Pro Ile Gly Ala Ile Asn Ser Ser Met Pro Phe
290                 295                 300

His Asn Ile His Pro Leu Thr Ile Gly Glu Cys Pro Lys Tyr Val Lys
305                 310                 315                 320

Ser Asn Arg Leu Val Leu Ala Thr Gly Leu Arg Asn Ser Pro Gln Gly
            325                 330                 335

Glu Gly Arg Arg Lys Lys Arg Gly Leu Phe Gly Ala Ile Ala Gly Phe
        340                 345                 350

Ile Glu Gly Gly Trp Gln Gly Met Val Asp Gly Trp Tyr Gly Tyr His
    355                 360                 365

His Ser Asn Glu Gln Gly Thr Gly Tyr Ala Ala Asp Lys Glu Ser Thr
370                 375                 380

Gln Lys Ala Ile Asp Gly Val Thr Asn Lys Val Asn Ser Ile Ile Asp
385                 390                 395                 400

Lys Met Asn Thr Gln Phe Glu Ala Val Gly Arg Glu Phe Asn Asn Leu
```

```
                         405                 410                 415
Glu Lys Arg Ile Glu Asn Leu Asn Lys Lys Met Glu Asp Gly Phe Leu
                420                 425                 430

Asp Val Trp Thr Tyr Asn Ala Glu Leu Leu Val Leu Met Glu Asn Glu
            435                 440                 445

Arg Thr Leu Asp Phe His Asp Ser Asn Val Arg Asn Leu Tyr Asp Lys
        450                 455                 460

Val Arg Leu Gln Leu Arg Asp Asn Ala Lys Glu Leu Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Gln Tyr Ser Lys Glu Ala Arg Leu Lys
                500                 505                 510

Arg Glu Glu Ile Ser Gly Val Lys Leu Glu Ser Ile Gly Thr Tyr Gln
            515                 520                 525

Ile Leu Ser Ile Tyr Ser Thr Val Ala Ser Ser Leu Ala Leu Ala Ile
        530                 535                 540

Met Val Ala Gly Leu Ser Leu Trp Met
545                 550

<210> SEQ ID NO 29
<211> LENGTH: 558
<212> TYPE: PRT
<213> ORGANISM: H5N1
<220> FEATURE:
<221> NAME/KEY: misc_feature
<222> LOCATION: (558)..(558)
<223> OTHER INFORMATION: Xaa can be any naturally occurring amino acid

<400> SEQUENCE: 29

Ile Val Leu Leu Leu Ala Ile Val Ser Leu Val Lys Ser Asp Gln Ile
1               5                   10                  15

Cys Ile Gly Tyr His Ala Asn Asn Ser Thr Glu Gln Val Asp Thr Ile
                20                  25                  30

Met Glu Lys Asn Val Thr Val Thr His Ala Gln Asp Ile Leu Glu Lys
            35                  40                  45

Thr His Asn Gly Lys Leu Cys Asp Leu Asp Gly Val Lys Pro Leu Ile
        50                  55                  60

Leu Arg Asp Cys Ser Val Ala Gly Trp Leu Leu Gly Asn Pro Met Cys
65                  70                  75                  80

Asp Glu Phe Pro Asn Val Ser Glu Trp Ser Tyr Ile Val Glu Lys Ile
                85                  90                  95

Asn Pro Ala Asn Asp Leu Cys Tyr Pro Gly Asn Phe Asn Asn Tyr Glu
            100                 105                 110

Glu Leu Lys His Leu Leu Ser Arg Ile Asn Arg Phe Glu Lys Ile Lys
        115                 120                 125

Ile Ile Pro Lys Ser Ser Trp Pro Asp His Glu Ala Ser Leu Gly Val
    130                 135                 140

Ser Ser Ala Cys Pro Tyr Gln Gly Gly Pro Ser Phe Tyr Arg Asn Val
145                 150                 155                 160

Val Trp Leu Ile Lys Lys Asn Asn Thr Tyr Pro Thr Ile Lys Lys Ser
                165                 170                 175

Tyr His Asn Thr Asn Gln Glu Asp Leu Leu Val Leu Trp Gly Ile His
            180                 185                 190

His Pro Asn Asp Glu Glu Glu Gln Thr Arg Ile Tyr Lys Asn Pro Thr
        195                 200                 205
```

Thr Tyr Ile Ser Val Gly Thr Ser Thr Leu Asn Gln Arg Leu Val Pro
    210                 215                 220
Lys Ile Ala Thr Arg Ser Lys Val Asn Gly Gln Ser Gly Arg Val Glu
225                 230                 235                 240
Phe Phe Trp Thr Ile Leu Lys Ser Asn Asp Thr Ile Asn Phe Glu Ser
                245                 250                 255
Asn Gly Asn Phe Ile Ala Pro Glu Asn Ala Tyr Lys Ile Val Lys Lys
            260                 265                 270
Gly Asp Ser Thr Ile Met Lys Ser Glu Leu Glu His Gly Asn Cys Asn
        275                 280                 285
Thr Lys Cys Gln Thr Pro Ile Gly Ala Ile Asn Ser Ser Met Pro Phe
    290                 295                 300
His Asn Ile His Pro Leu Thr Ile Gly Glu Cys Pro Lys Tyr Val Lys
305                 310                 315                 320
Ser Asn Arg Leu Val Leu Ala Thr Gly Leu Arg Asn Ser Pro Gln Gly
                325                 330                 335
Glu Gly Arg Arg Lys Lys Arg Gly Leu Phe Gly Ala Ile Ala Gly Phe
            340                 345                 350
Ile Glu Gly Gly Trp Gln Gly Met Val Asp Gly Trp Tyr Gly Tyr His
        355                 360                 365
His Ser Asn Glu Gln Gly Ser Gly Tyr Ala Ala Asp Lys Glu Ser Thr
    370                 375                 380
Gln Lys Ala Ile Asp Gly Val Thr Asn Lys Val Asn Ser Ile Ile Asp
385                 390                 395                 400
Lys Met Asn Thr Gln Phe Glu Ala Val Gly Arg Glu Phe Asn Asn Leu
                405                 410                 415
Glu Lys Arg Ile Glu Asn Leu Asn Lys Lys Met Glu Asp Gly Phe Leu
            420                 425                 430
Asp Val Trp Thr Tyr Asn Ala Glu Leu Leu Val Leu Met Glu Asn Glu
        435                 440                 445
Arg Thr Leu Asp Phe His Asp Ser Asn Val Lys Asn Leu Tyr Asp Lys
    450                 455                 460
Val Arg Leu Gln Leu Arg Asp Asn Ala Lys Glu Leu Gly Asn Gly Cys
465                 470                 475                 480
Phe Glu Phe Tyr His Arg Cys Asp Asn Glu Cys Met Glu Ser Val Arg
                485                 490                 495
Asn Gly Thr Tyr Asp Tyr Pro Gln Tyr Ser Glu Glu Ala Arg Leu Asn
            500                 505                 510
Arg Glu Glu Ile Ser Gly Val Lys Leu Glu Ser Ile Gly Thr Tyr Gln
        515                 520                 525
Ile Leu Ser Ile Tyr Ser Thr Val Ala Ser Ser Leu Ala Leu Ala Ile
    530                 535                 540
Met Met Ala Gly Leu Phe Leu Trp Met Cys Ser Asn Gly Xaa
545                 550                 555

<210> SEQ ID NO 30
<211> LENGTH: 557
<212> TYPE: PRT
<213> ORGANISM: H5N1
<220> FEATURE:
<221> NAME/KEY: misc_feature
<222> LOCATION: (130)..(130)
<223> OTHER INFORMATION: Xaa can be any naturally occurring amino acid

<400> SEQUENCE: 30

```
Leu Leu Ala Ile Val Ser Leu Val Lys Ser Asp Gln Ile Cys Ile Gly
1               5                   10                  15

Tyr His Ala Asn Asn Ser Thr Glu Gln Val Asp Thr Ile Met Glu Lys
            20                  25                  30

Asn Val Thr Val Thr His Ala Gln Asp Ile Leu Glu Lys Thr His Asn
        35                  40                  45

Gly Lys Leu Cys Asp Leu Asp Gly Val Lys Pro Leu Ile Leu Arg Asp
    50                  55                  60

Cys Ser Val Ala Gly Trp Leu Leu Gly Asn Pro Met Cys Asp Glu Phe
65                  70                  75                  80

Pro Asn Val Ser Glu Trp Ser Tyr Ile Val Glu Lys Ile Asn Pro Ala
                85                  90                  95

Asn Asp Leu Cys Tyr Pro Gly Asn Phe Asn Asn Tyr Glu Glu Leu Lys
                100                 105                 110

His Leu Leu Ser Arg Ile Asn Arg Phe Glu Lys Ile Lys Ile Ile Pro
            115                 120                 125

Lys Xaa Ser Trp Pro Asp His Glu Ala Ser Leu Gly Val Ser Ser Ala
        130                 135                 140

Cys Pro Tyr Gln Gly Gly Pro Ser Phe Tyr Arg Asn Val Val Trp Leu
145                 150                 155                 160

Ile Lys Lys Asn Asn Thr Tyr Pro Thr Ile Lys Glu Ser Tyr His Asn
                165                 170                 175

Thr Asn Gln Glu Asp Leu Leu Val Leu Trp Gly Ile His His Pro Asn
            180                 185                 190

Asp Glu Glu Glu Gln Thr Arg Ile Tyr Lys Asn Pro Thr Thr Tyr Ile
        195                 200                 205

Ser Ile Gly Thr Ser Thr Leu Asn Gln Arg Leu Val Pro Lys Ile Ala
    210                 215                 220

Thr Arg Ser Lys Val Asn Gly Gln Ser Gly Arg Val Glu Phe Phe Trp
225                 230                 235                 240

Thr Ile Leu Lys Ser Asn Asp Thr Ile Asn Phe Glu Ser Asn Gly Asn
                245                 250                 255

Phe Ile Ala Pro Glu Asn Ala Tyr Lys Ile Val Lys Lys Gly Asp Ser
                260                 265                 270

Thr Ile Met Lys Ser Glu Leu Glu Tyr Gly Asn Cys Asn Thr Lys Cys
            275                 280                 285

Gln Thr Pro Ile Gly Ala Ile Asn Ser Ser Met Pro Phe His Asn Ile
        290                 295                 300

His Pro Leu Thr Ile Gly Glu Cys Pro Lys Tyr Val Lys Ser Asn Arg
305                 310                 315                 320

Leu Val Leu Ala Thr Gly Leu Arg Asn Ser Pro Gln Gly Glu Gly Arg
                325                 330                 335

Arg Lys Lys Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Glu Gln Gly Ser Gly Tyr Ala Ala Asp Lys Glu Ser Thr Gln Lys Ala
    370                 375                 380

Ile Asp Gly Val Thr Asn Lys Val Asn Ser Ile Ile Asp Lys Met Asn
385                 390                 395                 400

Thr Gln Phe Glu Ala Val Gly Arg Glu Phe Asn Asn Leu Glu Lys Arg
                405                 410                 415

Ile Glu Asn Leu Asn Lys Lys Met Glu Asp Gly Phe Leu Asp Val Trp
```

```
                420             425             430
Thr Tyr Asn Ala Glu Leu Leu Val Leu Met Glu Asn Glu Arg Thr Leu
            435                 440                 445
Asp Phe His Asp Ser Asn Val Lys Asn Leu Tyr Asp Lys Val Arg Leu
        450                 455                 460
Gln Leu Arg Asp Asn Ala Lys Glu Leu Gly Asn Gly Cys Phe Glu Phe
465                 470                 475                 480
Tyr His Arg Cys Asp Asn Glu Cys Met Glu Ser Val Arg Asn Gly Thr
                485                 490                 495
Tyr Asp Tyr Pro Gln Tyr Ser Glu Glu Ala Arg Leu Lys Arg Glu Glu
            500                 505                 510
Ile Ser Gly Val Lys Leu Glu Ser Ile Gly Thr Tyr Gln Ile Leu Ser
        515                 520                 525
Ile Tyr Ser Thr Val Ala Gly Ser Leu Ala Leu Ala Ile Met Met Ala
        530                 535                 540
Gly Leu Phe Leu Trp Met Cys Ser Asn Gly Ser Leu Gln
545                 550                 555

<210> SEQ ID NO 31
<211> LENGTH: 547
<212> TYPE: PRT
<213> ORGANISM: H5N1
<220

-continued

```
Lys Ile Ala Thr Arg Ser Lys Val Asn Gly Gln Ser Gly Arg Val Glu
225                 230                 235                 240

Phe Phe Trp Thr Ile Leu Lys Ser Asn Asp Thr Ile Asn Phe Glu Ser
            245                 250                 255

Asn Gly Asn Phe Ile Ala Pro Glu Asn Ala Tyr Lys Ile Val Lys Lys
        260                 265                 270

Gly Asp Ser Thr Ile Met Lys Ser Glu Leu Glu Tyr Gly Asn Cys Asn
    275                 280                 285

Thr Lys Cys Gln Thr Pro Ile Gly Ala Ile Asn Ser Ser Met Pro Phe
290                 295                 300

His Asn Ile His Pro Leu Thr Ile Gly Glu Cys Pro Lys Tyr Val Lys
305                 310                 315                 320

Ser Asn Arg Leu Val Leu Ala Thr Gly Leu Arg Asn Ser Pro Gln Gly
                325                 330                 335

Glu Gly Arg Arg Lys Lys Arg Gly Leu Phe Gly Ala Ile Ala Gly Phe
            340                 345                 350

Ile Glu Gly Gly Trp Gln Gly Met Val Asp Gly Trp Tyr Gly Tyr His
        355                 360                 365

His Ser Asn Glu Gln Gly Ser Gly Tyr Ala Ala Asp Lys Glu Ser Thr
    370                 375                 380

Gln Lys Ala Ile Asp Gly Val Thr Asn Lys Val Asn Ser Ile Ile Asp
385                 390                 395                 400

Lys Met Asn Thr Gln Phe Glu Ala Val Gly Arg Glu Phe Asn Asn Leu
                405                 410                 415

Glu Lys Arg Ile Glu Asn Leu Asn Lys Lys Met Glu Asp Gly Phe Leu
            420                 425                 430

Asp Val Trp Thr Tyr Asn Ala Glu Leu Leu Val Leu Met Glu Asn Glu
        435                 440                 445

Arg Thr Leu Asp Phe His Asp Ser Asn Val Lys Asn Leu Tyr Asp Lys
    450                 455                 460

Val Arg Leu Gln Leu Arg Asp Asn Ala Lys Glu Leu Gly Asn Gly Cys
465                 470                 475                 480

Phe Glu Phe Tyr His Arg Cys Asp Asn Glu Cys Met Glu Ser Val Arg
                485                 490                 495

Asn Gly Thr Tyr Asp Tyr Pro Gln Tyr Ser Glu Glu Ala Arg Leu Lys
            500                 505                 510

Arg Glu Glu Ile Ser Gly Val Lys Leu Glu Ser Ile Gly Thr Tyr Gln
        515                 520                 525

Ile Leu Ser Ile Tyr Ser Thr Val Ala Ser Ser Leu Ala Leu Ala Ile
    530                 535                 540

Met Val Xaa
545

<210> SEQ ID NO 32
<211> LENGTH: 547
<212> TYPE: PRT
<213> ORGANISM: H5N1
<220> FEATURE:
<221> NAME/KEY: misc_feature
<222> LOCATION: (154)..(154)
<223> OTHER INFORMATION: Xaa can be any naturally occurring amino acid
<220> FEATURE:
<221> NAME/KEY: misc_feature
<222> LOCATION: (329)..(329)
<223> OTHER INFORMATION: Xaa can be any naturally occurring amino acid
<220> FEATURE:
<221> NAME/KEY: misc_feature
```

<222> LOCATION: (547)..(547)
<223> OTHER INFORMATION: Xaa can be any naturally occurring amino acid

<400> SEQUENCE: 32

```
Ile Val Leu Leu Leu Ala Ile Val Ser Leu Val Lys Ser Asp Gln Ile
1               5                   10                  15

Cys Ile Gly Tyr His Ala Asn Asn Ser Thr Glu Gln Val Asp Thr Ile
            20                  25                  30

Met Glu Lys Asn Val Thr Val Thr His Ala Gln Asp Ile Leu Glu Lys
        35                  40                  45

Thr His Asn Gly Lys Leu Cys Asp Leu Asp Gly Val Lys Pro Leu Ile
    50                  55                  60

Leu Arg Asp Cys Ser Val Ala Gly Trp Leu Leu Gly Asn Pro Met Cys
65                  70                  75                  80

Asp Glu Phe Pro Asn Val Ser Glu Trp Ser Tyr Ile Val Glu Lys Ile
                85                  90                  95

Asn Pro Ala Asn Asp Leu Cys Tyr Pro Gly Asn Phe Asn Asn Tyr Glu
            100                 105                 110

Glu Leu Lys His Leu Leu Ser Arg Ile Asn Arg Phe Glu Lys Ile Lys
        115                 120                 125

Ile Ile Pro Lys Ser Ser Trp Pro Asp His Glu Ala Ser Leu Gly Val
    130                 135                 140

Ser Ser Ala Cys Pro Tyr Gln Gly Gly Xaa Ser Phe Tyr Arg Asn Val
145                 150                 155                 160

Val Trp Leu Ile Lys Lys Asn Asn Thr Tyr Pro Thr Ile Lys Glu Ser
                165                 170                 175

Tyr His Asn Thr Asn Gln Glu Asp Leu Leu Val Leu Trp Gly Ile His
            180                 185                 190

His Pro Asn Asp Glu Glu Glu Gln Thr Arg Ile Tyr Lys Asn Pro Thr
        195                 200                 205

Thr Tyr Ile Ser Ile Gly Thr Ser Thr Leu Asn Gln Arg Leu Val Pro
    210                 215                 220

Lys Ile Ala Thr Arg Ser Lys Val Asn Gly Gln Ser Gly Arg Val Glu
225                 230                 235                 240

Phe Phe Trp Thr Ile Leu Lys Ser Asn Asp Thr Ile Asn Phe Glu Ser
                245                 250                 255

Asn Gly Asn Phe Ile Ala Pro Glu Asn Ala Tyr Lys Ile Val Lys Lys
            260                 265                 270

Gly Asp Ser Thr Ile Met Lys Ser Glu Leu Glu Tyr Gly Asn Cys Asn
        275                 280                 285

Thr Lys Cys Gln Thr Pro Ile Gly Ala Ile Asn Ser Ser Met Pro Phe
    290                 295                 300

His Asn Ile His Pro Leu Thr Ile Gly Glu Cys Pro Lys Tyr Val Lys
305                 310                 315                 320

Ser Asn Arg Leu Val Leu Ala Thr Xaa Leu Arg Asn Ser Pro Gln Gly
                325                 330                 335

Glu Gly Arg Arg Lys Arg Gly Leu Phe Gly Ala Ile Ala Gly Phe
            340                 345                 350

Ile Glu Gly Gly Trp Gln Gly Met Val Asp Gly Trp Tyr Gly Tyr His
        355                 360                 365

His Ser Asn Glu Gln Gly Ser Gly Tyr Ala Ala Asp Lys Glu Ser Thr
    370                 375                 380

Gln Lys Ala Ile Asp Gly Val Thr Asn Lys Val Asn Ser Ile Ile Asp
385                 390                 395                 400
```

Lys Met Asn Thr Gln Phe Glu Ala Val Gly Arg Glu Phe Asn Asn Leu
405 410 415

Glu Lys Arg Ile Glu Asn Leu Asn Lys Lys Met Glu Asp Gly Phe Leu
420 425 430

Asp Val Trp Thr Tyr Asn Ala Glu Leu Leu Val Leu Met Glu Asn Glu
435 440 445

Arg Thr Leu Asp Phe His Asp Ser Asn Val Lys Asn Leu Tyr Asp Lys
450 455 460

Val Arg Leu Gln Leu Arg Asp Asn Ala Lys Glu Leu Gly Asn Gly Cys
465 470 475 480

Phe Glu Phe Tyr His Arg Cys Asp Asn Glu Cys Met Glu Ser Val Arg
485 490 495

Asn Gly Thr Tyr Asp Tyr Pro Gln Tyr Ser Glu Glu Ala Arg Leu Lys
500 505 510

Arg Glu Glu Ile Ser Gly Val Lys Leu Glu Ser Ile Gly Thr Tyr Gln
515 520 525

Ile Leu Ser Ile Tyr Ser Thr Val Ala Gly Ser Leu Ala Leu Ala Ile
530 535 540

Met Val Xaa
545

<210> SEQ ID NO 33
<211> LENGTH: 559
<212> TYPE: PRT
<213> ORGANISM: H5N1
<220> FEATURE:
<221> NAME/KEY: misc_feature
<222> LOCATION: (1)..(1)
<223> OTHER INFORMATION: Xaa can be any naturally occurring amino acid

<400> SEQUENCE: 33

Xaa Leu Leu Leu Ala Ile Val Ser Leu Val Lys Ser Asp Gln Ile Cys
1 5 10 15

Ile Gly Tyr His Ala Asn Asn Ser Thr Glu Gln Val Asp Thr Ile Met
20 25 30

Glu Lys Asn Val Thr Val Thr His Ala Gln Asp Ile Leu Glu Lys Thr
35 40 45

His Asn Gly Lys Leu Cys Asp Leu Asp Gly Val Lys Pro Leu Ile Leu
50 55 60

Arg Asp Cys Ser Val Ala Gly Trp Leu Leu Gly Asn Pro Met Cys Asp
65 70 75 80

Glu Phe Pro Asn Val Ser Glu Trp Ser Tyr Ile Val Glu Lys Ile Asn
85 90 95

Pro Ala Asn Asp Leu Cys Tyr Pro Gly Asn Phe Asn Asn Tyr Glu Glu
100 105 110

Leu Lys His Leu Leu Ser Arg Ile Asn Arg Phe Glu Lys Ile Gln Ile
115 120 125

Ile Pro Lys Ser Ser Trp Pro Asp His Glu Ala Ser Leu Gly Val Ser
130 135 140

Ser Ala Cys Pro Tyr Gln Gly Glu Pro Ser Phe Tyr Arg Asn Val Val
145 150 155 160

Trp Leu Ile Lys Lys Asn Asn Thr Tyr Pro Thr Ile Lys Glu Asn Tyr
165 170 175

His Asn Thr Asn Gln Glu Asp Leu Leu Val Leu Trp Gly Ile His His
180 185 190

```
Pro Asn Asp Glu Glu Gln Lys Arg Ile Tyr Lys Asn Pro Thr Thr
            195                 200                 205

Tyr Ile Ser Val Gly Thr Ser Thr Leu Thr Gln Arg Leu Val Pro Lys
210                 215                 220

Ile Ala Thr Arg Pro Lys Val Asn Gly Gln Ser Gly Arg Val Glu Phe
225                 230                 235                 240

Phe Trp Thr Ile Leu Lys Ser Asn Asp Thr Ile Asn Phe Glu Ser Asn
            245                 250                 255

Gly Asn Phe Ile Ala Pro Lys Asn Ala Tyr Lys Ile Val Lys Lys Gly
            260                 265                 270

Ser Ser Thr Ile Met Lys Ser Glu Leu Glu Tyr Gly Asn Cys Ser Thr
            275                 280                 285

Lys Cys Gln Thr Pro Ile Gly Ala Ile Asn Ser Ser Met Pro Phe His
290                 295                 300

Asn Ile His Pro Leu Thr Ile Gly Glu Cys Pro Lys Tyr Val Lys Ser
305                 310                 315                 320

Asn Arg Leu Val Leu Ala Thr Gly Leu Arg Asn Ser Pro Gln Gly Glu
                325                 330                 335

Gly Arg Arg Lys Lys Arg Gly Leu Phe Gly Ala Ile Ala Gly Phe Ile
                340                 345                 350

Glu Gly Gly Trp Gln Gly Met Val Asp Gly Trp Tyr Gly Tyr His His
            355                 360                 365

Ser Asn Glu Gln Gly Thr Gly Tyr Ala Ala Asp Lys Glu Ser Thr Gln
370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Lys Arg Ile Glu Asn Leu Asn Lys Lys Met Glu Asp Gly Phe Leu Asp
                420                 425                 430

Val Trp Thr Tyr Asn Ala Glu Leu Leu Val Leu Met Glu Asn Glu Arg
            435                 440                 445

Thr Leu Asp Phe His Asp Ser Asn Val Arg Asn Leu Tyr Asp Lys Val
450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Lys Glu Ala Arg Leu Lys Arg
            500                 505                 510

Glu Glu Ile Ser Gly Val Lys Leu Glu Ser Ile Gly Thr Tyr Gln Ile
            515                 520                 525

Leu Ser Ile Tyr Ser Thr Val Ala Ser Ser Leu Ala Leu Ala Ile Met
530                 535                 540

Val Ala Gly Leu Ser Leu Trp Met Cys Ser Asn Gly Ser Leu Gln
545                 550                 555

<210> SEQ ID NO 34
<211> LENGTH: 554
<212> TYPE: PRT
<213> ORGANISM: H5N1
<220> FEATURE:
<221> NAME/KEY: misc_feature
<222> LOCATION: (1)..(1)
<223> OTHER INFORMATION: Xaa can be any naturally occurring amino acid
<220> FEATURE:
```

<221> NAME/KEY: misc_feature
<222> LOCATION: (554)..(554)
<223> OTHER INFORMATION: Xaa can be any naturally occurring amino acid

<400> SEQUENCE: 34

```
Xaa Val Lys Ser Asp Gln Ile Cys Ile Gly Tyr His Ala Asn Asn Ser
1               5                   10                  15

Thr Glu Gln Val Asp Thr Ile Met Glu Lys Asn Val Thr Val Thr His
            20                  25                  30

Ala Gln Asp Ile Leu Glu Lys Thr His Asn Gly Lys Leu Cys Asp Leu
        35                  40                  45

Asp Gly Val Lys Pro Leu Ile Leu Arg Asp Cys Ser Val Ala Gly Trp
    50                  55                  60

Leu Leu Gly Asn Pro Met Cys Asp Glu Phe Pro Asn Val Ser Glu Trp
65                  70                  75                  80

Ser Tyr Ile Val Glu Lys Ile Asn Pro Ala Asn Asp Leu Cys Tyr Pro
                85                  90                  95

Gly Asn Phe Asn Asn Tyr Glu Glu Leu Lys His Leu Leu Ser Arg Ile
            100                 105                 110

Asn Arg Phe Glu Lys Ile Gln Ile Ile Pro Lys Ser Ser Trp Pro Asp
        115                 120                 125

His Glu Ala Ser Leu Gly Val Ser Ser Ala Cys Pro Tyr Gln Gly Glu
    130                 135                 140

Pro Ser Phe Tyr Arg Asn Val Val Trp Leu Ile Lys Lys Asn Asn Thr
145                 150                 155                 160

Tyr Pro Thr Ile Lys Glu Ser Tyr His Asn Thr Asn Gln Glu Asp Leu
                165                 170                 175

Leu Val Leu Trp Gly Ile His His Pro Asn Asp Glu Glu Gln Lys
            180                 185                 190

Arg Ile Tyr Lys Asn Pro Thr Thr Tyr Ile Ser Val Gly Thr Ser Thr
        195                 200                 205

Leu Asn Gln Arg Leu Val Pro Lys Ile Ala Thr Arg Pro Lys Val Asn
    210                 215                 220

Gly Gln Ser Gly Arg Val Glu Phe Phe Trp Thr Ile Leu Lys Ser Asn
225                 230                 235                 240

Asp Thr Ile Asn Phe Glu Ser Asn Gly Asn Phe Ile Ala Pro Lys Asn
                245                 250                 255

Ala Tyr Lys Ile Val Lys Lys Gly Ser Ser Thr Ile Met Lys Ser Glu
            260                 265                 270

Leu Glu Tyr Gly Asn Cys Ser Thr Lys Cys Gln Thr Pro Ile Gly Ala
        275                 280                 285

Ile Asn Ser Ser Met Pro Phe His Asn Ile His Pro Leu Thr Ile Gly
    290                 295                 300

Glu Cys Pro Lys Tyr Val Lys Ser Asn Arg Leu Val Leu Ala Thr Gly
305                 310                 315                 320

Leu Arg Asn Ser Pro Gln Gly Glu Gly Arg Lys Lys Arg Gly Leu
                325                 330                 335

Phe Gly Ala Ile Ala Gly Phe Ile Glu Gly Gly Trp Gln Gly Met Val
            340                 345                 350

Asp Gly Trp Tyr Gly Tyr His His Ser Asn Glu Gln Gly Thr Gly Tyr
        355                 360                 365

Ala Ala Asp Lys Glu Ser Thr Gln Lys Ala Ile Asp Gly Val Thr Asn
    370                 375                 380

Lys Val Asn Ser Ile Ile Asp Lys Met Asn Thr Gln Phe Glu Ala Val
```

```
                385                 390                 395                 400

Gly Arg Glu Phe Asn Asn Leu Glu Lys Arg Ile Glu Asn Leu Asn Lys
                    405                 410                 415

Lys Met Glu Asp Gly Phe Leu Asp Val Trp Thr Tyr Asn Ala Glu Leu
                420                 425                 430

Leu Val Leu Met Glu Asn Glu Arg Thr Leu Asp Phe His Asp Ser Asn
                435                 440                 445

Val Arg Asn Leu Tyr Asp Lys Val Arg Leu Gln Leu Arg Asp Asn Ala
            450                 455                 460

Lys Glu Leu Gly Asn Gly Cys Phe Glu Phe Tyr His Lys Cys Asp Asn
465                 470                 475                 480

Glu Cys Met Glu Ser Val Arg Asn Gly Thr Tyr Asp Tyr Pro Gln Tyr
                485                 490                 495

Ser Lys Glu Ala Arg Leu Lys Arg Glu Glu Ile Ser Gly Val Lys Leu
                500                 505                 510

Glu Ser Ile Gly Thr Tyr Gln Ile Leu Ser Ile Tyr Ser Thr Val Ala
                515                 520                 525

Ser Ser Leu Ala Leu Ala Ile Met Val Ala Gly Leu Ser Leu Trp Met
            530                 535                 540

Cys Ser Asn Gly Ser Leu Gln Cys Arg Xaa
545                 550

<210> SEQ ID NO 35
<211> LENGTH: 537
<212> TYPE: PRT
<213> ORGANISM: H5N1
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (537

```
                165                 170                 175
Leu Trp Gly Ile His His Pro Asn Asp Glu Glu Gln Lys Arg Ile
            180                 185                 190

Tyr Lys Asn Pro Thr Thr Tyr Ile Ser Val Gly Thr Ser Thr Leu Asn
            195                 200                 205

Gln Arg Leu Val Pro Lys Ile Ala Thr Arg Pro Lys Val Asn Gly Gln
            210                 215                 220

Ser Gly Arg Val Glu Phe Phe Trp Thr Ile Leu Lys Ser Asn Asp Thr
225                 230                 235                 240

Ile Asn Phe Glu Ser Asn Gly Asn Phe Ile Ala Pro Lys Asn Ala Tyr
                245                 250                 255

Lys Ile Val Lys Lys Gly Ser Ser Thr Ile Met Lys Ser Glu Leu Glu
            260                 265                 270

Tyr Gly Asn Cys Ser Thr Lys Cys Gln Thr Pro Ile Gly Ala Ile Asn
            275                 280                 285

Ser Ser Met Pro Phe His Asn Ile His Pro Leu Thr Ile Gly Glu Cys
            290                 295                 300

Pro Lys Tyr Val Lys Ser Asn Arg Leu Val Leu Ala Thr Gly Leu Arg
305                 310                 315                 320

Asn Ser Pro Gln Gly Glu Gly Arg Arg Lys Arg Gly Leu Phe Gly
                325                 330                 335

Ala Ile Ala Gly Phe Ile Glu Gly Gly Trp Gln Gly Met Val Asp Gly
            340                 345                 350

Trp Tyr Gly Tyr His His Ser Asn Glu Gln Gly Thr Gly Tyr Ala Ala
            355                 360                 365

Asp Lys Glu Ser Thr Gln Lys Ala Ile Asp Gly Val Thr Asn Lys Val
            370                 375                 380

Asn Ser Ile Ile Asp Lys Met Asn Thr Gln Phe Glu Ala Val Gly Arg
385                 390                 395                 400

Glu Phe Asn Asn Leu Glu Lys Arg Ile Glu Asn Leu Asn Lys Lys Met
                405                 410                 415

Glu Asp Gly Phe Leu Asp Val Trp Thr Tyr Asn Ala Glu Leu Leu Val
            420                 425                 430

Leu Met Glu Asn Glu Arg Thr Leu Asp Phe His Asp Ser Asn Val Arg
            435                 440                 445

Asn Leu Tyr Asp Lys Val Arg Leu Gln Leu Arg Asp Asn Ala Lys Glu
            450                 455                 460

Leu Gly Asn Gly Cys Phe Glu Phe Tyr His Lys Cys Asp Asn Glu Cys
465                 470                 475                 480

Met Glu Ser Val Arg Asn Gly Thr Tyr Asp Tyr Pro Gln Tyr Ser Lys
                485                 490                 495

Glu Ala Arg Leu Lys Arg Glu Glu Ile Ser Gly Val Lys Leu Glu Ser
            500                 505                 510

Ile Gly Thr Tyr Gln Ile Leu Ser Ile Tyr Ser Thr Val Ala Ser Ser
            515                 520                 525

Leu Ala Leu Ala Ile Met Val Ala Xaa
            530                 535

<210> SEQ ID NO 36
<211> LENGTH: 554
<212> TYPE: PRT
<213> ORGANISM: H5N1

<400> SEQUENCE: 36
```

```
Lys Gly Asp Gln Ile Cys Ile Gly Tyr His Ala Asn Asn Ser Thr Glu
  1               5                  10                  15

Gln Val Asp Thr Ile Met Glu Lys Asn Val Thr Val Thr His Ala Gln
             20                  25                  30

Asp Ile Leu Glu Lys Thr His Asn Gly Lys Leu Cys Asp Leu Asp Gly
         35                  40                  45

Val Lys Pro Leu Ile Leu Arg Asp Cys Ser Val Ala Gly Trp Leu Leu
     50                  55                  60

Gly Asn Pro Met Cys Asp Glu Phe Pro Asn Val Ser Glu Trp Ser Tyr
 65                  70                  75                  80

Ile Val Glu Lys Ile Asn Pro Ala Asn Asp Leu Cys Tyr Pro Gly Asn
                 85                  90                  95

Phe Asn Asn Tyr Glu Glu Leu Lys His Leu Leu Ser Arg Ile Asn Arg
                100                 105                 110

Phe Glu Lys Ile Lys Ile Ile Pro Lys Ser Ser Trp Pro Asp His Glu
            115                 120                 125

Ala Ser Leu Gly Val Ser Ser Ala Cys Pro Tyr Gln Gly Gly Pro Ser
        130                 135                 140

Phe Tyr Arg Asn Val Val Trp Leu Ile Lys Lys Asn Asn Thr Tyr Pro
145                 150                 155                 160

Thr Ile Lys Glu Ser Tyr His Asn Thr Asn Gln Glu Asp Leu Leu Val
                165                 170                 175

Leu Trp Gly Ile His His Pro Asn Asp Glu Glu Gln Thr Arg Ile
            180                 185                 190

Tyr Lys Asn Pro Asn Thr Tyr Ile Ser Val Gly Thr Ser Thr Leu Asn
        195                 200                 205

Gln Arg Leu Val Pro Lys Ile Ala Thr Arg Ser Lys Val Asn Gly Gln
    210                 215                 220

Ser Gly Arg Val Glu Phe Phe Trp Thr Ile Leu Lys Ser Asn Asp Thr
225                 230                 235                 240

Ile Asn Phe Glu Ser Asn Gly Asn Phe Ile Ala Pro Glu Asn Ala Tyr
                245                 250                 255

Lys Ile Val Lys Lys Gly Asp Ser Thr Ile Met Lys Ser Glu Leu Glu
            260                 265                 270

Tyr Gly Asn Cys Ser Thr Lys Cys Gln Thr Pro Ile Gly Ala Ile Asn
        275                 280                 285

Ser Ser Met Pro Phe His Asn Ile His Pro Leu Thr Ile Gly Glu Cys
    290                 295                 300

Pro Lys Tyr Val Lys Ser Asn Arg Leu Val Leu Ala Thr Gly Leu Arg
305                 310                 315                 320

Asn Ser Pro Gln Glu Glu Gly Arg Arg Lys Lys Arg Gly Leu Phe Gly
                325                 330                 335

Ala Ile Ala Gly Phe Ile Glu Gly Gly Trp Gln Gly Met Val Asp Gly
            340                 345                 350

Trp Tyr Gly Tyr His His Ser Asn Glu Gln Gly Ser Gly Tyr Ala Ala
        355                 360                 365

Asp Lys Glu Ser Thr Gln Lys Ala Ile Asp Gly Val Thr Asn Lys Val
    370                 375                 380

Asn Ser Ile Ile Asp Lys Met Asn Thr Gln Phe Glu Ala Val Gly Arg
385                 390                 395                 400

Glu Phe Asn Asn Leu Glu Lys Arg Ile Glu Asn Leu Asn Lys Lys Met
                405                 410                 415

Glu Asp Gly Phe Leu Asp Val Trp Thr Tyr Asn Ala Glu Leu Leu Val
```

-continued

```
            420                 425                 430

Leu Met Glu Asn Glu Arg Thr Leu Asp Phe His Asp Ser Asn Val Lys
        435                 440                 445

Asn Leu Tyr Asp Lys Val Arg Leu Gln Leu Arg Asp Asn Ala Lys Glu
    450                 455                 460

Leu Gly Asn Gly Cys Phe Glu Phe Tyr His Arg Cys Asp Asn Glu Cys
465                 470                 475                 480

Met Glu Ser Val Arg Asn Gly Thr Tyr Asp Tyr Pro Gln Tyr Ser Glu
                485                 490                 495

Glu Ala Arg Leu Lys Arg Glu Glu Ile Ser Gly Val Lys Leu Glu Ser
            500                 505                 510

Ile Gly Thr Tyr Gln Ile Leu Ser Ile Tyr Ser Thr Val Ala Ser Ser
        515                 520                 525

Leu Ala Leu Ala Ile Met Val Ala Gly Leu Phe Leu Trp Met Cys Ser
    530                 535                 540

Asn Gly Ser Leu Gln Cys Arg Ile Cys Ile
545                 550

<210> SEQ ID NO 37
<211> LENGTH: 511
<212> TYPE: PRT
<213> ORGANISM: H5N1
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (182)..(182)
<223> OTHER INFORMATION: Xaa can be any naturally occurring amino acid
<220> FEATURE:
<221> NAME/KEY: misc_feature
<222> LOCATION: (200)..(200)
<223> OTHER INFORMATION: Xaa can be any naturally occurring amino acid
<220> FEATURE:
<221> NAME/KEY: misc_feature
<222> LOCATION: (511)..(511)
<223> OTHER INFORMATION: Xaa can be any naturally occurring amino acid

<400> SEQUENCE: 37

Xaa His Ala Asn Asn Ser Thr Glu Gln Val Asp Thr Ile Met Glu Lys
1               5                   10                  15

Asn Ile Thr Val Thr His Ala Gln Asp Ile Leu Glu Lys Thr His Asn
            20                  25                  30

Gly Lys Leu Cys Asp Leu Asp Gly Val Lys Pro Leu Ile Leu Arg Asp
        35                  40                  45

Cys Ser Val Ala Gly Trp Leu Leu Gly Asn Pro Met Cys Asp Glu Phe
    50                  55                  60

Leu Asn Val Ser Glu Trp Ser Tyr Ile Val Glu Lys Ile Asn Pro Ala
65                  70                  75                  80

Asn Asp Leu Cys Tyr Pro Gly Asn Phe Asn Asn Tyr Glu Glu Leu Lys
                85                  90                  95

His Leu Leu Ser Arg Ile Asn Arg Phe Glu Lys Ile Gln Ile Ile Ser
            100                 105                 110

Lys Asn Ser Trp Pro Asp His Glu Ala Ser Leu Gly Val Ser Ala Ala
        115                 120                 125

Cys Pro Tyr Gln Gly Gly Leu Ser Phe Tyr Arg Asn Val Val Trp Leu
    130                 135                 140

Ile Glu Lys Asn Asn Thr Tyr Pro Leu Ile Lys Lys Asn Tyr His Asn
145                 150                 155                 160
```

Thr Asn Gln Glu Asp Leu Leu Val Leu Trp Gly Ile His His Pro Asn
                165                 170                 175

Asp Glu Ala Glu Gln Xaa Arg Leu Tyr Lys Asn Ser Thr Thr Tyr Ile
            180                 185                 190

Ser Val Gly Thr Ser Thr Leu Xaa Gln Arg Leu Val Pro Lys Ile Ala
        195                 200                 205

Thr Arg Pro Lys Val Asn Gly Gln Ser Gly Arg Val Glu Phe Phe Trp
    210                 215                 220

Thr Ile Leu Lys Ser Asn Asp Val Ile Asn Phe Glu Ser Asn Gly Asn
225                 230                 235                 240

Phe Ile Ala Pro Glu Asn Ala Tyr Lys Ile Val Lys Lys Gly Asp Ser
                245                 250                 255

Thr Ile Met Lys Ser Asp Leu Glu Tyr Gly Asn Cys Ser Thr Lys Cys
            260                 265                 270

Gln Thr Pro Ile Gly Ala Ile Asn Ser Ser Met Pro Phe His Asn Ile
        275                 280                 285

His Pro Leu Thr Ile Gly Glu Cys Pro Lys Tyr Val Lys Ser Asn Arg
    290                 295                 300

Leu Val Leu Ala Thr Gly Leu Arg Asn Ser Pro Gln Gly Glu Arg Arg
305                 310                 315                 320

Arg Lys Lys Arg Gly Leu Phe Gly Ala Ile Ala Gly Phe Ile Glu Gly
                325                 330                 335

Gly Trp Gln Gly Met Val Asp Gly Trp Tyr Gly Tyr His His Ser Asn
            340                 345                 350

Glu Gln Gly Ser Gly Tyr Ala Ala Asp Lys Glu Ser Thr Gln Lys Ala
        355                 360                 365

Ile Asp Gly Val Thr Asn Lys Val Asn Ser Ile Ile Asp Lys Met Asn
    370                 375                 380

Thr Gln Phe Glu Ala Val Gly Arg Glu Phe Asn Asn Leu Glu Arg Arg
385                 390                 395                 400

Ile Glu Asn Leu Asn Lys Lys Met Glu Asp Gly Phe Leu Asp Val Trp
                405                 410                 415

Thr Tyr Asn Ala Glu Leu Leu Val Leu Met Glu Asn Glu Arg Thr Leu
            420                 425                 430

Asp Phe His Asp Ser Asn Val Lys Asn Leu Tyr Asp Lys Val Arg Leu
        435                 440                 445

Gln Leu Arg Asp Asn Ala Lys Glu Leu Gly Asn Gly Cys Phe Glu Phe
    450                 455                 460

Tyr His Arg Cys Asp Asn Glu Cys Met Glu Ser Val Arg Asn Gly Thr
465                 470                 475                 480

Tyr Asp Tyr Pro Gln Tyr Ser Glu Glu Ala Arg Leu Lys Arg Glu Glu
                485                 490                 495

Ile Ser Gly Ala Lys Leu Glu Ser Ile Gly Thr Tyr Gln Ile Xaa
            500                 505                 510

<210> SEQ ID NO 38
<211> LENGTH: 537
<212> TYPE: PRT
<213> ORGANISM: H5N1
<220> FEATURE:
<221> NAME/KEY: misc_feature
<222> LOCATION: (1)..(1)
<223> OTHER INFORMATION: Xaa can be any naturally occurring amino acid

<400> SEQUENCE: 38

```
Xaa Leu Val Lys Ser Asp Gln Ile Cys Ile Gly Tyr His Ala Asn Asn
1               5                   10                  15

Ser Thr Glu Gln Val Asp Thr Ile Met Glu Lys Asn Val Thr Val Thr
            20                  25                  30

His Ala Gln Asp Ile Leu Glu Lys Thr His Asn Gly Lys Leu Cys Asp
            35                  40                  45

Leu Asp Gly Val Lys Pro Leu Ile Leu Arg Asp Cys Ser Val Ala Gly
    50                  55                  60

Trp Leu Leu Gly Asn Pro Met Cys Asp Glu Phe Pro Asn Val Ser Glu
65                  70                  75                  80

Trp Ser Tyr Ile Val Glu Lys Ile Asn Pro Ala Asn Asp Leu Cys Tyr
                85                  90                  95

Pro Gly Asn Phe Asn Asn Tyr Glu Glu Leu Lys His Leu Leu Ser Arg
                100                 105                 110

Ile Asn Arg Phe Glu Lys Ile Lys Ile Ile Pro Lys Ser Ser Trp Pro
            115                 120                 125

Asp His Glu Ala Ser Leu Gly Val Ser Ser Ala Cys Pro Tyr Gln Arg
    130                 135                 140

Gly Pro Ser Phe Tyr Arg Asn Val Val Trp Leu Ile Lys Lys Asn Asn
145                 150                 155                 160

Thr Tyr Pro Thr Ile Lys Lys Ser Tyr His Asn Thr Asn Gln Glu Asp
                165                 170                 175

Leu Leu Val Leu Trp Gly Ile His His Pro Asn Asp Glu Glu Glu Gln
                180                 185                 190

Thr Arg Ile Tyr Lys Asn Pro Thr Thr Tyr Ile Ser Val Gly Thr Ser
            195                 200                 205

Thr Leu Asn Gln Arg Leu Val Pro Lys Ile Ala Thr Arg Ser Lys Val
    210                 215                 220

Asn Gly Gln Ser Gly Arg Val Glu Phe Phe Trp Thr Ile Leu Lys Ser
225                 230                 235                 240

Asn Asp Thr Ile Asn Phe Glu Ser Asn Gly Asn Phe Ile Ala Pro Glu
                245                 250                 255

Asn Ala Tyr Lys Ile Val Lys Lys Gly Asp Ser Thr Ile Met Lys Ser
                260                 265                 270

Glu Leu Glu Tyr Gly Asn Cys Asn Thr Lys Cys Gln Thr Pro Ile Gly
            275                 280                 285

Ala Ile Asn Ser Ser Met Pro Phe His Asn Ile His Pro Leu Thr Ile
    290                 295                 300

Gly Glu Cys Pro Lys Tyr Val Lys Ser Asn Arg Leu Val Leu Ala Thr
305                 310                 315                 320

Gly Leu Arg Asn Ser Pro Gln Gly Glu Gly Arg Arg Lys Lys Arg Gly
                325                 330                 335

Leu Phe Gly Ala Ile Ala Gly Phe Ile Glu Gly Gly Trp Gln Gly Met
                340                 345                 350

Val Asp Gly Trp Tyr Gly Tyr His His Ser Asn Glu Gln Gly Ser Gly
            355                 360                 365

Tyr Ala Ala Asp Lys Glu Ser Thr Gln Lys Ala Ile Asp Gly Val Thr
    370                 375                 380

Asn Lys Val Asn Ser Ile Ile Asp Lys Met Asn Thr Gln Phe Glu Ala
385                 390                 395                 400

Val Gly Arg Glu Phe Asn Asn Leu Glu Lys Arg Ile Glu Asn Leu Asn
                405                 410                 415

Lys Lys Met Glu Asp Gly Phe Leu Asp Val Trp Thr Tyr Asn Ala Glu
```

```
            420                 425                 430

Leu Leu Val Leu Met Glu Asn Glu Arg Thr Leu Asp Phe His Asp Ser
        435                 440                 445

Asn Val Lys Asn Leu Tyr Asp Lys Val Arg Leu Gln Leu Arg Asp Asn
    450                 455                 460

Ala Lys Glu Leu Gly Asn Gly Cys Phe Glu Phe Tyr His Arg Cys Asp
465                 470                 475                 480

Asn Glu Cys Met Glu Ser Val Lys Asn Gly Thr Tyr Asp Tyr Pro Gln
                485                 490                 495

Tyr Ser Glu Glu Ala Arg Leu Lys Arg Glu Glu Ile Ser Gly Val Lys
            500                 505                 510

Leu Glu Ser Ile Gly Thr Tyr Gln Ile Leu Ser Ile Tyr Ser Thr Val
        515                 520                 525

Ala Ser Ser Leu Ala Leu Ala Ile Met
    530                 535

<210> SEQ ID NO 39
<211> LENGTH: 534
<212> TYPE: PRT
<213> ORGANISM: H5N1

<400> SEQUENCE: 39

Lys Ser Asp Gln Ile Cys Ile Gly Tyr His Ala Asn Asn Ser Thr Glu
1               5                   10                  15

Gln Val Asp Thr Ile Met Glu Lys Asn Val Thr Val Thr His Ala Gln
            20                  25                  30

Asp Ile Leu Glu Lys Thr His Asn Gly Lys Leu Cys Asp Leu Asp Gly
        35                  40                  45

Val Lys Pro Leu Ile Leu Arg Asp Cys Ser Val Ala Gly Trp Leu Leu
    50                  55                  60

Gly Asn Pro Met Cys Asp Glu Phe Pro Asn Val Ser Glu Trp Ser Tyr
65                  70                  75                  80

Ile Val Glu Lys Ile Asn Pro Ala Asn Asp Leu Cys Tyr Pro Gly Asn
                85                  90                  95

Phe Asn Asn Tyr Glu Glu Leu Lys His Leu Leu Ser Arg Ile Asn Arg
            100                 105                 110

Phe Glu Lys Ile Gln Ile Ile Pro Lys Ser Ser Trp Pro Asp His Glu
        115                 120                 125

Ala Ser Leu Gly Val Ser Ser Ala Cys Pro Tyr Gln Gly Gly Pro Ser
    130                 135                 140

Phe Tyr Arg Asn Val Val Trp Leu Ile Lys Lys Asn Asp Thr Tyr Pro
145                 150                 155                 160

Thr Ile Lys Glu Ser Tyr His Asn Thr Asn Gln Glu Asp Leu Leu Val
                165                 170                 175

Leu Trp Gly Ile His His Pro Asn Asp Glu Glu Glu Gln Lys Arg Ile
            180                 185                 190

Tyr Lys Asn Pro Thr Thr Tyr Ile Ser Val Gly Thr Ser Thr Leu Asn
        195                 200                 205

Gln Arg Leu Val Pro Lys Ile Ala Thr Arg Ser Lys Val Asn Gly Gln
    210                 215                 220

Ser Gly Arg Val Glu Phe Phe Trp Thr Ile Leu Lys Ser Asn Asp Thr
225                 230                 235                 240

Ile Asn Phe Glu Ser Asn Gly Asn Phe Ile Ala Pro Glu Asn Ala Tyr
                245                 250                 255
```

Lys Ile Val Lys Lys Gly Asp Ser Thr Ile Met Lys Ser Glu Leu Glu
            260                 265                 270

Tyr Gly Asn Cys Ser Thr Lys Cys Gln Thr Pro Ile Gly Ala Ile Asn
            275                 280                 285

Thr Ser Met Pro Phe His Asn Ile His Pro Leu Thr Ile Gly Glu Cys
        290                 295                 300

Pro Lys Tyr Val Lys Ser Asn Arg Leu Val Leu Ala Thr Gly Leu Arg
305                 310                 315                 320

Asn Ser Pro Gln Gly Glu Gly Arg Arg Lys Arg Gly Leu Phe Gly
                325                 330                 335

Ala Ile Ala Gly Phe Ile Glu Gly Gly Trp Gln Gly Met Val Asp Gly
            340                 345                 350

Trp Tyr Gly Tyr His His Ser Asn Glu Gln Gly Ser Gly Tyr Ala Ala
            355                 360                 365

Asp Lys Glu Ser Thr Gln Lys Ala Ile Asn Gly Val Thr Asn Lys Val
        370                 375                 380

Asn Ser Ile Ile Asp Lys Met Asn Thr Gln Phe Glu Ala Val Gly Arg
385                 390                 395                 400

Glu Phe Asn Asn Leu Glu Lys Arg Ile Glu Asn Leu Asn Lys Lys Met
                405                 410                 415

Glu Asp Gly Phe Leu Asp Val Trp Thr Tyr Asn Ala Glu Leu Leu Val
            420                 425                 430

Leu Met Glu Asn Glu Arg Thr Leu Asp Phe His Asp Ser Asn Val Arg
        435                 440                 445

Asn Leu Tyr Asp Lys Val Arg Leu Gln Leu Arg Asp Asn Ala Lys Glu
450                 455                 460

Leu Gly Asn Gly Cys Phe Glu Phe Tyr His Arg Cys Asp Asn Glu Cys
465                 470                 475                 480

Met Glu Ser Val Arg Asn Gly Thr Tyr Asp Tyr Pro Gln Tyr Ser Lys
                485                 490                 495

Glu Ala Arg Leu Lys Arg Glu Glu Ile Ser Gly Val Lys Leu Glu Ser
            500                 505                 510

Ile Gly Thr Tyr Gln Ile Leu Ser Ile Tyr Ser Thr Val Ala Ser Ser
        515                 520                 525

Leu Ala Leu Ala Ile Met
    530

<210> SEQ ID NO 40
<211> LENGTH: 536
<212> TYPE: PRT
<213> ORGANISM: H5N1
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (311)..(311)
<223> OTHER INFORMATION: Xaa can be any naturally occurring amino acid

<400> SEQUENCE: 40

Xaa Val Lys Ser Asp Gln Ile Cys Ile Gly Tyr His Ala Asn Asn Ser
1               5                   10                  15

Thr Glu Gln Val Asp Thr Ile Met Glu Lys Asn Val Thr Val Thr His
            20                  25                  30

Ala Gln Asp Ile Leu Glu Lys Thr His Asn Gly Lys Leu Cys Asp Leu
        35                  40                  45

-continued

Asp Gly Val Lys Pro Leu Ile Leu Arg Asp Cys Ser Val Ala Gly Trp
 50              55                  60

Leu Leu Gly Asn Pro Met Cys Asp Glu Phe Pro Asn Val Ser Glu Trp
 65              70                  75                  80

Ser Tyr Ile Val Glu Lys Thr Asn Pro Ala Asn Asp Leu Cys Tyr Pro
                 85                  90                  95

Gly Asn Phe Asn Asn Tyr Glu Glu Leu Lys His Leu Leu Ser Arg Ile
             100                 105                 110

Asn Arg Phe Glu Lys Ile Lys Ile Ile Pro Lys Ser Ser Trp Pro Asp
         115                 120                 125

His Glu Ala Ser Leu Gly Val Ser Ser Ala Cys Pro Tyr Gln Gly Glu
     130                 135                 140

Pro Ser Phe Tyr Arg Asn Val Val Trp Leu Ile Lys Lys Asn Asn Thr
145                 150                 155                 160

Tyr Pro Thr Ile Lys Glu Ser Tyr His Asn Thr Asn Gln Glu Asp Leu
                 165                 170                 175

Leu Val Leu Trp Gly Ile His His Pro Asn Asp Glu Glu Glu Gln Thr
             180                 185                 190

Arg Ile Tyr Lys Asn Pro Thr Thr Tyr Ile Ser Val Gly Thr Ser Thr
         195                 200                 205

Leu Asn Gln Arg Leu Val Pro Lys Ile Ala Thr Arg Ser Lys Val Asn
210                 215                 220

Gly Gln Ser Gly Arg Val Glu Phe Phe Trp Thr Ile Leu Lys Ser Asn
225                 230                 235                 240

Asp Thr Ile Asn Phe Glu Ser Asn Gly Asn Phe Ile Ala Pro Glu Asn
                 245                 250                 255

Ala Tyr Lys Ile Val Lys Lys Gly Asp Ser Thr Ile Met Lys Ser Glu
             260                 265                 270

Leu Glu Tyr Gly Asn Cys Ser Thr Lys Cys Gln Thr Pro Val Gly Ala
         275                 280                 285

Ile Asn Ser Ser Met Pro Phe His Asn Ile His Pro Leu Thr Ile Gly
     290                 295                 300

Glu Cys Pro Lys Tyr Val Xaa Ser Asn Arg Leu Val Leu Ala Thr Gly
305                 310                 315                 320

Leu Arg Asn Ser Pro Gln Gly Glu Gly Arg Lys Lys Arg Gly Leu
                 325                 330                 335

Phe Gly Ala Ile Ala Gly Phe Ile Glu Gly Gly Trp Gln Gly Met Val
             340                 345                 350

Asp Gly Trp Tyr Gly Tyr His His Ser Asn Glu Gln Gly Ser Gly Tyr
         355                 360                 365

Ala Ala Asp Arg Glu Ser Thr Gln Lys Ala Ile Asp Gly Val Thr Asn
     370                 375                 380

Lys Val Asn Ser Ile Ile Asp Lys Met Asn Thr Gln Phe Glu Ala Val
385                 390                 395                 400

Gly Arg Glu Phe Asn Asn Leu Glu Lys Arg Ile Glu Asn Leu Asn Lys
                 405                 410                 415

Lys Met Glu Asp Gly Phe Leu Asp Val Trp Thr Tyr Asn Ala Glu Leu
             420                 425                 430

Leu Val Leu Met Glu Asn Glu Arg Thr Leu Asp Phe His Asp Ser Asn
         435                 440                 445

Val Lys Asn Leu Tyr Asp Lys Val Arg Leu Gln Leu Arg Asp Asn Ala
     450                 455                 460

Lys Glu Leu Gly Asn Gly Cys Phe Glu Phe Tyr His Arg Cys Asp Asn

-continued 465 470 475 480

Glu Cys Ile Glu Ser Val Arg Asn Gly Thr Tyr Asp Tyr Pro Gln Tyr
485 490 495

Ser Glu Glu Ala Arg Leu Lys Arg Glu Glu Ile Ser Gly Val Lys Leu
500 505 510

Glu Ser Ile Gly Thr Tyr Gln Ile Leu Ser Ile Tyr Ser Thr Val Ala
515 520 525

Ser Ser Leu Ala Leu Ala Ile Met
530 535

<210> SEQ ID NO 41
<211> LENGTH: 515
<212> TYPE: PRT
<213> ORGANISM: H5N1
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (515)..(515)
<223> OTHER INFORMATION: Xaa can be any naturally occurring amino acid

<400> SEQUENCE: 41

Xaa Leu Val Lys Ser Asp Gln Ile Cys Ile Gly Tyr His Ala Asn Asn
1 5 10 15

Ser Thr Glu Gln Val Asp Thr Ile Met Glu Lys Asn Val Thr Val Thr
20 25 30

His Ala Gln Asp Ile Leu Glu Lys Thr His Asn Gly Lys Leu Cys Asp
35 40 45

Leu Asp Gly Val Lys Pro Leu Ile Leu Arg Asp Cys Ser Val Ala Gly
50 55 60

Trp Leu Leu Gly Asn Pro Met Cys Asp Glu Phe Pro Asn Val Ser Glu
65 70 75 80

Trp Ser Tyr Ile Val Glu Lys Ile Asn Pro Ala Asn Asp Leu Cys Tyr
85 90 95

Pro Gly Asn Phe Asn Asn Tyr Glu Glu Leu Lys His Leu Leu Ser Arg
100 105 110

Ile Asn Arg Phe Glu Lys Ile Gln Ile Ile Pro Lys Ser Ser Trp Pro
115 120 125

Asp His Glu Ala Ser Leu Gly Val Ser Ser Ala Cys Pro Tyr Gln Gly
130 135 140

Gly Pro Ser Phe Tyr Arg Asn Val Val Trp Leu Ile Lys Lys Asn Asp
145 150 155 160

Thr Tyr Pro Thr Ile Lys Glu Ser Tyr His Asn Thr Asn Gln Glu Asp
165 170 175

Leu Leu Val Leu Trp Gly Ile His His Pro Asn Asp Glu Glu Glu Gln
180 185 190

Lys Arg Ile Tyr Lys Asn Pro Thr Thr Tyr Val Ser Val Gly Thr Ser
195 200 205

Thr Leu Asn Gln Arg Leu Val Pro Lys Ile Ala Thr Arg Ser Lys Val
210 215 220

Asn Gly Gln Ser Gly Arg Val Glu Phe Phe Trp Thr Ile Leu Lys Ser
225 230 235 240

Asn Asp Thr Ile Asn Phe Glu Ser Asn Gly Asn Phe Ile Ala Pro Glu
245 250 255

Asn Ala Tyr Lys Ile Val Lys Lys Gly Asp Ser Thr Ile Met Lys Ser

```
                    260                 265                 270
Glu Leu Glu Tyr Gly Asn Cys Ser Thr Lys Cys Gln Thr Pro Ile Gly
            275                 280                 285

Ala Ile Asn Thr Ser Met Pro Phe His Asn Ile His Pro Leu Thr Ile
        290                 295                 300

Gly Glu Cys Pro Lys Tyr Val Lys Ser Asn Arg Leu Val Leu Ala Thr
305                 310                 315                 320

Gly Leu Arg Asn Ser Pro Gln Gly Glu Gly Arg Arg Lys Lys Arg Gly
                325                 330                 335

Leu Phe Gly Ala Ile Ala Gly Phe Ile Glu Gly Gly Trp Gln Gly Met
            340                 345                 350

Val Asp Gly Trp Tyr Gly Tyr His His Ser Asn Glu Gln Gly Ser Gly
        355                 360                 365

Tyr Ala Ala Asp Lys Glu Ser Thr Gln Lys Ala Ile Asp Gly Val Thr
    370                 375                 380

Asn Lys Val Asn Ser Ile Ile Asp Lys Met Asn Thr Gln Phe Glu Ala
385                 390                 395                 400

Val Gly Arg Glu Phe Asn Asn Leu Glu Lys Arg Ile Glu Asn Leu Asn
                405                 410                 415

Lys Lys Met Glu Asp Gly Phe Leu Asp Val Trp Thr Tyr Asn Ala Glu
            420                 425                 430

Leu Leu Val Leu Met Glu Asn Glu Arg Thr Leu Asp Phe His Asp Ser
        435                 440                 445

Asn Val Arg Asn Leu Tyr Asp Lys Val Arg Leu Gln Leu Arg Asp Asn
    450                 455                 460

Ala Lys Glu Leu Gly Asn Gly Cys Phe Glu Phe Tyr His Arg Cys Asp
465                 470                 475                 480

Asn Glu Cys Met Glu Ser Val Arg Asn Gly Thr Tyr Asp Tyr Pro Gln
                485                 490                 495

Tyr Ser Glu Glu Ala Arg Leu Lys Arg Glu Glu Ile Ser Gly Val Lys
            500                 505                 510

Leu Glu Xaa
        515

<210> SEQ ID NO 42
<211> L

```
            65                  70                  75                  80
Ser Tyr Ile Val Glu Lys Ile Asn Pro Ala Asn Asp Leu Cys Tyr Pro
                    85                  90                  95

Gly Asp Phe Asn Asp Tyr Glu Leu Lys His Leu Leu Ser Arg Ile
                100                 105                 110

Asn His Phe Glu Lys Ile Gln Ile Ile Pro Lys Asn Ser Trp Ser Asp
            115                 120                 125

His Glu Ala Ser Gly Val Ser Ser Ala Cys Pro Tyr Gln Gly Arg Ser
        130                 135                 140

Ser Phe Phe Arg Asn Val Val Trp Leu Thr Lys Lys Asn Asn Ala Tyr
145                 150                 155                 160

Pro Thr Ile Lys Lys Ser Tyr Asn Asn Thr Asn Gln Glu Asp Leu Leu
                165                 170                 175

Val Leu Trp Gly Ile His His Pro Asn Asp Ala Ala Glu Gln Thr Met
            180                 185                 190

Leu Tyr Gln Asn Pro Thr Thr Tyr Val Ser Val Gly Thr Ser Thr Leu
        195                 200                 205

Asn Gln Arg Leu Val Pro Lys Ile Ala Thr Arg Ser Lys Val Asn Gly
    210                 215                 220

Gln Ser Gly Arg Met Glu Phe Phe Trp Thr Ile Leu Lys Ser Asn Asp
225                 230                 235                 240

Ala Ile Asn Phe Glu Ser Asn Gly Asn Phe Ile Ala Pro Glu Asn Ala
                245                 250                 255

Tyr Lys Ile Val Lys Lys Gly Asp Ser Thr Ile Met Lys Ser Glu Leu
            260                 265                 270

Glu Tyr Gly Asn Cys Asn Thr Lys Cys Gln Thr Pro Ile Gly Ala Ile
        275                 280                 285

Asn Ser Ser Met Pro Phe His Asn Ile His Pro Leu Thr Ile Gly Glu
    290                 295                 300

Cys Pro Lys Tyr Val Lys Ser Asn Arg Leu Val Leu Ala Thr Gly Leu
305                 310                 315                 320

Arg Asn Ser Pro Gln Gly Glu Arg Arg Lys Lys Arg Gly Leu Phe
                325                 330                 335

Gly Ala Ile Ala Gly Phe Ile Glu Gly Gly Trp Gln Gly Met Val Asp
            340                 345                 350

Gly Trp Tyr Gly Tyr His His Ser Asn Glu Gln Gly Ser Gly Tyr Ala
        355                 360                 365

Ala Asp Lys Glu Ser Thr Gln Lys Ala Ile Asp Gly Val Thr Asn Lys
    370                 375                 380

Val Asn Ser Ile Ile Asp Lys Met Asn Thr Gln Phe Glu Ala Val Gly
385                 390                 395                 400

Arg Glu Phe Asn Asn Leu Glu Arg Arg Ile Glu Asn Leu Asn Lys Lys
                405                 410                 415

Met Glu Asp Gly Phe Leu Asp Val Trp Thr Tyr Asn Ala Glu Leu Leu
            420                 425                 430

Val Leu Met Glu Asn Glu Arg Thr Leu Asp Phe His Asp Ser Asn Val
        435                 440                 445

Lys Asn Leu Tyr Asp Lys Val Arg Leu Gln Leu Arg Asp Asn Ala Lys
    450                 455                 460

Glu Leu Gly Asn Gly Cys Phe Glu Phe Tyr His Arg Cys Asp Asn Glu
465                 470                 475                 480

Cys Met Glu Ser Val Arg Asn Gly Thr Tyr Asp Tyr Pro Gln Tyr Ser
                485                 490                 495
```

-continued

```
Glu Glu Ala Arg Leu Lys Arg Glu Glu Ile Ser Gly Val Lys Leu Glu
            500                 505                 510

Ser Ile Gly Thr Xaa Gln Ile
        515
```

<210> SEQ ID NO 43
<211> LENGTH: 510
<212> TYPE: PRT
<213> ORGANISM: H5N1
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (507)..(507)
<223> OTHER INFORMATION: Xaa can be any naturally occurring amino acid
<220> FEATURE:
<221> NAME/KEY: misc_feature
<222> LOCATION: (510)..(510)
<223> OTHER INFORMATION: Xaa can be any naturally occurring amino acid

<400> SEQUENCE: 43

```
Xaa His Ala Asn Asn Ser Thr Glu Gln Val Asp Thr Ile Met Glu Lys
1               5                   10                  15

Asn Val Thr Val Thr His Ala Gln Asp Ile Leu Glu Lys Thr His Asn
            20                  25                  30

Gly Lys Leu Cys Asn Leu Asp Gly Val Lys Pro Leu Ile Leu Arg Asp
        35                  40                  45

Cys Ser Val Ala Gly Trp Leu Leu Gly Asn Pro Met Cys Asp Glu Phe
    50                  55                  60

Pro Asn Val Leu Glu Trp Ser Tyr Ile Val Glu Lys Ile Asn Pro Ala
65                  70                  75                  80

Asn Asp Leu Cys Tyr Pro Gly Asn Phe Asn Asp Tyr Glu Glu Leu Lys
                85                  90                  95

His Leu Leu Ser Arg Ile Asn His Phe Glu Lys Ile Gln Ile Ile Pro
            100                 105                 110

Lys Asn Ser Trp Ser Asp His Glu Ala Ser Gly Val Ser Ser Ala Cys
        115                 120                 125

Pro Tyr Gln Arg Arg Ser Ser Phe Phe Arg Asn Val Val Trp Leu Thr
    130                 135                 140

Lys Lys Asn Asn Ala Tyr Pro Thr Ile Lys Lys Ser Tyr Asn Asn Thr
145                 150                 155                 160

Asn Gln Glu Asp Leu Leu Val Leu Trp Gly Ile His His Pro Asn Asp
                165                 170                 175

Ala Ala Glu Gln Thr Arg Leu Tyr Gln Asn Pro Thr Thr Tyr Ile Ser
            180                 185                 190

Val Gly Thr Ser Thr Leu Asn Gln Arg Leu Val Pro Lys Ile Ala Thr
        195                 200                 205

Arg Ser Lys Val Asn Gly Gln Ser Gly Arg Met Glu Phe Phe Trp Thr
    210                 215                 220

Ile Leu Lys Ser Asn Asp Ala Ile Asn Phe Glu Ser Asn Gly Asn Phe
225                 230                 235                 240

Ile Ala Pro Glu Asn Ala Tyr Lys Ile Val Lys Lys Gly Asp Ser Thr
                245                 250                 255

Ile Met Lys Ser Glu Leu Glu Tyr Gly Asn Cys Asn Thr Lys Cys Gln
            260                 265                 270

Thr Pro Ile Gly Ala Ile Asn Ser Ser Met Pro Phe His Asn Ile His
```

```
                275                 280                 285
Pro Leu Thr Ile Gly Glu Cys Pro Lys Tyr Val Lys Ser Asn Arg Leu
    290                 295                 300

Val Leu Ala Thr Gly Leu Arg Asn Ser Pro Gln Gly Glu Arg Arg Arg
305                 310                 315                 320

Lys Lys Arg Gly Leu Phe Gly Ala Ile Ala Gly Phe Ile Glu Gly Gly
                325                 330                 335

Trp Gln Gly Met Val Asp Gly Trp Tyr Gly Tyr His His Ser Asn Glu
            340                 345                 350

Gln Gly Ser Gly Tyr Ala Ala Asp Lys Glu Ser Thr Gln Lys Ala Ile
                355                 360                 365

Asp Gly Val Thr Asn Lys Val Asn Ser Ile Ile Asp Lys Met Asn Thr
        370                 375                 380

Gln Phe Glu Ala Val Gly Arg Glu Phe Asn Asn Leu Glu Arg Arg Ile
385                 390                 395                 400

Glu Asn Leu Asn Lys Lys Met Glu Asp Gly Phe Leu Asp Val Trp Thr
                405                 410                 415

Tyr Asn Ala Glu Leu Leu Val Leu Met Glu Asn Glu Arg Thr Leu Asp
            420                 425                 430

Phe His Asp Ser Asn Val Lys Asn Leu Tyr Asp Lys Val Arg Leu Gln
            435                 440                 445

Leu Arg Asp Asn Ala Lys Glu Leu Gly Asn Gly Cys Phe Glu Phe Tyr
    450                 455                 460

His Arg Cys Asp Asn Glu Cys Met Glu Ser Val Arg Asn Gly Thr Tyr
465                 470                 475                 480

Asp Tyr Pro Gln Tyr Ser Glu Ala Arg Leu Lys Arg Glu Glu Ile
                485                 490                 495

Ser Gly Val Lys Leu Glu Ser Ile Gly Thr Xaa Gln Ile Xaa
                500                 505                 510

<210> SEQ ID NO 44
<211> LENGTH: 523
<212> TYPE: PRT
<213> ORGANISM: H5N1
<220> FEATURE:
<221> NAME/KEY: mis

```
Pro Tyr Gln Gly Gly Pro Ser Phe Tyr Arg Asn Val Val Trp Leu Ile
    130                 135                 140
Lys Lys Asn Asn Thr Tyr Pro Thr Ile Lys Ser Tyr His Asn Thr
145                 150                 155                 160
Asn Gln Glu Asp Leu Leu Val Leu Trp Gly Ile His His Pro Asn Asp
                    165                 170                 175
Glu Glu Glu Gln Thr Arg Ile Tyr Lys Asn Pro Thr Thr Tyr Ile Ser
                180                 185                 190
Val Gly Thr Ser Thr Leu Asn Gln Arg Leu Val Pro Lys Ile Ala Thr
            195                 200                 205
Arg Ser Lys Val Asn Gly Gln Ser Gly Arg Val Glu Phe Phe Trp Thr
        210                 215                 220
Ile Leu Lys Ser Asn Asp Thr Ile Asn Phe Glu Ser Asn Gly Asn Phe
225                 230                 235                 240
Ile Ala Pro Glu Asn Ala Tyr Lys Ile Val Lys Lys Gly Asp Ser Thr
                245                 250                 255
Ile Met Lys Ser Glu Leu Glu Tyr Gly Asn Cys Asn Thr Lys Cys Gln
                260                 265                 270
Thr Pro Ile Gly Ala Ile Asn Ser Ser Met Pro Phe His Asn Ile His
            275                 280                 285
Pro Leu Thr Ile Gly Glu Cys Pro Lys Tyr Val Lys Ser Asn Arg Leu
        290                 295                 300
Val Leu Ala Thr Gly Leu Arg Asn Ser Pro Gln Gly Glu Gly Arg Arg
305                 310                 315                 320
Lys Lys Arg Gly Leu Phe Gly Ala Ile Ala Gly Phe Ile Glu Gly Gly
                325                 330                 335
Trp Gln Gly Met Val Asp Gly Trp Tyr Gly Tyr His His Ser Asn Glu
                340                 345                 350
Gln Gly Ser Gly Tyr Ala Ala Asp Lys Glu Ser Thr Gln Lys Ala Ile
            355                 360                 365
Asp Gly Val Thr Asn Lys Val Asn Ser Ile Ile Asp Lys Met Asn Thr
        370                 375                 380
Gln Phe Glu Ala Val Gly Arg Glu Phe Asn Asn Leu Glu Lys Arg Ile
385                 390                 395                 400
Glu Asn Leu Asn Lys Lys Met Glu Asp Gly Phe Leu Asp Val Trp Thr
                405                 410                 415
Tyr Asn Ala Glu Leu Leu Val Leu Met Glu Asn Glu Arg Thr Leu Asp
                420                 425                 430
Phe His Asp Ser Asn Val Lys Asn Leu Tyr Asp Lys Val Arg Leu Gln
            435                 440                 445
Leu Arg Asp Asn Ala Lys Glu Leu Gly Asn Gly Cys Phe Glu Phe Tyr
        450                 455                 460
His Arg Cys Asp Asn Glu Cys Met Glu Ser Val Arg Asn Gly Thr Tyr
465                 470                 475                 480
Asp Tyr Pro Gln Tyr Ser Glu Glu Ala Arg Leu Lys Arg Glu Glu Ile
                485                 490                 495
Ser Gly Val Lys Leu Glu Ser Ile Gly Thr Tyr Gln Ile Leu Ile Tyr
                500                 505                 510
Ser Thr Val Ala Ser Ser Leu Ala Leu Ala Xaa
            515                 520

<210> SEQ ID NO 45
<211> LENGTH: 541
```

<212> TYPE: PRT
<213> ORGANISM: H5N1

<400> SEQUENCE: 45

```
Leu Leu Ala Ile Val Ser Leu Val L

```
Thr Gln Phe Glu Ala Val Gly Arg Glu Phe Asn Asn Leu Glu Lys Arg
                405                 410                 415

Ile Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Leu
    450                 455                 460

Gln Leu Arg Asp Asn Ala Lys Glu Leu Gly Asn Gly Cys Phe Glu Phe
465                 470                 475                 480

Tyr His Arg Cys Asp Asn Glu Cys Met Glu Ser Val Arg Asn Gly Thr
                485                 490                 495

Tyr Asp Tyr Pro Gln Tyr Ser Glu Glu Ala Arg Leu Lys Arg Glu Glu
            500                 505                 510

Ile Ser Gly Val Lys Leu Glu Ser Ile Gly Thr Tyr Gln Ile Leu Ser
        515                 520                 525

Ile Tyr Ser Thr Val Ala Ser Ser Leu Ala Leu Ala Ile
    530                 535                 540

<210> SEQ ID NO 46
<211> LENGTH: 555
<212> TYPE: PRT
<213> ORGANISM: H5N1
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (555)..(555)
<223> OTHER INFORMATION: Xaa can be any naturally occurring amino acid

<400> SEQUENCE: 46

Xaa Leu Ala Ile Val Ser Leu Val Lys Ser Asp Gln Ile Cys Ile Gly
1               5                   10                  15

Tyr His Ala Asn Asn Ser Thr Glu Gln Val Asp Thr Ile Met Glu Lys
            20                  25                  30

Asn Val Thr Val Thr His Ala Gln Asp Ile Leu Glu Lys Thr His Asn
        35                  40                  45

Gly Lys Leu Cys Asp Leu Asp Gly Val Lys Pro Leu Ile Leu Arg Asp
    50                  55                  60

Cys Ser Val Ala Gly Trp Leu Leu Gly Asn Pro Met Cys Asp Glu Phe
65                  70                  75                  80

Pro Asn Val Ser Glu Trp Ser Tyr Ile Val Glu Lys Ile Asn Pro Ala
                85                  90                  95

Asn Asp Leu Cys Tyr Pro Gly Asn Phe Asn Asn Tyr Glu Glu Leu Lys
            100                 105                 110

His Leu Leu Ser Arg Ile Asn Arg Phe Glu Lys Ile Lys Ile Ile Pro
        115                 120                 125

Lys Ser Ser Trp Pro Asp His Glu Ala Ser Leu Gly Val Ser Ser Ala
    130                 135                 140

Cys Pro Tyr Gln Gly Gly Pro Ser Phe Tyr Arg Asn Val Val Trp Leu
145                 150                 155                 160

Thr Lys Lys Asn Asn Thr Tyr Pro Thr Ile Lys Lys Ser Tyr His Asn
                165                 170                 175

Ile Asn Lys Glu Asp Leu Leu Val Leu Trp Gly Ile His His Pro Asn
            180                 185                 190
```

Asp Glu Glu Glu Gln Ile Arg Ile Tyr Lys Asn Pro Thr Thr Tyr Ile
            195                 200                 205

Ser Val Gly Thr Ser Thr Leu Asn Gln Arg Leu Val Pro Lys Ile Ala
    210                 215                 220

Thr Arg Ser Lys Val Asn Gly Gln Ser Gly Arg Val Glu Phe Phe Trp
225                 230                 235                 240

Thr Ile Leu Lys Ser Asn Asp Thr Ile Asn Phe Glu Ser Asn Gly Asn
                245                 250                 255

Phe Ile Ala Pro Glu Asn Ala Tyr Lys Ile Val Lys Lys Gly Asp Ser
                260                 265                 270

Thr Ile Met Lys Ser Glu Leu Glu Tyr Gly Asn Cys Asn Thr Lys Cys
            275                 280                 285

Gln Thr Pro Ile Gly Ala Ile Asn Ser Ser Met Pro Phe His Asn Ile
        290                 295                 300

His Pro Leu Thr Ile Gly Glu Cys Pro Lys Tyr Val Lys Ser Asn Arg
305                 310                 315                 320

Leu Val Leu Ala Thr Gly Leu Arg Asn Ser Pro Gln Gly Glu Gly Arg
                325                 330                 335

Arg Lys Lys Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Glu Gln Gly Ser Gly Tyr Ala Ala Asp Lys Glu Ser Thr Gln Lys Ala
    370                 375                 380

Ile Asp Gly Val Thr Asn Lys Val Asn Ser Ile Ile Asp Lys Met Asn
385                 390                 395                 400

Thr Gln Phe Glu Ala Val Gly Arg Glu Phe Asn Asn Leu Glu Lys Arg
                405                 410                 415

Ile Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Leu
    450                 455                 460

Gln Leu Arg Asp Asn Ala Lys Glu Leu Gly Asn Gly Cys Phe Glu Phe
465                 470                 475                 480

Tyr His Arg Cys Asp Asn Glu Cys Met Glu Ser Val Arg Asn Gly Thr
                485                 490                 495

Tyr Asp Tyr Pro Gln Tyr Ser Glu Glu Ala Arg Leu Lys Arg Glu Glu
            500                 505                 510

Ile Ser Gly Val Lys Leu Glu Ser Ile Gly Thr Tyr Gln Ile Leu Ser
        515                 520                 525

Ile Tyr Ser Thr Val Ala Ser Ser Leu Ala Leu Ala Ile Met Met Ala
    530                 535                 540

Gly Leu Phe Leu Trp Met Cys Ser Asn Gly Xaa
545                 550                 555

<210> SEQ ID NO 47
<211> LENGTH: 568
<212> TYPE: PRT
<213> ORGANISM: Artificial
<220> FEATURE:
<223> OTHER INFORMATION: consensus sequence translated into protein

<400> SEQUENCE: 47

-continued

```
Met Glu Lys Ile Val Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
            35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Pro Asn Val Ser Trp Ser Tyr Ile Val
                85                  90                  95

Glu Lys Ile Asn Pro Ala Asn Asp Leu Cys Tyr Pro Gly Asn Phe Asn
                100                 105                 110

Asn Tyr Glu Glu Leu Lys His Leu Leu Ser Arg Ile Asn Arg Phe Glu
            115                 120                 125

Lys Ile Gln Ile Ile Pro Lys Ser Ser Trp Pro Asp His Glu Ala Ser
    130                 135                 140

Leu Gly Val Ser Ser Ala Cys Pro Tyr Gln Gly Gly Pro Ser Phe Tyr
145                 150                 155                 160

Arg Asn Val Val Trp Leu Ile Lys Lys Asn Asn Thr Tyr Pro Thr Ile
                165                 170                 175

Lys Glu Ser Tyr His Asn Thr Asn Gln Glu Asp Leu Leu Val Leu Trp
                180                 185                 190

Gly Ile His His Pro Asn Asp Glu Glu Glu Gln Thr Arg Ile Tyr Lys
            195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Val Glu Phe Phe Trp Thr Ile Leu Lys Ser Asn Asp Thr Ile Asn
                245                 250                 255

Phe Glu Ser Asn Gly Asn Phe Ile Ala Pro Glu Asn Ala Tyr Lys Ile
            260                 265                 270

Val Lys Lys Gly Asp Ser Thr Ile Met Lys Ser Glu Leu Glu Tyr Gly
    275                 280                 285

Asn Cys Asn Thr Lys Cys Gln Thr Pro Ile Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Gly Glu Gly Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
            355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415
```

-continued

```
Asn Asn Leu Glu Lys Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Arg Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Val Ala Gly Leu Phe Leu Trp Met Cys Ser Asn Gly
545                 550                 555                 560

Ser Leu Gln Cys Arg Ile Cys Ile
                565
```

```
<210> SEQ ID NO 48
<211> LENGTH: 1620
<212> TYPE: DNA
<213> ORGANISM: H5N1

<400> SEQUENCE: 48
caatagtcag tattgttaaa agtgatcaga tttgcattgg ttaccatgca aacaactcga      60
cagagcaggt tgacacaata atggaaaaga acgtcactgt tacacacgcc caagacatac     120
tggaaaagac acacaacggg aaactctgca atctagatgg agtgaagcct ctaattttaa     180
gagattgtag tgtagctgga tggctcctag ggaacccaat gtgcgacgaa ttcctcaatg     240
tgccggaatg gtcttacata gtggagaaga tcaatccaac caatgacctc tgttatccag     300
ggaatttcaa cgactatgaa gaactgaaac acctattgag cagaataaac cattttgaga     360
aaattcagat cattcccaaa aattcttggt cagatcatga agcctcagga gtgagctcag     420
catgtccata ccagggaaga tcctcctttt ttagaaatgt ggtatggctt accaaaaaga     480
acaatgcata cccaacaata aagaaaagtt acaataatac caaccaagaa gatcttttgg     540
tattatgggg gattcaccat ccaaatgatg cggcagagca gacaaggctt tatcaaaacc     600
caactaccta tatttccgtt gggacatcaa cactaaacca gagattggta cccaaaatag     660
ctactagatc taaggtaaac gggcaaagtg gaaggatgga gttcttttgg acaattttaa     720
aatcgaatga tgcaataaac tttgagagta atggaaattt cattgctcca gaaaatgcat     780
acaaaattgt caagaaaggg gactcaacaa ttatgaaaag tgagttggaa tatggtgact     840
gcaacaccaa gtgtcagact ccaatagggg cgataaactc cagtatgcca ttccacaaca     900
tccaccctct caccatcggg gaatgcccca aatatgtgaa atcaaacaga ttagtccttg     960
ctactgggct cagaaatagc cctcaaggag agagaagaag aaaaaagaga ggactatttg    1020
gagctatagc aggttttata gagggaggat ggcagggaat ggtagatggt tggtatgggt    1080
accaccatag caacgagcag gggagtgggt acgctgcaga caaagaatcc actcaaaagg    1140
caatagatgg agtcaccaat aaggtcaact cgatcattga caaaatgaac actcagtttg    1200
aggctgttgg gagggaattt aataacttag aaaggagaat agaaaattta aacaagaaga    1260
```

| | |
|---|---|
| tggaagacgg attcctagat gtctggactt ataatgctga acttctggtt ctcatggaaa | 1320 |
| atgagagaac tctagacttt catgactcaa atgtcaagaa cctttatgac aaggtccgac | 1380 |
| tacagcttag ggataatgca aaggagcttg gtaacggttg tttcgagttc tatcacagat | 1440 |
| gtgataatga atgtatggaa agtgtaagaa acggtacgta tgactacccg cagtattcag | 1500 |
| aagaagcaag attaaaaaga gaggaaataa gtggagtaaa attggagtca ataggaactt | 1560 |
| accaaatact gtcaatttat tcaacagtgg cgagctccct agcactggca atcatggtgg | 1620 |

<210> SEQ ID NO 49
<211> LENGTH: 1707
<212> TYPE: DNA
<213> ORGANISM: H5N1

<400> SEQUENCE: 49

| | |
|---|---|
| atggagaaaa tagtgcttct tcttgcaata gtcagtcttg ttaaaagtga tcagatttgc | 60 |
| attggttacc atgcaaacaa ctcaacagag caggttgaca caataatgga aaagaacgtc | 120 |
| actgttacac acgctcaaga catactggaa agacacacaa tgggaaaact ctgcgatcta | 180 |
| ggtgagtga agcctctaat tttaagagat tgtagtgtag ctggatggct cctcgggaac | 240 |
| ccaatgtgtg acgaattccc caatgtgtcg gaatggtcct acatagtgga aagatcaat | 300 |
| ccagccaatg acctctgtta cccagggaat ttcaacaact atgaagaact gaaacatcta | 360 |
| ttgagcagaa taaaccggtt tgagaaaatt cagatcatcc ccaaaagttc ttggccagat | 420 |
| catgaagcct cattaggagt gagctcagca tgtccatacc agggaggacc ctccttttat | 480 |
| agaaatgtgg tatggcttat caaaaagaac gatacatacc caacaataaa ggaaagttac | 540 |
| cataataccc atcaagaaga tcttttggtg ctgtggggga tccaccatcc aaataatgag | 600 |
| gaagaacaga aaaggatcta taaaaaccca actacctatg tttccgttgg gacatcaaca | 660 |
| ctaaaccaga gattggtacc gaagatagcc actagatcta aggtaaacgg gcaaagtgga | 720 |
| agagtggagt tcttttggac aattttaaaa tcaaatgata caataaactt tgagagtaat | 780 |
| ggaaatttca ttgctccaga aaatgcatac aaaattgtca agaaagggga ctcaacaatt | 840 |
| atgaaaagtg agttggaata tggtaactgc agcaccaagt gtcaaactcc aatagggcg | 900 |
| ataaacacca gtatgccatt ccacaacatc caccctctca ccatcgggga atgccccaaa | 960 |
| tatgtgaaat caaacagatt agtccttgct actgggctta gaaatagccc tcaaggagag | 1020 |
| ggaagaagaa aaaagagagg actatttgga gctatagcag gttttataga gggaggatgg | 1080 |
| cagggaatgg tagatggttg gtatgggtac caccatagta acgagcaggg gagtgggtac | 1140 |
| gctgcagaca agaatccac tcaaaaggca atagatggag tcaccaataa ggtcaactcg | 1200 |
| atcattgaca aaatgaatac tcagtttgag gctgttggga ggaatttaa taacttggaa | 1260 |
| aagagaatag aaaatttaaa caagaagatg gaagacgggt tcctagatgt ctggacttat | 1320 |
| aatgctgaac ttctggttct catggaaaat gagagaactc tagactttca tgactcaaat | 1380 |
| gtcaggaacc tttacgacaa ggtgcgacta cagcttaggg acaatgcaaa ggagcttggt | 1440 |
| aacggttgtt tcgagttcta tcacagatgc gataatgaat gtatggaaag tgtaagaaac | 1500 |
| ggaacgtatg actacccgca gtattcagaa gaagcaagat taaaagagag gaaataagt | 1560 |
| ggagtaaaat tggaatcaat aggaacttac caaatactat caatttattc aacagtggca | 1620 |
| agttccctag cactggcaat catggtggct ggtctatttt tatggatgtg ctccaatgga | 1680 |
| tcgttacaat gcagaatttg catttaa | 1707 |

<210> SEQ ID NO 50
<211> LENGTH: 1707
<212> TYPE: DNA
<213> ORGANISM: Artificial
<220> FEATURE:
<223> OTHER INFORMATION: consensus of 38 H5 gene sequences

<400> SEQUENCE: 50
atggagaaaa tagtgcttct tcttgcaata gtcagtcttg ttaaaagtga tcagatttgc 60
attggttacc atgcaaacaa ctcaacagag caggttgaca caataatgga aaagaacgtc 120
actgttacac acgctcaaga catactggaa aagacacaca acgggaaact ctgcgatcta 180
gatggagtga agcctctaat ttaagagat tgtagtgtag ctggatggct cctcgggaac 240
ccaatgtgtg acgaattccc caatgtgtcg gaatggtcct acatagtgga gaagatcaat 300
ccagccaatg acctctgtta cccagggaat ttcaacaact atgaagaact gaaacaccta 360
ttgagcagaa taaaccggtt tgagaaaatt cagatcatcc ccaaaagttc ttggccagat 420
catgaagcct cattaggagt gagctcagca tgtccatacc agggaggacc ctccttttat 480
agaaatgtgg tatggcttat caaaaagaac aatacatacc caacaataaa ggaaagttac 540
cataatacca atcaagaaga tcttttggtg ctgtggggga ttcaccatcc aaatgatgag 600
gaagagcaga caaggatcta taaaaaccca actacctata tttccgttgg gacatcaaca 660
ctaaaccaga gattggtacc aaagatagcc actagatcta aggtaaacgg gcaaagtgga 720
agagtggagt tcttttggac aattttaaaa tcaaatgata caataaactt tgagagtaat 780
ggaaatttca ttgctccaga aaatgcatac aaaattgtca agaaagggga ctcaacaatt 840
atgaaaagtg agttggaata tggtaactgc aacaccaagt gtcaaactcc aataggggcg 900
ataaactcca gtatgccatt ccacaacatc caccctctca ccatcgggga atgccccaaa 960
tatgtgaaat caaacagatt agtccttgct actgggctca gaaatagccc tcaaggagag 1020
ggaagaagaa aaaagagagg actatttgga gctatagcag gttttataga gggaggatgg 1080
cagggaatgg tagatggttg gtatgggtac caccatagca acgagcaggg gagtgggtac 1140
gctgcagaca aagaatccac tcaaaaggca atagatggag tcaccaataa ggtcaactcg 1200
atcattgaca aaatgaatac tcagtttgag gctgttggga gggaatttaa taacttggaa 1260
aagagaatag aaaatttaaa caagaagatg gaagacgggt tcctagatgt ctggacttat 1320
aatgctgaac ttctggttct catggaaaat gagagaactc tagactttca tgactcaaat 1380
gtcaagaacc tttacgacaa ggtgcgacta cagcttaggg acaatgcaaa ggagcttggt 1440
aacggttgtt tcgagttcta tcacagatgc gataatgaat gtatggaaag tgtaagaaac 1500
ggaacgtatg actacccgca gtattcagaa gaagcaagat taaaaagaga ggaaataagt 1560
ggagtaaaat tggaatcaat aggaacttac caaatactat caatttattc aacagtggca 1620
agttccctag cactggcaat catggtggct ggtctatttt tatggatgtg ctccaatgga 1680
tcgttacaat gcagaatttg catttaa 1707

<210> SEQ ID NO 51
<211> LENGTH: 15186
<212> TYPE: DNA
<213> ORGANISM: Newcastle disease virus

<400> SEQUENCE: 51
accaaacaga gaatccgtga gttacgataa aaggcgaagg agcaattgaa gtcgcacggg 60
tagaaggtgt gaatctcgag tgcgagcccg aagcacaaac tcgagaaagc cttctgccaa 120

```
catgtcttcc gtatttgatg agtacgaaca gctcctcgcg gctcagactc gccccaatgg    180
agctcatgga gggggagaaa aagggagtac cttaaaagta gacgtccgg tattcactct    240 taacagtgat gacccagaag atagatggag ctttgtggta ttctgcctcc ggattgctgt    300
tagcgaagat gccaacaaac cactcaggca aggtgctctc atatctcttt tatgctccca    360
ctcacaggta atgaggaacc atgttgccct tgcagggaaa cagaatgaag ccacattggc    420
cgtgcttgag attgatggct tgccaacgg cacgccccag ttcaacaata ggagtggagt    480
gtctgaagag agagcacaga gatttgcgat gatagcagga tctctccctc gggcatgcag    540
caacggaacc ccgttcgtca cagccggggc cgaagatgat gcaccagaag acatcaccga    600
taccctggag aggatcctct ctatccaggc tcaagtatgg gtcacagtag caaaagccat    660
gactgcgtat gagactgcag atgagtcgga acaaggcga atcaataagt atatgcagca    720
aggcagggtc caaaagaaat acatcctcta ccccgtatgc aggagcacaa tccaactcac    780
gatcagacag tctcttgcag tccgcatctt tttggttagc gagctcaaga gaggccgcaa    840
cacggcaggt ggtacctcta cttattataa cctggtaggg gacgtagact catacatcag    900
gaataccggg cttactgcat tcttcttgac actcaagtac ggaatcaaca ccaagacatc    960
agcccttgca cttagtagcc tctcaggcga catccagaag atgaagcagc tcatgcgttt    1020
gtatcggatg aaaggagata atgcgccgta catgacatta cttggtgata gtgaccagat    1080
gagctttgcg cctgccgagt atgcacaact ttactccttt gccatgggta tggcatcagt    1140
cctagataaa ggtactggga ataccaatt tgccagggac tttatgagca catcattctg    1200
gagacttgga gtagagtacg ctcaggctca gggaagtagc attaacgagg atatggctgc    1260
cgagctaaag ctaaccccag cagcaaggag gggcctggca gctgctgccc aacgggtctc    1320
cgaggagacc agcagcatag acatgcctac tcaacaagtc ggagtcctca ctgggcttag    1380
cgaggggggg tcccaagctc tacaaggcgg atcgaataga tcgcaagggc aaccagaagc    1440
cggggatggg gagacccaat tcctggatct gatgagagcg gtagcaaata gcatgaggga    1500
ggcgccaaac tctgcacagg gcactcccca atcggggcct ccccaactc ctgggcatc    1560 ccaagataac gacaccgact gggggtattg ataaacaaaa cccagcctgc ttccacaaaa    1620
acatcccaat gccctcaccc gtagtcgacc cctcgatttg cggctctata tgaccacacc    1680
ctcaaacaaa catcccctc tttcctccct ccccctgctg tacaactccg cacgccctag    1740
ataccacagg cacaatgcgg ctcactaaca atcaaaacag agccgaggga attagaaaaa    1800
agtacgggta gaagagggat attcagagat cagggcaagt ctcccgagtc tctgctctct    1860
cctctacctg atagaccagg acaaacatgg ccacctttac ggatgcagag atcgacgagc    1920
tatttgagac aagtggaact gtcattgaca acataattac agcccagggt aaaccagcag    1980
agactgttgg aaggagtgca atcccacaag gcaagaccaa ggtgctgagc gcagcatggg    2040
agaagcatgg gagcatccag ccaccggcca gtcaagacaa ccccgatcga caggacagat    2100
ctgacaaaca accatccaca cccgagcaaa cgaccccgca tgacagcccg ccggccacat    2160
ccgccgacca gcccccacc caggccacag acgaagccgt cgacacacag ctcaggaccg    2220
gagcaagcaa ctctctgctg ttgatgcttg acaagctcag caataaatcg tccaatgcta    2280
aaaagggccc atggtcgagc ccccaagagg ggaatcacca acgtccgact caacagcagg    2340
ggagtcaacc cagtcgcgga aacagtcagg aaagaccgca gaaccaagtc aaggccgccc    2400 ctggaaaacca gggcacagac gtgaacacag catatcatgg acaatgggag gagtcacaac    2460
```

```
tatcagctgg tgcaaccect catgctctcc gatcaaggca gagccaagac aatacccttg    2520
tatctgcgga tcatgtccag ccacctgtag actttgtgca agcgatgatg tctatgatgg    2580
aggcgatatc acagagagta agtaaggttg actatcagct agatcttgtc ttgaaacaga    2640
catcctccat ccctatgatg cggtccgaaa tccaacagct gaaaacatct gttgcagtca    2700
tggaagccaa cttgggaatg atgaagattc tggatcccgg ttgtgccaac atttcatctc    2760
tgagtgatct acgggcagtt gcccgatctc acccggtttt agtttcaggc cctggagacc    2820
cctctcccta tgtgacacaa ggaggcgaaa tggcacttaa taaactttcg caaccagtgc    2880
cacatccatc tgaattgatt aaacccgcca ctgcatgcgg gcctgatata ggagtggaaa    2940
aggacactgt ccgtgcattg atcatgtcac gcccaatgca cccgagttct tcagccaagc    3000
tcctaagcaa gttagatgca gccggtcga tcgaggaaat caggaaaatc aagcgccttg     3060
ctctaaatgg ctaattacta ctgccacacg cagcgggtcc ctgtccactc ggcatcacac    3120
ggaatctgca ccgagttccc ccccgcagac ccaaggtcca actctccaag cggcaatcct    3180
ctctcgcttc ctcagcccca ctgaatgac gcgtaaccgt aattaatcta gctacattta     3240
agattaagaa aaaatacggg tagaattgga gtgccccaat tgtgccaaga tggactcatc    3300
taggacaatt gggctgtact ttgattctgc ccattcttct agcaacctgt tagcatttcc    3360
gatcgtccta caaggcacag agatgggaa gaagcaaatc gccccgcaat ataggatcca     3420
gcgccttgac ttgtgactg atagtaagga ggactcagta ttcatcacca cctatggatt    3480
catctttcaa gttgggaatg aagaagccac tgtcggcatg atcgatgata aacccaagcg    3540
cgagttactt tccgctgcga tgctctgcct aggaagcgtc ccaaataccg agacccttat    3600
tgagctggca agggcctgtc tcactatgat agtcacatgc aagaagagtg caactaatac    3660
tgagagaatg gttttctcag tagtgcaggc accccaagtg ctgcaaagct gtagggttgt    3720
ggcaaacaaa tactcatcag tgaatgcagt caagcacgtg aaagcgccag agaagattcc    3780
cgggagtgga ccctagaat ataaggtgaa cttttgtctcc ttgactgtgg taccgaagaa     3840
ggatgtctac aagatcccag ctgcagtatt gaaggtttct ggctcgagtc tgtacaatct    3900
tgcgctcaat gtcactatta atgtggaggt tgacccgagg agtcctttgg ttaaatctct    3960
gtctaagtct gacagcggat actatgctaa cctcttcttg catattggac ttatgaccac    4020
cgtagatagg aagggaaga aagtgacatt tgacaagctg gaaaagaaaa taaggagcct     4080
tgatctatct gtcgggctca gtgatgtgct cgggccttcc gtgttggtaa agcaagagg     4140
tgcacggact aagcttttgg cacctttctt ctctagcagt gggacagcct gctatcccat    4200
agcaaatgct tctcctcagg tggccaagat actctggagt caaaccgcgt gcctgcggag    4260
cgttaaaatc attatccaag caggtaccca acgcgctgtc gcagtgaccg ccgaccacga    4320
ggttacctct actaagctgg agaaggggca cacccttgcc aaatacaatc cttttaagaa    4380
ataagctgcg tctctgagat tgcgctccgc ccactcaccc agatcatcat gacacaaaaa    4440
actaatctgt cttgattatt tacagttagt ttacctgcct atcaagttag aaaaaacacg    4500
ggtagaagat tctggatccc ggttggcgcc ctccaggtgc aagatgggct ccagaccttc    4560
taccaagaac ccagcaccta tgatgctgac tatccgggtt gcgctggtac tgagttgcat    4620
ctgtccggca aactccattg atggcaggcc tcttgcagct gcaggaattg tggttacagg    4680
agacaaagcc gtcaacatat acacctcatc ccagacagga tcaatcatag ttaagctcct    4740
cccgaatctg cccaaggata aggaggcatg tgcgaaagcc cccttggatg catacaacag    4800
gacattgacc actttgctca cccccccttgg tgactctatc cgtaggatac aagagtctgt    4860
```

```
gactacatct ggagggggga gacaggggcg ccttataggc gccattattg gcggtgtggc   4920
tcttggggtt gcaactgccg cacaaataac agcggccgca gctctgatac aagccaaaca   4980
aaatgctgcc aacatcctcc gacttaaaga gagcattgcc gcaaccaatg aggctgtgca   5040
tgaggtcact gacggattat cgcaactagc agtggcagtt gggaagatgc agcagtttgt   5100
taatgaccaa cttaataaaa cagctcagga attagactgc atcaaaattg cacagcaagt   5160
tggtgtagag ctcaacctgt acctaaccga attgactaca gtattcggac cacaaatcac   5220
ttcacctgct ttaaacaagc tgactattca ggcactttac aatctagctg gtggaaatat   5280
ggattactta ttgactaagt taggtgtagg gaacaatcaa ctcagctcat taatcggtag   5340
cggcttaatc accggtaacc ctattctata cgactcacag actcaactct tgggtatacg   5400
ggtaactcta ccttcagtcg ggaacctaaa taatatgcgt gccacctact tggaaacctt   5460
atccgtaagc acaaccaggg gatttgcctc ggcacttgtc cccaaagtgg tgacacaggt   5520
cggttctgtg atagaagaac ttgacacctc atactgtata gaaactgact tagatttata   5580
ttgtacaaga atagtaacgt tccctatgtc ccctggtatt tattcctgct tgagcggcaa   5640
tacgtcggcc tgtatgtact caaagaccga aggcgcactt actacaccat acatgactat   5700
caaaggttca gtcatcgcca actgcaagat gacaacatgt agatgtgtaa accccccggg   5760
tatcatatcg caaaactatg gagaagccgt gtctctaata gataaacaat catgcaatgt   5820
tttatcctta ggcgggataa cttttaaggct cagtggggaa ttcgatgtaa cttatcagaa   5880
gaatatctca atacaagatt ctcaagtaat aataacaggc aatcttgata tctcaactga   5940
gcttgggaat gtcaacaact cgatcagtaa tgctttgaat aagttagagg aaagcaacag   6000
aaaactagac aaagtcaatg tcaaactgac tagcacatct gctctcatta cctatatcgt   6060
tttgactatc atatctcttg tttttggtat acttagcctg attctagcat gctacctaat   6120
gtacaagcaa aaggcgcaac aaaagaccct attatggctt gggaataata ctctagatca   6180
gatgagagcc actacaaaaa tgtgaacaca gatgaggaac gaaggtttcc ctaatagtaa   6240
tttgtgtgaa agttctggta gtctgtcagt tcagagggtt aagaaaaaac taccggttgt   6300
agatgaccaa aggacgatat acgggtagaa cggtaagaga ggccgcccct caattgcgag   6360
ccaggcttca caacctccgt tctaccgctt caccgacaac ggtcctcaat catggaccgc   6420
gccgttagcc aagttgcgtt agagaatgat gaaagagagg caaaaaatac atggcgcttg   6480
atattccgga ttgcaatctt attcttaaca gtagtgacct tggctatatc tgtagcctcc   6540
cttttatata gcatggggc tagcacacct agcgatcttg taggcatacc gactaggaat   6600
tccagggcag aagaaaagat tacatctaca cttggttcca atcaagatgt agtagatagg   6660
atatataagc aagtggccct tgagtctccg ttggcattgt taaaaactga gccacaatt   6720 atgaacgcaa taacatctct ctcttatcag attaatggag ctgcaaacaa cagtgggtgg   6780
ggggcactta tccatgaccc agattatata gggggggatag gcaagaact cattgtagat   6840 gatgctagtg atgtcacatc attctatccc tctgcatttc aagaacatct gaattttatc   6900
ccggcgccta ctacaggatc aggttgcact cgaatacct catttgacat gagtgctacc   6960
cattactgct acacccataa tgtaatattg tctggatgca gagatcactc acattcatat   7020
cagtatttag cacttggtgt gctccggaca tctgcaacag ggagggtatt cttttctact   7080
ctgcgttcca tcaacctgga cgacacccaa aatcggaagt cttgcagtgt gagtgcaact   7140
cccctgggtt gtgatatgct gtgctcgaaa gtcacggaga cagaggaaga agattataac   7200
```

```
tcagctgtcc ctacgcggat ggtacatggg aggttagggt tcgacggcca gtaccacgaa    7260
aaggacctag atgtcacaac attattcggg gactgggtgg ccaactaccc aggagtaggg    7320
ggtggatctt ttattgacag ccgcgtatgg ttctcagtct acggagggtt aaaacccaat    7380
tcacccagtg acactgtaca ggaagggaaa tatgtgatat acaagcgata caatgacaca    7440
tgcccagatg agcaagacta ccagattcga atggccaggt cttcgtataa gcctggacgg    7500
tttggtggga aacgcataca gcaggctatc ttatctatca aggtgtcaac atccttaggc    7560
gaagacccgg tactgactgt accgcccaac acagtcacac tcatggggc cgaaggcaga    7620 attctcacag tagggacatc tcatttcttg tatcaacgag ggtcatcata cttctctccc    7680
gcgttattat atcctatgac agtcagcaac aaaacagcca ctcttcatag tccttataca    7740
ttcaatgcct tcactcggcc aggtagtatc ccttgccagg cttcagcaag atgcccaac    7800 ccgtgtgtta ctggagtcta tacagatcca catcccctaa tcttctatag aaaccacacc    7860
ttgcgagggg tattcgggac aatgcttgat ggtgtacaag caagacttaa ccctgcgtct    7920
gcagtattcg atagcacatc ccgcagtcgc attactcgag tgagttcaag cagtaccaaa    7980
gcagcataca caacatcaac ttgttttaaa gtggtcaaga ctaataagac ctattgtctc    8040
agcattgctg aaatatctaa tactctcttc ggagaattca gaatcgtccc gttactagtt    8100
gagatcctca aagatgacgg ggttagagaa gccaggtctg gctagttgag tcaattataa    8160
aggagttgga aagatggcat tgtatcacct atcttctgcg acatcaagaa tcaaaccgaa    8220
tgccggcgcg tgctcgaatt ccatgttgcc agttgaccac aatcagccag tgctcatgcg    8280
atcagattaa gccttgtcaa tagtctcttg attaagaaaa aatgtaagtg gcaatgagat    8340
acaaggcaaa acagctcatg gtaaataata cgggtagaac atggcgagct ccggtcctga    8400
aagggcagag catcagatta tcctaccaga gtcacacctg tcttcaccat tggtcaagca    8460
caaactactc tattactgga aattaactgg gctaccgctt cctgatgaat gtgacttcga    8520
ccacctcatt ctcagccgac aatggaaaaa aatacttgaa tcggcctctc ctgatactga    8580
gagaatgata aaactcggaa gggcagtaca ccaaactctt aaccacaatt ccagaataac    8640
cggagtgctc cacccaggt gtttagaaga actggctaat attgaggtcc cagattcaac    8700
caacaaattt cggaagattg agaagaagat ccaaattcac aacacgagat atggagaact    8760
gttcacaagg ctgtgtacgc atatagaaa gaaactgctg gggtcatctt ggtctaacaa    8820
tgtcccccgg tcagaggagt tcagcagcat ccgtacggac ccggcattct ggtttcactc    8880
aaaatggtcc acagccaagt ttgcatggct ccatataaaa cagatccaga ggcatctgat    8940
ggtggcagct aggacaaggt ctgcggccaa caaattggtg atgctaaccc ataaggtagg    9000
ccaagtcttt gtcactcctg aacttgtcgt tgtgacgcat acgaatgaga acaagttcac    9060
atgtcttacc caggaacttg tattgatgta tgcagatatg atggagggca gagatatggt    9120
caacataata tcaaccacgg cggtgcatct cagaagctta tcagagaaaa ttgatgacat    9180
tttgcggtta atagacgctc tggcaaaaga cttgggtaat caagtctacg atgttgtatc    9240
actaatggag ggatttgcat acggagctgt ccagctactc gagccgtcag gtacatttgc    9300
aggagatttc ttcgcattca acctgcagga gcttaaagac attctaattg gcctcctccc    9360
caatgatata gcagaatccg tgactcatgc aatcgctact gtattctctg gtttagaaca    9420
gaatcaagca gctgagatgt tgtgtctgtt gcgtctgtgg ggtcacccac tgcttgagtc    9480
ccgtattgcc gcaaaggcag tcaggagcca aatgtgcgca ccgaaaatgg tagactttga    9540
tatgatcctt caggtactgt cttctcttcaa gggaacaatc atcaacgggt acagaaagaa    9600
```

```
gaatgcaggt gtgtggccgc gagtcaaagt ggatacaata tatgggaagg tcattgggca   9660
actacatgca gattcagcag agatttcaca cgatatcatg ttgagagagt ataagagttt   9720
atctgcactt gaatttgagc catgtataga atatgaccct gtcaccaacc tgagcatgtt   9780
cctaaaagac aaggcaatcg cacaccccaa cgataattgg cttgcctcgt ttaggcggaa   9840
ccttctctcc gaagaccaga agaaacatgt aaaagaagca acttcgacta atcgcctctt   9900
gatagagttt ttagagtcaa atgatttttga tccatataaa gagatggaat atctgacgac   9960
ccttgagtac cttagagatg acaatgtggc agtatcatac tcgctcaagg agaaggaagt  10020
gaaagttaat ggacggatct tcgctaagct gacaaagaag ttaaggaact gtcaggtgat  10080
ggcggaaggg atcctagccg atcagattgc acctttcttt cagggaaatg gagtcattca  10140
ggatagcata tccttgacca agagtatgct agcgatgagt caactgtctt ttaacagcaa  10200
taagaaacgt atcactgact gtaaagaaag agtatcttca aaccgcaatc atgatccgaa  10260
aagcaagaac cgtcggagag ttgcaacctt cataacaact gacctgcaaa agtactgtct  10320
taattggaga tatcagacaa tcaaattgtt cgctcatgcc atcaatcagt tgatgggcct  10380
acctcacttc ttcgaatgga ttcacctaag actgatggac actacgatgt tcgtaggaga  10440
ccctttcaat cctccaagtg accctactga ctgtgacctc tcaagagtcc ctaatgatga  10500
catatatatt gtcagtgcca gagggggtat cgaaggatta tgccagaagc tatggacaat  10560
gatctcaatt gctgcaatcc aacttgctgc agctagatcg cattgtcgtg ttgcctgtat  10620
ggtacagggt gataatcaag taatagcagt aacgagagag gtaagatcag acgactctcc  10680
ggagatggtg ttgacacagt tgcatcaagc cagtgataat ttcttcaagg aattaattca  10740
tgtcaatcat ttgattggcc ataatttgaa ggatcgtgaa accatcaggt cagacacatt  10800
cttcatatac agcaaacgaa tcttcaaaga tggagcaatc ctcagtcaag tcctcaaaaa  10860
ttcatctaaa ttagtgctag tgtcaggtga tctcagtgaa acaccgtaa tgtcctgtgc  10920 caacattgcc tctactgtag cacggctatg cgagaacggg cttcccaaag acttctgtta  10980
ctatttaaac tatataatga gttgtgtgca gacatacttt gactctgagt tctccatcac  11040
caacaattcg caccccgatc ttaatcagtc gtggattgag acatctctt ttgtgcactc  11100 atatgttctg actcctgccc aattaggggg actgagtaac cttcaatact caaggctcta  11160
cactagaaat atcggtgacc cggggactac tgcttttgca gagatccagc gactagaagc  11220
agtgggatta ctgagtccta acattatgac taatatctta actaggccgc ctgggaatgg  11280
agattgggcc agtctgtgca acgacccata ctctttcaat tttgagactg ttgcaagccc  11340
aaatattgtt cttaagaaac atacgcgaag agtcctattt gaaacttgtt caaatcccct  11400
attgtctgga gtgcacacag aggataatga ggcagaagag aaggcattgg ctgaattctt  11460
gcttaatcaa gaggtgattc atccccgcgt tgcgcatgcc atcatggagg caagctctgt  11520
aggtaggaga aagcaaattc aagggcttgt tgacacaaca aacaccgtaa ttaagattgc  11580
gcttactagg aggccattag gcataaagag gctgatgcgg atagtcaatt attctagcat  11640
gcatgcaatg ctgtttagag acgatgtttt ttcctccagt agatccaacc accccttagt  11700
ctcttctaat atgtgttctc tgacactggc agactatgca cggaatagaa gctggtcacc  11760
tttgacggga ggcaggaaaa tactgggtgt atctaatcct gatacgatag aactcgtaga  11820
gggtgagatt cttagtgtaa gcggagggtg tacaagatgt gacagcggag atgaacaatt  11880
tacttggttc catcttccaa gcaatataga attgaccgat gacaccagca agaatcctcc  11940
```

```
gatgagggta ccatatctcg ggtcgaagac acaggagagg agagctgcct cacttgcaaa   12000
aatagctcat atgtcgccac atgtaaaggc tgccctaagg gcatcatccg tgttgatctg   12060
ggcttatggg gataatgacg taaattggac tgctgctctt acgattgcaa aatctcggtg   12120
taatgtaaac ttagagtatc ttcggttact gtcccctta cccacggctg ggaatcttca   12180
acatagacta gatgatggta taactcagat gacattcacc cctgcatctc tctacaggtg   12240
tcaccttaca ttcacatatc caatgattct caaaggctgt tcactgaaga aggagtcaaa   12300
gaggggaatg tggtttacca acagagtcat gctcttgggt ttatctctaa tcgaatcgat   12360 attccaatg acagcaacca ggacatatga tgagatcaca ctgcacctac atagtaaatt   12420
tagttgctgt atcagagaag cacctgttgc ggttcctttc gagctacttg gggtggtacc   12480
ggaactgagg acagtgacct caaataagtt tatgtatgat cctagccctg gatcggaggg   12540
agactttgcg agacttgact tagctatctt caagagttat gagcttaatc tggagtcata   12600
tcccacgata gagctaatga acattctttc aatatccagc gggaagttga ttggccagtc   12660
tgtggtttct tatgatgaag atacctccat aaagaatgac gccataatag tgtacgacaa   12720
tacccgaaat tggatcagtg aagctcagaa ttcagatgtg gtccgcctat ttgaatatgc   12780
agcacttgaa gtgctcctca actgttctta ccaactctat tacctgagag taagaggcct   12840
agacaatatt gtcttatata tgggtgattt atacaagaat atgccaggaa ttctactttc   12900
caacattgca gctacaatat ctcatcccgt cattcattca aggttacatg cagtgggcct   12960
ggtcaaccat gacggatcac accaacttgc agatacggat tttatcgaaa tgtctgcaaa   13020
actattagta tcttgcaccc gacgtgtgat ctccggctta tattcaggaa ataagtatga   13080
tctgctgttc ccatctgtct tagatgataa cctgaatgag aagatgcttc agctgatatc   13140
ccggttatgc tgtctgtaca cggtactctt tgctacaaca agagaaatcc cgaaaataag   13200
aggcttaact acaaaagaga aatgttcaat acccactgag tatttactgt cggatgctgt   13260
gaaaccatta cttagccccg atcaagtgag ctctatcatg tctcctaaca taattacatt   13320
cccagctaat ccgtactaca tgtctcggaa gagcctcaat ttgatcaggg aaagggagga   13380
cagggatact atcctggtgt tgttgttccc ccaagagcca ttattagagt tcccttctgt   13440
gcaagatatt ggtgctcgag tgaaagatcc attcacccga caacctgcgg catttttgca   13500
agagttagat ttgagtgctc cagcaaggta tgacgcattc acacttagtc agattcatcc   13560
tgaactcaca tctccaaatc cggaggaaga ctacttagta cgatacttgt tcagagggat   13620
agggactgca tcttcctctt ggtataaggc atctcatctc ctttctgtac ccgaggtaag   13680
atgtgcaaga cacgggaact ccttatactt agctgaaggg agcggagcca tcatgagtct   13740
tctcgaactg catgtaccac atgaaactat ctattacaat acgctctttt caaatgagat   13800
gaaccccccg caacgacatt tcgggccgac cccaactcag tttttgaatt cggttgttta   13860
taggaatcta caggcggagg taacatgcaa agatggattt gtccaagagt tccgtccatt   13920
atggagagaa aatacagagg aaagtgacct gacctcagat aaagcagtgg ggtatattac   13980
atctgcagtg ccctacagat ctgtatcatt gctgcattgt gacattgaaa ctcctccagg   14040
gtccaatcaa agcttactag atcaactagc tatcaattta tctctgattg ccatgcattc   14100
tgtaagggag ggcgggtag taatcatcaa agtgttgtat gcaatgggat actactttca   14160
tctactcatg aacttgtttg ctccgtgttc cacaaaagga tatattctct ctaatggtta   14220
tgcatgtcga ggagatatgg agtgttacct ggtatttgtc atgggttacc tgggcggcc   14280 tacatttgta catgaggtgg tgaggatggc aaaaactctg gtgcagcggc acggtacgct   14340
```

```
cttgtctaaa tcagatgaga tcacactgac caggttattc acctcacagc ggcagcgtgt   14400
gacagacatc ctatccagtc ctttaccaag attaataaag tacttgagga agaatattga   14460
cactgcgctg attgaagccg ggggacagcc cgtccgtcca ttctgtgcgg agagtctggt   14520
gagcacgcta gcgaacataa ctcagataac ccagattatc gctagtcaca ttgacacagt   14580
tatccggtct gtgatatata tggaagctga gggtgatctc gctgacacag tatttctatt   14640
taccccttac aatctctcta ctgacgggaa aaagaggaca tcacttaaac agtgcacgag   14700
acagatccta gaggttacaa tactaggtct tagagtcgaa aatctcaata aaataggcga   14760
tataatcagt ctagagctta aaggcatgat ctccatggag gaccttatcc cactaaggac   14820
atacttgaag catagtacct gccctaaata tttgaaggct gtcctaggta ttaccaaact   14880
caaagaaatg tttacagaca cttctgtact gtacttgact cgtgctcaac aaaaattcta   14940
catgaaaact ataggcaatg cagtcaacgg atattacagt aactgtgact cttaacgaaa   15000
atcacatatt aataggctcc ttttttggcc aattgtattc ttgttgattt aatcatatta   15060
tgttagaaaa aagttgaacc ctgactcctt aggactcgaa ttcgaactca aataaatgtc   15120
ttaaaaaaag gttgcgcaca attattcttg agtgtagtct cgtcattcac caaatctttg   15180
tttggt                                                              15186
```